(12) United States Patent
Qiu et al.

(10) Patent No.: US 7,329,668 B2
(45) Date of Patent: Feb. 12, 2008

(54) PYRAZOLOPURINE-BASED TRICYCLIC COMPOUNDS AND PHARMACEUTICAL COMPOSITIONS COMPRISING SAME

(75) Inventors: Yuping Qiu, Glastonbury, CT (US); Makonen Belema, North Haven, CT (US); Xuejie Yang, Wallingford, CT (US); Fred Christopher Zusi, Hamden, CT (US); William J. Pitts, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 541 days.

(21) Appl. No.: 10/785,612

(22) Filed: Feb. 24, 2004

(65) Prior Publication Data

US 2004/0204432 A1 Oct. 14, 2004

Related U.S. Application Data

(60) Provisional application No. 60/449,770, filed on Feb. 25, 2003.

(51) Int. Cl.
| | |
|---|---|
| A01N 43/54 | (2006.01) |
| A61K 31/505 | (2006.01) |
| C07D 239/00 | (2006.01) |
| C07D 471/00 | (2006.01) |
| C07D 487/00 | (2006.01) |
| C07D 491/00 | (2006.01) |

(52) U.S. Cl. ........................ 514/267; 544/251
(58) Field of Classification Search ..................... None
See application file for complete search history.

(56) References Cited

U.S. PATENT DOCUMENTS

| 5,306,610 A * | 4/1994 | Ikesu et al. .................. 430/558 |
| 6,492,377 B1 | 12/2002 | Blech et al. |
| 2003/0078277 A1 | 4/2003 | Hibi et al. |

FOREIGN PATENT DOCUMENTS

| JP | 1189728 | 7/1987 |
| JP | 46031228 | 9/1991 |
| JP | 4307543 | 10/1992 |
| WO | WO 9803511 | 1/1998 |
| WO | WO 9833799 | 8/1998 |
| WO | WO 9835968 | 8/1998 |
| WO | WO 0142247 | 6/2001 |

OTHER PUBLICATIONS

West, Anthony R., Solid State Chemistry and Its Applications, Wiley, New York, 1988.*
Wolff, Manfred E., Burger's Medicinal Chemistry and Drug Discovery, Fifth Ed., vol. 1: Principles and Practice, John Wiley & Sons, 1995.*
Banker, Gilbert S. et al., Modem Pharmaceutics, Marcel Dekker, New York, 1996.*
Tenor, E., et al., "1,2,4-Triazoles. VII. Synthesis and reactivity of 7-amino-s-triazolo[1,5-a]-5-pyrimidones", Ber., vol. 97, Issue 5, pp. 1373-1382, 1964.
Takamizawa, A., et al., "Studies on Pyrimidine Derivatives and Related Compounds. LIX. Synthesis of 2,8-Dihydro-1H-pyrazolo[5-1-b]purin-2-ones," Chem. Pharm. Bull, vol. 169, pp. 2195-2199, 1968.

* cited by examiner

*Primary Examiner*—Zachary Tucker
*Assistant Examiner*—Erich Leeser
(74) *Attorney, Agent, or Firm*—Mary K. VanAtten

(57) ABSTRACT

The present invention provides for pyrazolopurine-based tricyclic compounds having the formula (I),

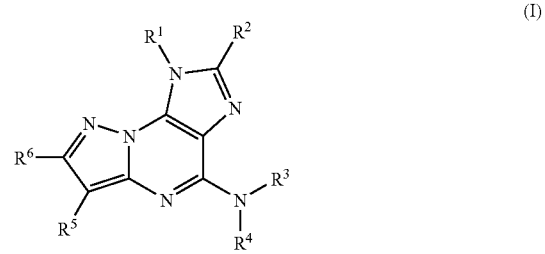

wherein $R^1$, $R^2$, $R^3$, $R^4$, $R^5$ and $R^6$ are as described herein. The present invention further provides pharmaceutical compositions comprising such compounds, as well as the use of such compounds for treating inflammatory and immune diseases.

17 Claims, No Drawings

PYRAZOLOPURINE-BASED TRICYCLIC COMPOUNDS AND PHARMACEUTICAL COMPOSITIONS COMPRISING SAME

CROSS-REFERENCE TO RELATED APPLICATIONS

The present application claims the priority benefit of U.S. Provisional Application No. 60/449,770, filed Feb. 25, 2003, which is expressly incorporated fully herein by reference.

FIELD OF THE INVENTION

The present invention relates to pyrazolopurine-based tricyclic compounds, to methods of using the compounds in treating inflammatory diseases, immune diseases, and cancer and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. Certain neurodegenerative diseases such as Alzheimer's disease, Parkinson's disease, and Creutzfeldt-Jacob disease also are reportedly associated with enhanced TNF-α levels. See, e.g., Arvin et al., "The Role of Inflammation and Cytokines in Brain Injury," Neuroscience and Biobehavioral Reviews, Vol. 20, No. 3 (1996), at pp. 445-452.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs). These drugs are useful in treating a variety of diseases. See Dinarello, "Role of Pro-and Anti-Inflammatory Cytokines During Inflammation: Experimental and Clinical Findings, Review, Vol. 0393-974X (1997), at pp. 91-103.

Recently, attention has focussed on the role of Nuclear factor κB (NF-κB) in the activation pathway that leads to production of TNF-α and other inflammatory cytokines and gene types. Besides TNF-α, NF-κB is involved in the regulation of a variety of genes involved in immune function and inflammation, including IL-2, IL-6, IL-8, IL-2Rα, GM-GSF, intercellular adhesion molecule (ICAM-1), and vascular cellular adhesion molecule-1 (VCAM-1). Thus, inhibition of NF-κB and/or its activation pathway provides a means for treating various diseases including autoimmune diseases, Alzheimer's disease, atherosclerosis, oncogenesis, and so forth. See, e.g., Baldwin, "The NF-κB and I κB Proteins: New Discoveries and Insights," Annual Rev. Immunol., Vol. 14 (1996), at pp. 649-81; see also Christman et al., "Impact of Basic Research on Tomorrow's Medicine, The Role of Nuclear Factor-κB in Pulmonary Diseases," Chest, Vol. 117 (2000), at pp. 1482-87.

Additionally attention has focussed on inhibition of NF-κB and/or its activation pathway to provide a means for treating cancer. Genes which mediate either tumorigenesis or tumor metastasis are regulated by NF-κB. In addition NF-κB is know to be activated by carcinogens and tumor promotors. See e.g., Karin et al.; "NF-κB in Cancer: From Innocent Bystander to Major Culprit," Nature Rev. Cancer., Vol. 2 (2002) at pp. 301-310; see also Bharti et al.; "Nuclear factor-kappa B and cancer: its role in prevention and therapy" in Biochem. Pharmocol. at pp. 883-888.

Potential inhibitors of the NF-κB and/or the NF-κB pathway have been identified as including Interleukin-10, glucocorticoids, salicylates, nitric oxide, and other immunosuppressants. IκB is a cytoplasmic protein that controls NF-κB activity by retaining NF-κB in the cytoplasm. IκB is phosphorylated by the IκB kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Glucocorticoids reportedly inhibit NF-κB activity by two mechanisms, i.e., upregulating IκB protein levels and inhibiting NF-κB subunits. Nitric oxide also reportedly inhibits NF-κB through upregulation of IκB. However, these mechanisms of interaction are complex; for example, production of nitric oxide in lymphocytes reportedly enhances NF-κB activity.

As may be appreciated, those in the field of pharmaceutical research continue to seek to develop new compounds and compositions having increased effectiveness, bioavailability, and solubility, having fewer side effects, and/or providing the consumer with a choice of options. Particularly in the area of immune response, many individuals respond differently depending upon the type of treatment and chemical agent used. Mechanisms of action continue to be studied to aid in understanding the immune response and in developing compounds effective for treating inflammatory and immune-related disorders.

The present invention provides pyrazolopurine-based tricyclic compounds useful as inhibitors of IKK.

SUMMARY OF THE INVENTION

The invention is directed to compounds of formula (I), useful in treating inflammatory or immune conditions:

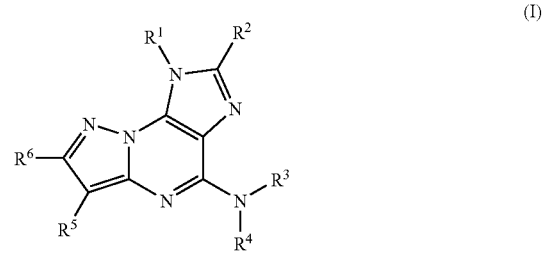

enantiomers, diastereomers, salts, and solvates thereof wherein $R^1$ is
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^1$, $Z^2$ and $Z^3$;

$R^2$ is
(a) hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)

alkyl any of which may be optionally independently substituted as valence allows with one or more $Z^{1a}$, $Z^{2a}$ and $Z^{3a}$; or
(c) —$OR^{10a}$, —$SR^{10a}$, or —$SO_2R^{10a}$ $R^3$ and $R^4$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
(c) —$OR^{11}$, —$NR^{12}R^{13}$, —$N(R^{12})C(O)R^{11}$, —$N(R^{12})C(O)OR^{11}$, —$N(R^{12})SO_2R^{14}$, or —$C(O)NR^{12}R^{13}$, —$SO_2NR^{12}R^{13}$, $N(R^{12})C(O)NR^{12a}R^{13}$, or —$N(R^{12})SO_2NR^{12a}R^{13}$; or
(d) $R^3$ and $R^4$ together with the nitrogen atom to which they are attached combine to form a heterocyclo ring optionally independently substituted as valence allows with one or more $Z^{1b}$, $Z^{2b}$ and $Z^{3b}$;

$R^5$ is
(a) hydrogen, halo, hydroxy, cyano,
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$; or
(c) —$OR^7$, —$C(O)R^7$, —$C(O)OR^7$, or —$NR^8R^9$;

$R^6$ is
(a) hydrogen, hydroxy, halo, or cyano,
(b) alkyl, alkenyl, alkynyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) —$OR^{7a}$, —$NR^{8a}R^{9a}$, —$N(R^{8a})SO_2R^{10}$, —$N(R^{8a})SO_2NR^{8b}R^{9b}$, —$N(R^{8a})C(O)R^{7a}$, —$N(R^{8a})C(O)NR^{8b}R^{9b}$, —$N(R^{8a})C(O)OR^{7a}$, —$C(O)R^{7a}$, —$C(O)OR^{7a}$, —$OC(O)R^{7a}$, —$C(O)NR^{8a}R^{9a}$, or —$OC(O)NR^{8a}R^{9a}$;

$R^7$, $R^{7a}$ and $R^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^8$, $R^{8a}$, $R^{8b}$, $R^9$ $R^{9a}$ and $R^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{1d}$; or
(c) —$OR^{7b}$, —$NR^{8c}R^{9c}$, —$N(R^{8c})SO_2R^{10b}$, —$N(R^{8c})C(O)R^{7b}$, —$N(R^{8c})C(O)OR^{7b}$, —$SO_2NR^{8c}R^{9c}$, —$SO_2R^{10b}$, —$C(O)R^{7b}$, —$C(O)OR^{7b}$, or —$C(O)NR^{8c}R^{9c}$;

$R^{8c}$ and $R^{9c}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{10}$, $R^{10a}$ and $R^{10b}$ are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1-1e}$, $Z^{2-2e}$, and $Z^{3-3e}$ are optional substituents independently selected from
(1) Y, where Y is
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
  (ii) a group (i) which is itself substituted by one or more of the same or different groups (i); or
  (iii) a group (i) or (ii) which is independently substituted by one or more (preferably 1 to 3) of the following groups (2) to (13) of the definition of $Z^1$,
(2) —OH or —OY,
(3) —SH or —SY,
(4) —$C(O)_tH$, —$C(O)_tY$, or —O—C(O)Y, where t is 1 or 2,
(5) —$SO_3H$, or —$S(O)_tY$,
(6) halo,
(7) cyano,
(8) nitro,
(9) —$U^1$—$NY^2Y^3$,
(10) —$U^1$—$N(Y^1)$—$U^2$—$NY^2Y^3$,
(11) —$U^1$—$N(Y^1)$—$U^2$—Y,
(12) —$U^1$—$N(Y^4)$—$U^2$—H,
(13) oxo;

$U^1$ and $U^2$ are each independently
(1) a single bond,
(2) —$U^3$—$S(O)_t$—$U^4$—,
(3) —$U^3$—C(O)—$U^4$—,
(4) —$U^3$—C(S)—$U^4$—,
(5) —$U^3$—O—$U^4$—,
(6) —$U^3$—S—$U^4$—,
(7) —$U^3$—O—C(O)—$U^4$—,
(8) —$U^3$—C(O)—O—$U^4$—, or
(9) —$U^3$—C(=$NV^{1a}$)—$U^4$—;

$Y^1$, $Y^1$, $Y^2$, $Y^3$ and $Y^4$
(1) are each independently hydrogen or a group provided in the definition of $Z^1$; or
(2) $Y^2$ and $Y^3$ may together be alkylene or alkenylene, completing a 3- to 8-membered saturated or unsaturated ring together with the atoms to which they are attached, which ring is unsubstituted or substituted with one or more groups listed in the definition of $Z^1$, or
(3) $Y^2$ or $Y^3$, together with $Y^1$, may be alkylene or alkenylene completing a 3- to 8-membered saturated or unsaturated ring together with the nitrogen atoms to which they are attached, which ring is unsubstituted or substituted with one or more groups listed in the definition of $Z^1$, or
(4) $Y^2$ and $Y^3$ together with the nitrogen atom to which they are attached may combine to form a group —N=CY$^5$Y$^6$ where Y$^5$ and Y$^6$ are each independently H or a group provided in the definition of Y; and U$^3$ and U$^4$ are each independently
(1) a single bond,
(2) alkylene,
(3) alkenylene, or
(4) alkynylene.

In another embodiment of the invention, the present invention is directed to a compound of formula (I),

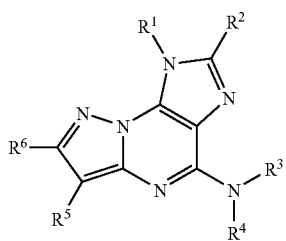

(I)

enantiomers, diastereomers, salts, and solvates thereof wherein

R$^1$ is
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^1$, Z$^2$ and Z$^3$;

R$^2$ is
(a) hydrogen, halo, cyano,
(b) alkyl, alkenyl, alkynyl, haloalkyl, alkoxy, cycloalkoxy, heterocylooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1a}$, Z$^{2a}$ and Z$^{3a}$; or
(c) —OR$^{10a}$, —SR$^{10a}$, or —SO$_2$R$^{10a}$ R$^3$ and R$^4$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1b}$, Z$^{2b}$ and Z$^{3b}$;
(c) —OR$^{11}$, —NR$^{12}$R$^{13}$, —N(R$^{12}$)C(O)R$^{11}$, —N(R$^{12}$)C(O)OR$^{11}$, —N(R$^{12}$)SO$_2$R$^{14}$, or —C(O)NR$^{12}$R$^{13}$, —SO$_2$NR$^{12}$R$^{13}$, —N(R$^{12}$)C(O)NR$^{12a}$R$^{13}$, or —N(R$^{12}$)SO$_2$NR$^{12a}$R$^{13}$; or
(d) R$^3$ and R$^4$ together with the nitrogen atom to which they are attached combine to form a heterocyclo ring optionally independently substituted as valence allows with one or more Z$^{1b}$, Z$^{2b}$ and Z$^{3b}$;

R$^5$ is
(a) hydrogen, halo, hydroxy, cyano,
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$, and Z$^{3c}$; or
(c) —OR$^7$, —C(O)R$^7$, —C(O)OR$^7$, or —NR$^8$R$^9$;

R$^6$ is
(a) hydrogen, hydroxy, halo, or cyano,
(b) alkyl, alkenyl, alkynyl, cycloalkyl, heterocyclo, heteroaryl, (cycloalkyl)alkyl, (heterocyclo)alkyl, (aryl)alkyl, or (heteroaryl)alkyl any of which may be optionally independently substituted as valence allows with one or more Z$^{1d}$, Z$^{2d}$ and Z$^{3d}$; or
(c) —OR$^{7a}$, —NR$^{8a}$R$^{9a}$, —N(R$^{8a}$)SO$_2$R$^{10}$, —N(R$^{8a}$)SO$_2$NR$^{8b}$R$^{9b}$, —N(R$^{8a}$C(O)NR$^{8b}$R$^{9b}$, —N(R$^{8a}$)C(O)OR$^{7a}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$;

R$^7$, R$^{7a}$ and R$^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$ and Z$^{3c}$;

R$^8$, R$^{8a}$, R$^{8b}$, R$^9$ R$^{9a}$ and R$^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1d}$, Z$^{2d}$ and Z$^{1d}$; or
(c) —OR$^{7b}$, —NR$^{8c}$R$^{9c}$, —N(R$^{8c}$)SO$_2$R$^{10b}$, —N(R$^{8c}$)C(O)R$^{7b}$, —N(R$^{8c}$)C(O)OR$^{7b}$, —SO$_2$NR$^{8c}$R$^{9c}$, —SO$_2$R$^{10b}$, —C(O)R$^{7b}$, —C(O)O$^{7b}$, or —C(O)NR$^{8c}$R$^{9c}$;

R$^{8c}$ and R$^{9c}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1d}$, Z$^{2d}$ and Z$^{3d}$;

R$^{10}$, R$^{10a}$ and R$^{10b}$ are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1d}$, Z$^{2d}$ and Z$^{3d}$;

R$^{11}$, R$^{12}$, R$^{12a}$ and R$^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1e}$, Z$^{2e}$ and Z$^{3e}$;

R$^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1e}$, Z$^{2e}$ and Z$^{3e}$;

Z$^{1-1e}$, Z$^{2-2e}$, and Z$^{3-3e}$ are optional substituents independently selected from
(1) Y, where Y is
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (ii) a group (i) which is itself substituted by one or more of the same or different groups (i); or
  (iii) a group (i) or (ii) which is independently substituted by one or more (preferably 1 to 3) of the following groups (2) to (13) of the definition of Z$^1$,
(2) —OH or —OY$^1$,
(3) —SH or —SY$^1$, (4) —C(O)$_t$H, —C(O)$_t$Y$^1$, or —O—C(O)Y$^1$, where t is 1 or 2,
(5) —SO$_3$H, or —S(O)$_t$Y$^1$,
(6) halo,
(7) cyano,
(8) nitro,
(9) —U$^1$—NY$^2$Y$^3$,
(10) —U$^1$—N(Y$^1$)—U$^2$—NY$^2$Y$^3$,
(11) —U$^1$—N(Y$^4$)—U$^2$—Y$^1$,
(12) —U$^1$—N(Y$^4$)—U$^2$—H,
(13) oxo;

U$^1$ and U$^2$ are each independently
(1) a single bond,
(2) —U$^3$—S(O)$_t$—U$^4$—,
(3) —U$^3$—C(O)—U$^4$—,
(4) —U$^3$—C(S)—U$^4$—,
(5) —U$^3$—O—U$^4$—,
(6) —U$^3$—S—U$^4$—,
(7) —U$^3$—O—C(O)—U$^4$—,
(8) —U$^3$—C(O)—O—U$^4$—, or
(9) —U$^3$—C(=NV$^{1a}$)—U$^4$—;

V$^{1a}$ is independently hydrogen, alkyl, —CN, —C(O)Y$^1$, —S(O)$_2$Y$^5$, S(O)$_2$NY$^2$Y$^3$;

Y$^1$, Y$^2$, Y$^3$ and Y$^4$
(1) are each independently hydrogen or a group provided in
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (ii) a group (i) which is itself substituted by one or more of the same or different groups (i),
  (iii) a group (i) or (ii) which is independently substituted by one or more (preferably 1 to 3) of the following groups (1) to (12) of the definition of Z$^4$, or
(2) Y$^2$ and Y$^3$ may together be alkylene or alkenylene, completing a 3- to 8-membered saturated or unsaturated ring together with the atoms to which they are attached, which ring is unsubstituted or substituted with one or more groups selected from alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, or
(3) Y$^2$ or Y$^3$, together with Y$^1$, may be alkylene or alkenylene completing a 3- to 8-membered saturated or unsaturated ring together with the nitrogen atoms to which they are attached, which ring is unsubstituted or substituted with one or more groups selected from alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, or
(4) Y$^2$ and Y$^3$ together with the nitrogen atom to which they are attached may combine to form a group —N=CY$^5$Y$^6$ where Y$^5$ and Y$^6$ are each independently H or a group provided selected from alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; and Z$^4$ is
(1) —OH or OY$^a$,
(2) —SH or —SY$^a$,
(3) —C(O)$_t$H, —C(O)$_t$Y$^a$, or —O—C(O)Y$^a$, where t is 1 or 2,
(4) —SO$_3$H, or —S(O)$_t$Y$^a$,
(5) halo,
(6) cyano,
(7) nitro,
(8) —U$^1$—NY$^b$Y$^c$,
(9) —U$^1$—N(Y$^1$)—U$^2$—NY$^b$Y$^c$,
(10) —U$^1$—N(Y$^d$)—U$^2$—Y$^a$,
(11) —U$^1$—N(Y$^d$)—U$^2$—H,
(12) oxo;

Y$^a$, Y$^b$, Y$^c$ and Y$^d$
(1) are each independently hydrogen or a group provided in
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

U$^3$ and U$^4$ are each independently
(1) a single bond,
(2) alkylene,
(3) alkenylene, or
(4) alkynylene.

The invention also relates to pharmaceutical compositions containing at least one compound of formula (I) and a pharmaceutically-acceptable carrier or diluent, for use in treating inflammatory and immune diseases. Also included within the invention are methods of treating such diseases comprising administering to a mammal in need of such treatment an effective amount of at least one compound of formula (I).

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Lower alkyl groups, that is, alkyl groups of 1 to 4 carbon atoms, are often most preferred.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

When the term "alkyl" is used together with another group, such as in "(aryl)alkyl", this conjunction is meant to refer to a substituted alkyl group wherein at least one of the substituents is the specifically named group in the conjunction. For example, "(aryl)alkyl" refers to a substituted alkyl group as defined above wherein at least one of the substituents is an aryl, such as benzyl.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

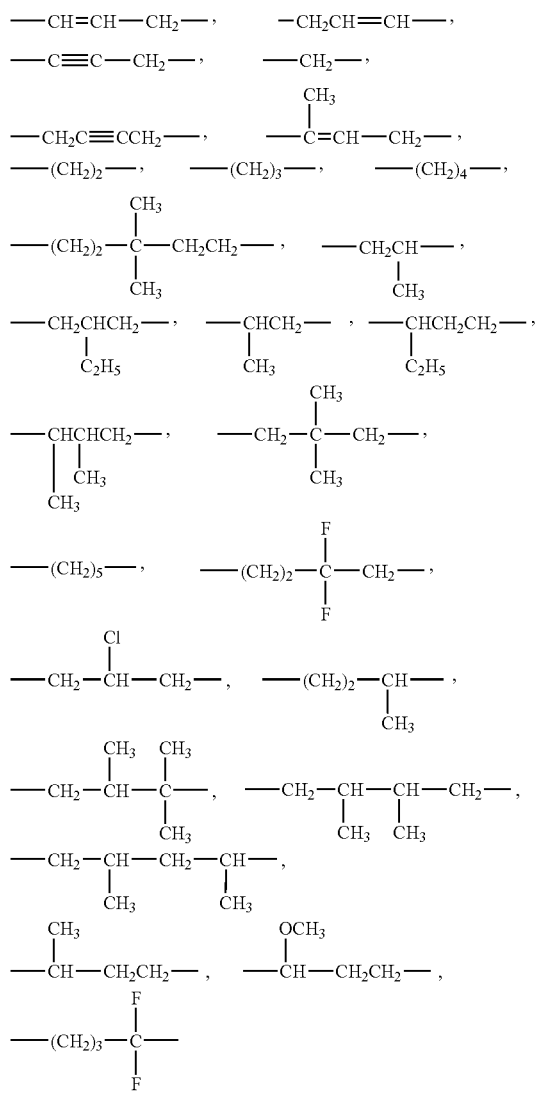

and the like. Alkylene groups may be optionally independently substituted as valence allows with one or more groups provided in the definition of $Z^1$.

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

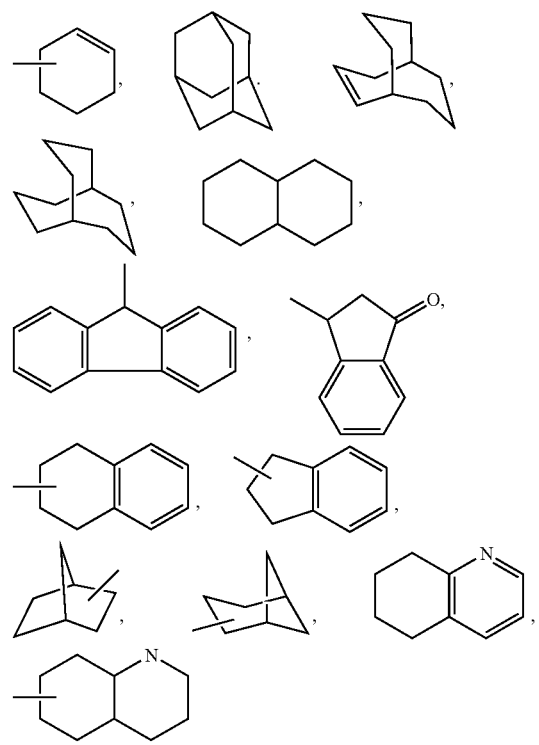

and the like.

The term "cycloalkylene" as employed herein refers to a "cycloalkyl" group which includes free bonds and thus is a linking group such as

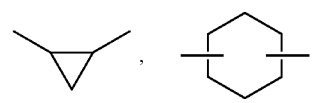

and the like.

One skilled in the field will understand that, when the designation "CO$_2$" is used herein, this is intended to refer to the group

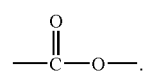

The term "alkoxy" refers to an alkyl or substituted alkyl group as defined above bonded through an oxygen atom (—O—), i.e., the groups —OR$_d$, wherein R$_d$ is alkyl or substituted alkyl.

The term "alkylthio" refers to an alkyl or substituted alkyl group as defined above bonded through a sulfur atom (—S—), i.e., the groups —SR$_d$, wherein R$_d$ is alkyl or substituted alkyl.

The term "acyl" refers to a carbonyl group linked to an organic radical, more particularly, the group C(=O)R$^g$, wherein R$^g$ can be selected from alkyl, alkenyl, substituted alkyl, or substituted alkenyl, as defined herein.

The term "alkoxycarbonyl" refers to a carboxy group

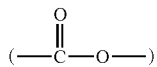

linked to an organic radical (CO$_2$R$_g$), wherein R$_g$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

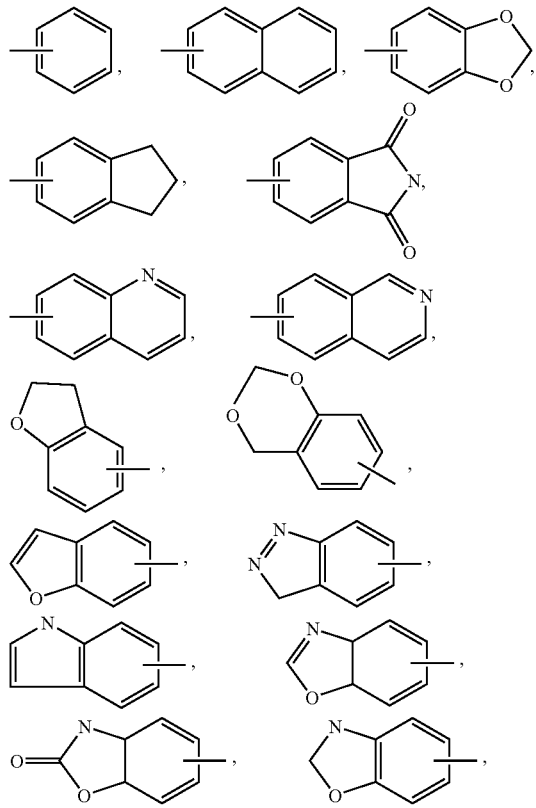

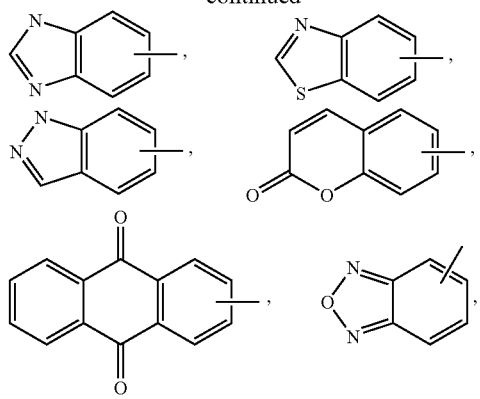

and the like.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

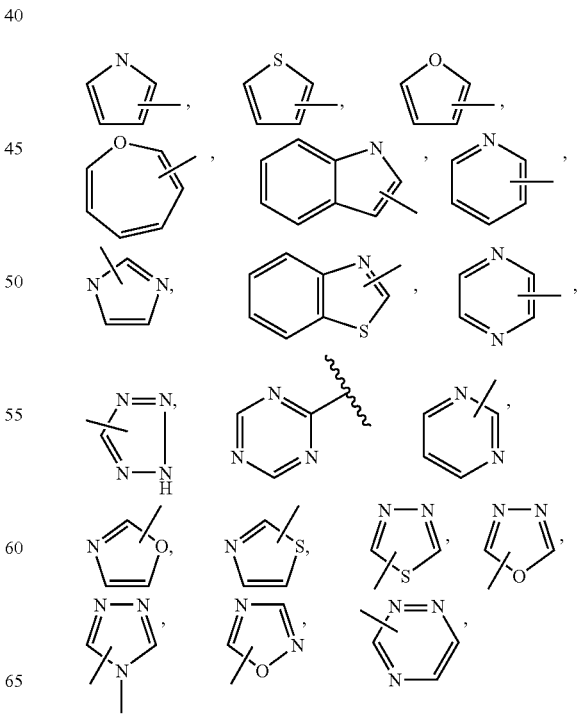

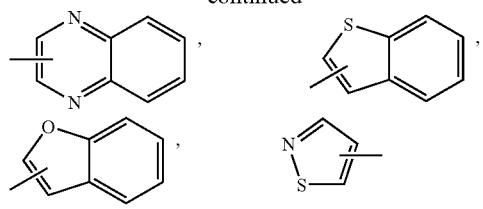

and the like.

In compounds of formula (I), preferred heteroaryl groups include

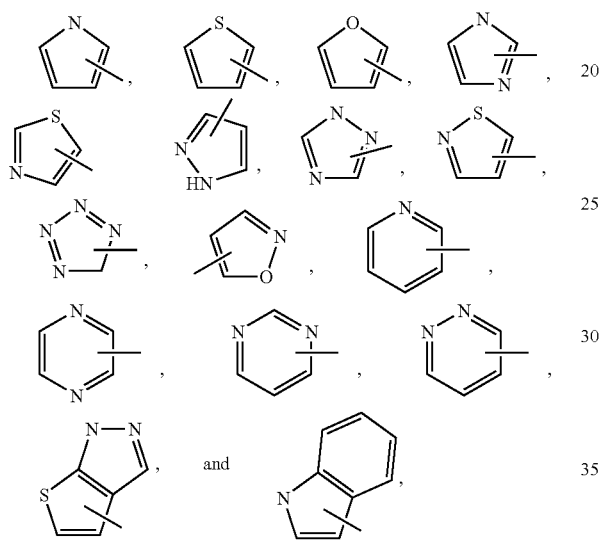

and the like, which optionally may be substituted at any available carbon or nitrogen atom.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Preferred heterocyclo groups in compounds of formula (I) include

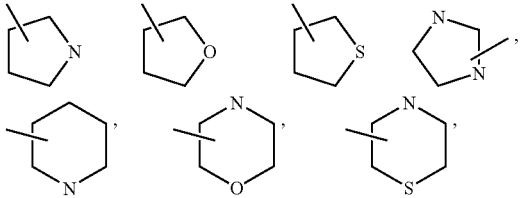

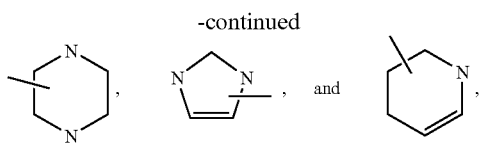

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl).

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds. One skilled in the field may make the appropriate selections for B and X to provide stable compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

"Therapeutically effective amount" is intended to include an amount of a compound of the present invention alone or an amount of the combination of compounds claimed or an amount of a compound of the present invention in combination with other active ingredients effective to inhibit or suppress IKK or effective to treat inflammatory disorders, immune disorder, or cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

METHODS OF PREPARATION

The inventive compounds may be prepared by methods such as those illustrated in the following Schemes 1 to 3. Starting materials are commercially available or can be readily prepared by one of ordinary skill in the art, and/or modifications can be made to the methods of Schemes 1 to 3 by one skilled in the art, using known methods. For all of the schemes and compounds, the groups $R^1$, $R^2$, $R^3$, $R^4$, $R^5$ and $R^6$ are as described herein for a compound of formula I, unless otherwise indicated, and appropriate starting materials may be selected by one skilled in the field having the desired groups. Solvents, temperatures, pressures, and other reaction conditions may readily be selected as appropriate by one of ordinary skill in the art. For example, in these schemes chlorinating agents may include phosphorous oxychloride, catalytic agents may include metals such as Pd, and solvents may be selected from 1,2-dichlorobenzene, methylene chloride, DMF, alcohols, ethers, THF, dioxane, acetonitrile, water, mixtures of ethers and water, and the like.

"Cross-coupling" or coupling reactions as used in the schemes and examples may include all cross-coupling methods known by those skilled in the art. Such methods include Stille-type coupling (reacting a vinyl or aromatic triflate, bromide or iodide with a tin), Suzuki-type coupling (reacting a zinc, magnesium or boronate derivative catalyzed by palladium(0), palladium(II), nickel(0) or nickel(II)), Heck coupling, and Sonogashira coupling. Copper iodide, lithium chloride, zinc chloride, triphenylarsine, tris(2-furyl)phosphine or tris(2,4,6-trimethoxyphenyl)-phosphine advantageously may also be added. When a boronic acid derivative is used, the reaction may proceed in the presence of an inorganic base such as sodium carbonate or potassium phosphate or carbonate. The cross-coupling reactions are performed in an inert organic solvent.

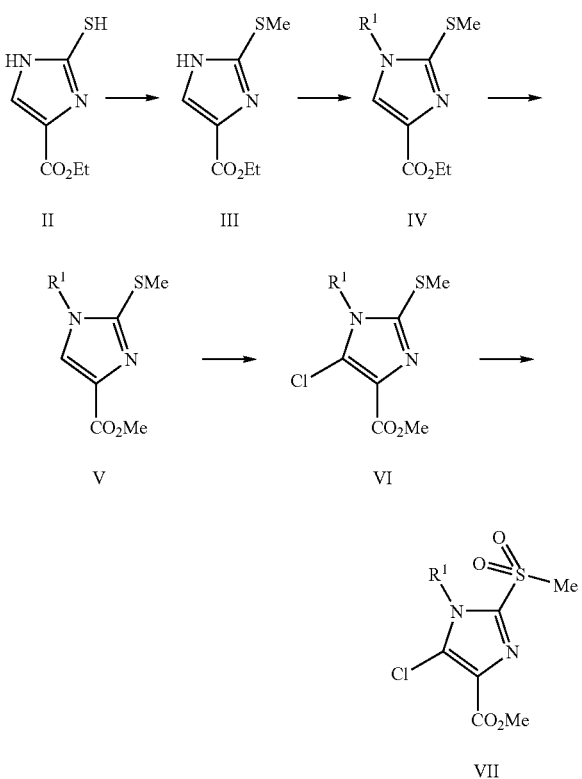

Scheme 1

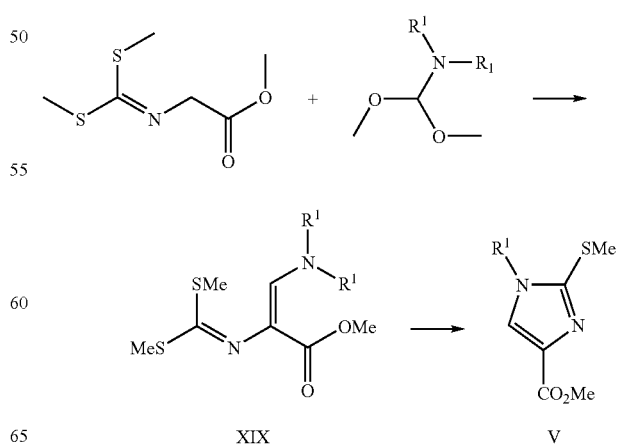

Scheme 1a

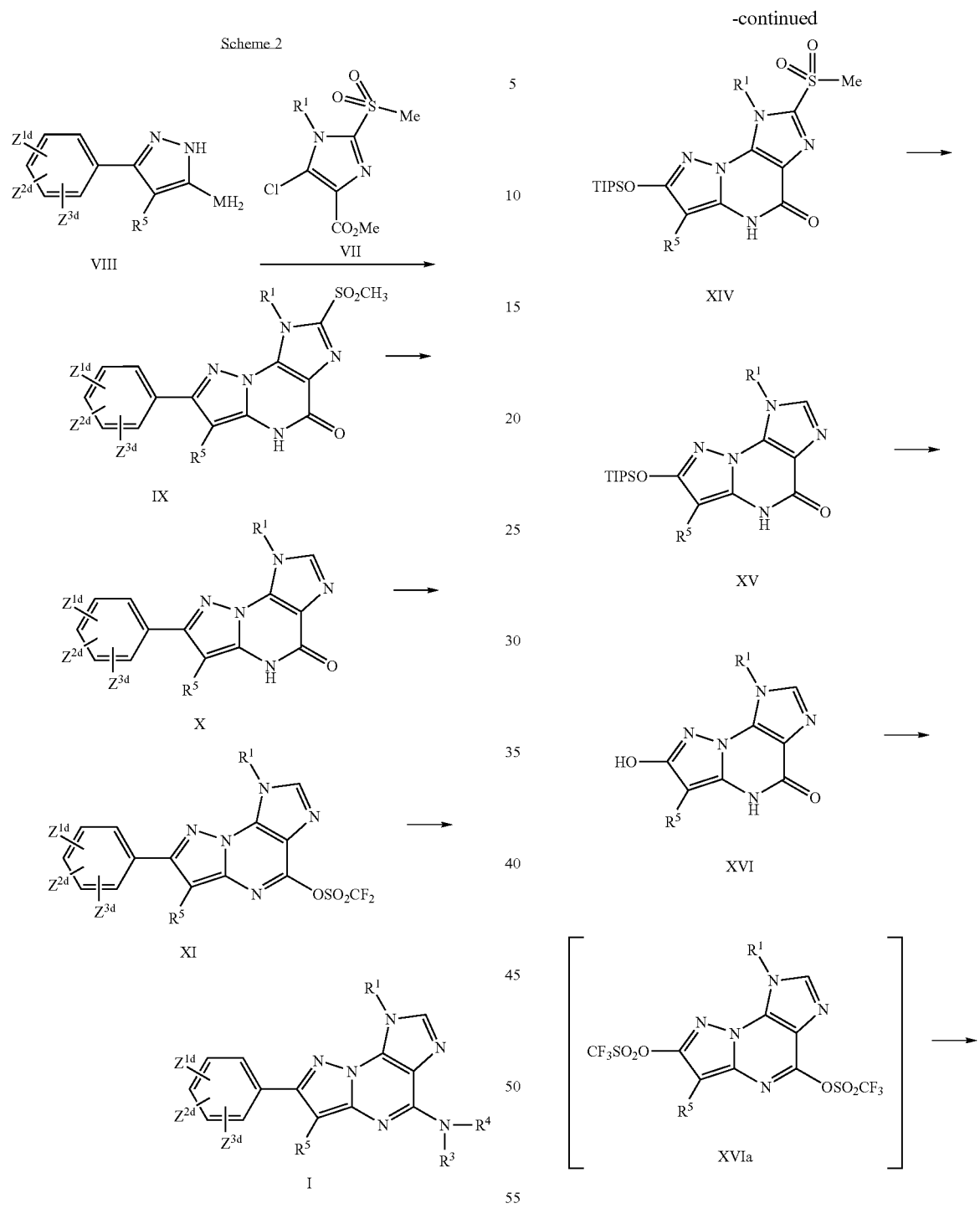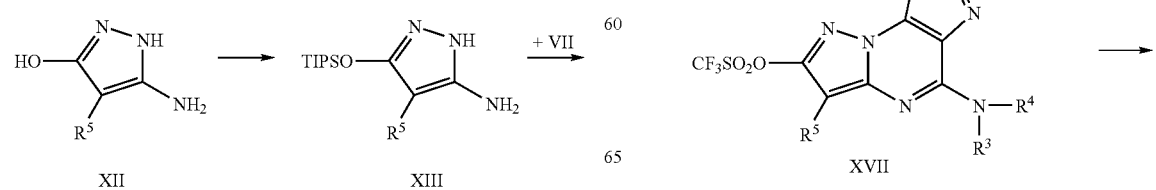

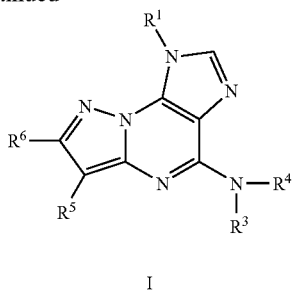

I

Key intermediate VII may be prepared from commercially available ethyl 2-mercaptoimidazole-4-carboxylate, II, as shown in Scheme 1. The mercapto group is first methylated to give III, followed by N-alkylation to give IV, wherein $R^1$ is alkyl. IV is transesterified to give V, which is chlorinated to give VI followed by oxidation to give VII. Alternatively, compound V may be prepared through intermediate XIX, as shown in Scheme 1a.

The synthesis of final compounds I, wherein $R^6$ is optionally substituted phenyl, is shown in Scheme 2. 3-Amino-5-phenylpyrazole VIII is condensed with VII to give pyrazolopurine IX. The methanesulfonyl group of IX is reduced off to give X and the carbonyl group of X is activated by conversion to trifluoromethanesulfonate XI. XI is then converted to I by condensation with appropriate amines.

A more versatile synthetic route is shown in Scheme 3. Pyrazole XII is protected as the tri-isopropylsilyl ether XIII, which is condensed with intermediate VII to give pyrazolopurine XIV. The methanesulfonyl group of XIV is removed by reduction to give XV, and the silyl group is removed to give XVI, which is activated to the di-trifluoromethanesulfonate XVIa. The 4-sulfonate group is replaced with selected amines to give XVII, which is cross-coupled with the desired aryl or heteroaryl stannanes or boronates to give final compounds I.

PREFERRED COMPOUNDS

Preferred compounds within the scope of formula I include compounds wherein $R^1$ is hydrogen, alkyl or haloalkyl;
$R^2$ is hydrogen, halogen, alkyl, haloalkyl;
$R^3$ and $R^4$ are independently
 (a) hydrogen,
 (b) alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$; or
 (c) $R^3$ and $R^4$ together with the nitrogen atom to which they are attached combine to form a heterocyclo ring optionally independently substituted as valence allows with one or more $Z^{1b}$, $Z^{2b}$ and $Z^{3b}$;
$R^5$ is hydrogen, halogen, alkyl or haloalkyl;
$R^6$ is
 (a) alkyl, alkenyl, alkynyl or aryl any of which may be optionally independently substituted as valence allows with one or more $Z^{1d}$, $Z^{2d}$ and $Z^{3d}$; or
 (b) —$OR^{7a}$;
$R^{7a}$ is alkyl optionally substituted with $Z^{1c}$;

$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$N(Y^1)$—$U^2$—$NY^2Y^3$, —$N(Y^1)$—$U^2$—Y, or —$N(Y^4)$—$U^2$—H;
$Z^{1c}$ is
 (a) —OH, —OY or
 (b) aryl optionally substituted with —OH or —OY;
$Z^{1d}$, $Z^{2d}$ and $Z^{3d}$ are optional substituents independently selected from
 (a) cyano, halo, —OH, —OY, —$U^1$—$NY^2Y^3$, —$C(O)_tH$, —$C(O)_tY$, —$S(O)_tY$, —$N(Y^1)$—$U^2$—$NY^2Y^3$, —$N(Y^4)$—$U^2$—Y, or —$N(Y^4)$—$U^2$—H;
 (b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$N(Y^1)$—$U^2$—$NY^2Y^3$, —$N(Y^4)$—$U^2$—Y, or —$N(Y^4)$—$U^2$—H.

More preferred compounds within the scope of formula I include compounds wherein
$R^1$ is alkyl;
$R^2$ is hydrogen;
$R^3$ is hydrogen;
$R^4$ is alkyl, haloalkyl, (hydroxy)alkyl, cycloalkyl (preferably cyclopropyl), (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$;
$R^5$ is hydrogen;
$R^6$ is
 (a) alkynyl optionally substituted with $Z^{1d}$ where $Z^{1d}$ is aryl which may be further optionally independently substituted with one or more cyano, halo, —OH, —OY, —$U^1$—$NY^2Y^3$, —$C(O)_tH$, —$C(O)_tY$, —$S(O)_tY$, —$N(Y^1)$—$U^2$—$NY^2Y^3$, —$N(Y^4)$—$U^2$—Y, or —$N(Y^4)$—$U^2$—H;
 (b) aryl optionally independently substituted as valence allows with one or more $Z^{1d}$, $Z^{2d}$ and $Z^{3d}$; or
 (c) —$OR^{7a}$;
$R^{7a}$ is alkyl optionally substituted with $Z^{1c}$;
$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$N(Y^4)$—$U^2$—Y, or —$N(Y^4)$—$U^2$—H
 where
 $U^1$ is a bond,
 $U^2$ is —$U^3$—C(O)—$U^4$— or —$U^3$—C(O)O—$U^4$— and
 $U^3$ and $U^4$ are indepedently a bond or alkylene;
$Z^{1c}$ is
 (a) —OY where Y is aryl, or
 (b) aryl optionally substituted with —OH or —OY where Y is alkyl;
$Z^{1d}$, $Z^{2d}$ and $Z^{3d}$ are optional substituents independently selected from
 (a) cyano, halo, —OH, —OY, —$C(O)_tH$, —$C(O)_tY$, —$S(O)_tY$, or
 (b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$N(Y^4)$—$U^2$—Y, or —$N(Y^4)$—$U^2$—H
 where
 $U^1$ is a bond, or —C(O)—,
 $U^2$ is —$U^3$—C(O)—$U^4$—, —$U^3$—C(O)O—$U^4$—, or —$U^3$—$SO_2$—$U^4$—, and
 $U^3$ and $U^4$ are indepedently a bond or alkylene.

Preferred compounds within the scope of formula I include compounds of the following formulae IIa and IIb:

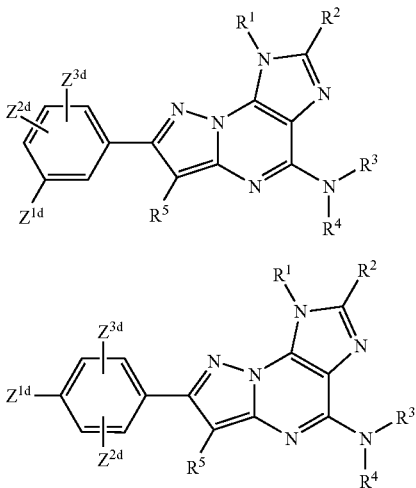

wherein
R$^1$, R$^2$, R$^3$, R$^4$, and R$^5$ are as defined above in the description of compounds of formula I (including the description of preferred groups);
Z$^{1d}$ is
(a) cyano, halo, —OH, —OY, —C(O)$_t$H, —C(O)$_t$Y, —S(O)$_t$Y, or
(b) alkyl or alkoxy optionally substituted with one or more cyano, halo, —OH, —OY, —U$^1$—NY$^2$Y$^3$, —C(O)$_t$H, —C(O)$_t$Y, —S(O)$_t$Y, —N(Y$^4$)—U$^2$—Y, or —N(Y$^4$)—U$^2$—H
where
U$^1$ is a bond, or —C(O)—,
U$^2$ is —U$^3$—C(O)—U$^4$—, —U$^3$—C(O)O—U$^4$—, or —U$^3$—SO$_2$—U$^4$—, and
U$^3$ and U$^4$ are indepedently a bond or alkylene; and
Z$^{2d}$ and Z$^{3d}$ are optional substituents independently selected from
(a) cyano, halo, —OH, —OY, —C(O)$_t$H, —C(O)$_t$Y, —S(O)$_t$Y, or
(b) alkyl or alkoxy optionally substituted with one or more cyano, halo, —OH, —OY, —U$^1$—NY$^2$Y$^3$, —C(O)$_t$H, —C(O)$_t$Y, —S(O)$_t$Y, —N(Y$^4$)—U$^2$—Y, or —N(Y$^4$)—U$^2$—H
where
U$^1$ is a bond, or —C(O)—,
U$^2$ is —U$^3$—C(O)—U$^4$—, —U$^3$—C(O)O—U$^4$—, or —U$^3$—SO$_2$—U$^4$—, and
U$^3$ and U$^4$ are indepedently a bond or alkylene.

In another embodiment of the invention, the invention is directed to a compound of formula (I), wherein
Z$^{1b}$, Z$^{2b}$ and Z$^{3b}$ are optional substituents independently selected from —OH, —OY$^1$, —U$^1$—NY$^2$Y$^3$, —C(O)$_t$H, —C(O)$_t$Y$^1$, —N(Y$^1$)—U$^2$—NY$^2$Y$^3$, —N(Y$^4$)—U$^2$—Y$^1$, or —N(Y$^4$)—U$^2$—H;
Z$^{1c}$ is
(a) —OH, —OY$^1$ or
(b) aryl optionally substituted with —OH or —OY$^1$;
Z$^{1d}$, Z$^{2d}$ and Z$^{3d}$ are optional substituents independently selected from
(a) cyano, halo, —OH, —OY$^1$, —U$^1$—NY$^2$Y$^3$, —C(O)$_t$H, —C(O)$_t$Y$^1$, —S(O)$_t$Y$^1$, —N(Y$^1$)—U$^2$—NY$^2$Y$^3$, —N(Y$^4$)—U$^2$—Y, or —N(Y$^4$)—U$^2$—H;

(b) alkyl or alkoxy optionally substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^1$)—U$^2$—NY$^2$Y$^3$, —N(Y$^4$)—U$^2$—Y$^1$, or —N(Y$^4$)—U$^2$—H.

In another embodiment of the invention, the invention is directed to a compound of formula (I), wherein
R$^3$ is hydrogen;
R$^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$;
R$^6$ is
(a) alkynyl optionally substituted with Z$^{1d}$ where Z$^{1d}$ is aryl which may be further optionally independently substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^1$)—U$^2$—NY$^2$Y$^3$, —N(Y$^4$)—U$^2$—Y$^1$, or —N(Y$^4$)—U$^2$—H;
(b) aryl optionally independently substituted as valence allows with one or more Z$^{1d}$, Z$^{2d}$ an Z$^{3d}$;
(c) —OR$^{7a}$; or
(d) heterocyclo optionally independently substituted as valence allows with one or more Z$^{1d}$, Z$^{2d}$ and Z$^{3d}$;
Z$^{1b}$, Z$^{2b}$ and Z$^{3b}$ are optional substituents independently selected from —OH, —OY$^1$, —U$^1$—NY$^2$Y$^3$, —C(O)$_t$H, —C(O)$_t$Y$^1$, —N(Y$^4$)—U$^2$—Y, or —N(Y$^4$)—U$^2$—H
where
U$^1$ is a bond,
U$^2$ is —U$^3$—C(O)—U$^4$— or —U$^3$—C(O)O—U$^4$— and
U$^3$ and U$^4$ are independently a bond or alkylene;
Z$^{1c}$ is
(a) —OY$^1$ where Y$^1$ is aryl, or
(b) aryl optionally substituted with —OH or —OY$^1$ where Y$^1$ is alkyl;
Z$^{1d}$, Z$^{2d}$ and Z$^{3d}$ are optional substituents independently selected from
(a) cyano, halo, —OH, —OY$^1$, —C(O)$_t$H, —C(O)$_t$Y$^1$, —S(O)$_t$Y$^1$, or
(b) alkyl or alkoxy optionally substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^4$)—U$^2$—Y$^1$, or —N(Y$^4$)—U$^2$—H
where
U$^1$ is a bond, or —C(O)—,
U$^2$ is —U$^3$—C(O)—U$^4$—, —U$^3$—C(O)O—U$^4$—, or —U$^3$—SO$_2$—U$^4$—, and
U$^3$ and U$^4$ are indepedently a bond or alkylene.

In another embodiment of the invention, the invention is directed to a compound of formula (I), wherein
R$^1$ is alkyl;
R$^2$ is hydrogen; and
R$^5$ is hydrogen or alkyl.

In another embodiment of the invention, the invention is directed to a compound of formula (I), wherein
Z$^{1d}$ is
(a) cyano, halo, —OH, —OY$^1$, —C(O)$_t$H, —C(O)$_t$Y$^1$, —S(O)$_t$Y$^1$, or
(b) alkyl or alkoxy optionally substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^4$)—U$^2$—Y$^1$, or —N(Y$^4$)—U$^2$—H
where
U$^1$ is a bond, or —C(O)—,
U$^2$ is —U$^3$—C(O)—U$^4$—, —U$^3$—C(O)O—U$^4$—, or —U$^3$—SO$_2$—U$^4$—, and $U^3$ and $U^4$ are indepedently a bond or alkylene; and
$Z^{2d}$ and $Z^{3d}$ are optional substituents independently selected from
(a) cyano, halo, —OH, —$OY^1$, —$C(O)_rH$, —$C(O)_rY^1$, —$S(O)_tY^1$, or
(b) alkyl or alkoxy optionally substituted with one or more cyano, halo, —OH, —$OY^1$, —$U^1$—$NY^2Y^3$, —$C(O)_rH$, —$C(O)_rY^1$, —$S(O)_tY^1$, —$N(Y^4)$—$U^2$—$Y^1$, or —$N(Y^4)$—$U^2$—H
where
$U^1$ is a bond, or —C(O)—,
$U^2$ is —$U^3$—C(O)—$U^4$—, —$U^3$—C(O)O—$U^4$—, or —$U^3$—$SO_2$—$U^4$—, and
$U^3$ and $U^4$ are indepedently a bond or alkylene.

In another embodiment of the invention, the invention is directed to a compound of formula (I), wherein
$R^3$ and $R^4$ are independently
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$; or
(c) $R^3$ and $R^4$ together with the nitrogen atom to which they are attached combine to form a heterocyclo ring optionally independently substituted as valence allows with one or more $Z^{1b}$, $Z^{2b}$ and $Z^{3b}$.

In another embodiment of the invention, the invention is directed to a compound of formula (I), wherein
$Z^{1b}$, $Z^{2b}$ and $Z^{3b}$ are optional substituents independently selected from —OH, —$OY^1$, —$U^1$—$NY^2Y^3$, —$C(O)_rH$, —$C(O)_tY^1$, —$N(Y^1)$—$U^2$—$NY^2Y^3$, —$N(Y^4)$—$U^2$—$Y^1$, or —$N(Y^4)$—$U^2$—H.

UTILITY

The compounds and compositions of this invention are useful in treating conditions that are characterized by the activity of IKK, release of NF-κB, and/or enhanced levels of TNF-α. The term "treating" or "treatment" denotes prevention, partial alleviation, or cure of the disease or disorder or its symptoms or consequences. Inhibition or suppression of IKK, NF-κB and/or TNF-α may occur locally, for example, within certain tissues of the subject, or more extensively throughout the subject being treated for such a disease. Inhibition or suppression of IKK, NF-κB and/or TNF-α may occur by one or more mechanisms, e.g., by inhibiting or suppressing any step of the pathway(s). The term "NF-κB-associated condition" refers to diseases that are characterized by release of NF-κB from the cytoplasm (e.g., upon phosphorylation of IκB). The term "TNF-α-associated condition" is a condition characterized by enhanced levels of TNF-α. In the instant specification, the term "NF-κB-associated condition" will include a TNF-α-associated condition but is not limited thereto as NF-κB is involved in the activity and upregulation of other pro-inflammatory proteins and genes. The term "inflammatory or immune disease" is used herein to encompass IKK-associated conditions, NF-κB-associated conditions, and TNF-α-associated conditions, e.g., any condition, disease, or disorder that is associated with activity of IKK, NF-κB and/or enhanced levels of TNF-α.

The inventive compounds and compositions are useful for treating a variety of diseases including, but not limited to, treatment of transplant rejections (e.g., kidney, liver, heart, lung, pancreas, bone marrow, cornea, small bowel, skin allografts, skin homografts and heterografts, etc.) or tolerance to organ transplantion; rheumatoid arthritis, psoriatic arthritis, multiple sclerosis, inflammatory bowel disease (such as Crohn's disease and ulcerative colitus); antiviral and autoimmune diseases including herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, and autoimmune polyglandular disease (also known as autoimmune polyglandular syndrome); Alzheimer's, Parkinson's, and Creutzfeldt-Jacob diseases; septic shock; hematopoiesis; inflammatory diseases such as osteoarthritis, acute pancreatitis, and chronic pancreatitis; inflammatory disorders of the central nervous system, including HIV encephalitis, cerebral malaria, and meningitis, atherosclerosis, and ataxia telangiectasis; respiratory allergies including asthma, hayfever, and allergic rhinitis; fungal infections such as mycosis fungoides; and psoriasis, glomerulonephritis, serum sickness, lupus (systematic lupus erythematosis), urticaria, scleraclerma, contact dermatitis, dermatomyositis, alopecia, atopic eczemas, and ichthyosis. The term "inflammatory or immune disease" as used herein includes all of the above-referenced diseases and disorders.

The inventive compounds are also effective in treating oncological diseases, in treating cancer and tumors, such as solid tumors, lymphomas and leukemia, and in particular, breast cancer, prostate cancer, and Hodgkin's lymphoma.

Additionally this invention relates to a pharmaceutical composition of a compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid or liquid tumors which are associated with IKK, especially those tumors which are significantly dependent on IKK for their growth and spread, including for example, hematopoietic tumors, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of the skin, including melanoma;

hematopoietic tumors including those of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

hematopoietic tumors including those of plasma cell lineage such as multiple myeloma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of IKK kinase activity, such as melanomas, and multiple myeloma. By the administration of a composition (or a combination) of the compounds of this invention, development of tumors in a mammalian host is reduced.

The invention also provides a pharmaceutical composition comprising a compound of formula I in combination with pharmaceutically acceptable carrier and an anti-cancer or cytotoxic agent. In one embodiment said anti-cancer or cytotoxic agent is selected from the group consisting of linomide; inhibitors of integrin αvβ3 function; angiostatin; razoxin; tamoxifen; toremifen; raloxifene; droloxifene; iodoxyfene; megestrol acetate; anastrozole; letrazole; borazole; exemestane; flutamide; nilutamide; bicalutamide; cyproterone acetate; gosereline acetate; luprolide; finasteride; metalloproteinase inhibitors; inhibitors of urokinase plasminogen activator receptor function; growth factor antibodies; growth factor receptor antibodies such as Avastin® and Erbitux®; tyrosine kinase inhibitors; serine/threonine kinase inhibitors); methotrexate; 5-fluorouracil; purine; adenosine analogues; cytosine arabinoside; doxorubicin; daunomycin; epirubicin; idarubicin; mitomycin-C; dactinomycin; mithramycin); cisplatin; carboplatin; nitrogen mustard; melphalan; chlorambucil; busulphan; cyclophosphamide; ifosfamide nitrosoureas; thiotephan; vincristine; Taxol®; Taxotere®; epothilone analogs; discodermolide analogs; eleutherobin analogs; etoposide; teniposide; amsacrine; topotecan; and flavopyridols.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

1: antiangiogenic agents such as inhibitors of VEGF or related kinases (such as FLT, or KDR), linomide, antibodies which block angiogenesis, inhibitors of integrin αvβ3 function, angiostatin, razoxin;

2: cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antiharmones, antiprogestogens, antiandrogens (for example flutamide, nilutamide, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® and Erbitux®, tyrosine kinase inhibitors and serine/threonine kinase inhibitors);

3: antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like Taxol®, Taxotere® and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols).

The present invention thus provides methods for treating such conditions, comprising administering to a subject in need thereof an effective amount of at least one compound of formula I or a salt thereof. Other therapeutic agents such as those described below may be employed in combination with compounds of formula I. In the methods of the present invention, such other therapeutic agent(s) may be administered prior to, simultaneously with, or following administration of the inventive compound(s).

The present invention also provides pharmaceutical compositions capable of treating IKK, NF-κB and/or TNF-α associated conditions, as described above. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like, subject to IKK, NF-κB and/or TNF-α associated conditions.

The inventive compounds and compositions may be employed alone or in combination with each other and/or other suitable therapeutic agents useful in treating IKK, NF-κB and/or TNF-α associated conditions. Exemplary of such other therapeutic agents include corticosteroids, rolipram, calphostin, CSAIDs, 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergulin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof; and other cancer drugs and treatments, including radiation treatments and daunorubicin.

The above other therapeutic agents, when employed in combination with the compounds of the present invention, may be used, for example, in those amounts indicated in the Physicians' Desk Reference (PDR) or as otherwise determined by one of ordinary skill in the art.

The inventive compounds have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells ($1.4 \times 10^6$/mL, $2.5 \times 10^5$ cells/well) in 180 µL RPMI-1640 was added 10 µL of the test compound in 10% DMSO. Typically, test compound concentrations of 0.1-100 µM were used in the assay. After one hour at 37° C., 10 µL of 1000 ng/mL lipopolysaccharide (LPS from *Salmonella typhosa*, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFα secretion model. Likewise, assays known in the field are applied to establish the activity of the compounds as inhibitors of IKK, IkB, and/or the NF-κB pathway.

EXPERIMENTALS

Abbreviations

For ease of reference, the following abbreviations are employed herein, including in the methods of preparation hereinbefore and in the Examples that follow:

Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DMF=dimethyl formamide
DMSO=dimethyl sulfoxide
TEA=triethylamine
TFA=trifluoroacetic acid
THF=tetrahydrofuran
KOH=potassium hydroxide
$K_2CO_3$=potassium carbonate
$POCl_3$=phosphorous oxychloride
KOtBu=potassium t-butoxide
HOBt=1-hydroxybenzotriazole hydrate
NaH=sodium hydride
NaOH=sodium hydroxide
$Na_2S_2O_3$=sodium thiosulfate
Pd=palladium
min.=minute(s)
L=liter
mL=milliliter
μL=microliter
g=gram(s)
mg=milligram(s)
mol=moles
mmol=millimole(s)
meq=milliequivalent
RT=room temperature
ret. t.=HPLC retention time (minutes)
ret. Time=HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point The following Examples illustrate embodiments of the invention and are not intended to limit the scope of the claims. In the following Examples, anhydrous reactions were performed under an atmosphere of nitrogen or argon using either commercially available dry solvents or freshly distilled solvents. Reactions which refer to heating by microwave irradiation were performed on a Smith Synthesizer™ capable of generating reaction temperatures between 60 and 250° C., and pressures of 0-290 pounds per square inch (PSI). Column chromatography was performed using EM Science silica gel 60 with the designated solvent system as eluant. HPLC purification was conducted using a Shimadzu LC8A with YMC S5 ODS or xTerra MS $C_{18}$ columns. HPLC purity determinations were done using either an HP 1090 DR5 with a diode array detector and a Waters Nova-Pak $C_{18}$ column, or a Shimadzu LC-10AS with a SPD-10AV UV-V detector and Waters xTerra $C_{18}$ column. Melting points were determined in an open capillary tube with a Thomas-Hoover melting point apparatus.

$^1$H-NMR spectra were recorded in DMSO (δ=2.50 ppm) using a 500 MHZ instrument (unless otherwise stated) and chemical shifts are expressed in parts per million (ppm or δ) with the solvent in use as an internal standard. Coupling constants are given in Hertz, and multiplets are designated as follows: singlet (s), doublet (d), triplet (t), quartet (q), multiplet (m), broad (br), and apparent (app).

Low resolution mass spectra were determined with a Finnigan Matt TSQ-7000 or SSQ-700, or with a Shimadzu LC-10AS coupled with Waters Micromass ZQ. HRMS were determined with a Finnigan Matt 900.

PREPARATION OF INTERMEDIATES

Ethyl 2-methylthio-4-imidazole carboxylate, III

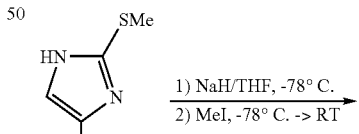

To a mixture of ethyl 2-mercapto-4-imidazole carboxylate (II) (49.82 g, 289 mmol) and $K_2CO_3$ (79.92 g, 579 mmol) in DMF (1500 mL) was added MeI (18.55 mL, 298 mmol) at room temperature, with stirring. After 18 hrs, it was filtered. The filtrate was concentrated under high vacuum to remove DMF. The residue was then filtered through a silica gel pad with EtOAc, and concentrated. PhMe (200 mL) was then added, followed by addition of Hexanes (1000 mL), precipitating III (50.5 g, 94%) as a yellow solid. $^1$H NMR (CDCl$_3$, 400 MHz): 7.69 (s, 1H), 4.35 (q, J=7.1 Hz, 2H), 2.67 (s, 3H), 1.35 (t, J=7.1 Hz, 3H).

Methyl 1-methyl-2-methylthio-4-imidazolecarboxylate, V

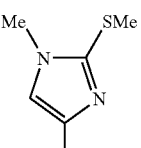 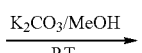

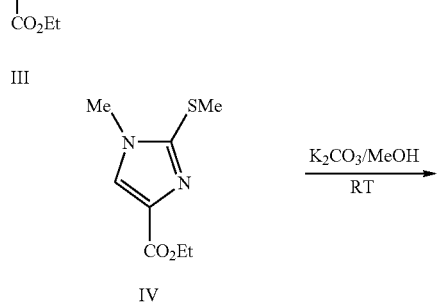

-continued

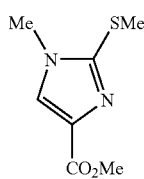

V

To a solution of III (50.5 g, 266 mmol) in THF (anhydrous, 1000 mL) was added NaH (60%, 14.3 g) at −78° C. After 1 h, MeI (18.5 mL, 297 mmol) was added. The mixture was then gradually warmed to 0° C. Upon completion of the reaction, filtration followed by concentration provided a residue, which was then dissolved in EtOAc/CHCl$_3$ (1500 mL, 2:1) and filtered to remove the solid. The filtrate was concentrated to give ethyl 1-methyl-2-methylthio-4-imidazolecarboxylate, IV, which was dissolved in MeOH (1000 mL) and stirred in the presence of K$_2$CO$_3$ (10 g). After 3 days, it was filtered and the MeOH was removed under vacuum. The residue was passed through a silica gel pad with EtOAc, furnishing compound V (methyl 1-methyl-2-methylthio-4-imidazole-carboxylate) (35.2 g, 67%) as a solid. $^1$H NMR (CDCl$_3$, 400 MHz): 7.48 (s, 1H), 3.74 (s, 3H), 3.50 (s, 3H), 2.54 (s, 3H); ESI m/z=187.05 [(M+H)$^+$; calcd for C$_7$H$_{11}$N$_2$O$_2$S: 187.05]

Alternatively, compound V can be prepared according to the following procedure:

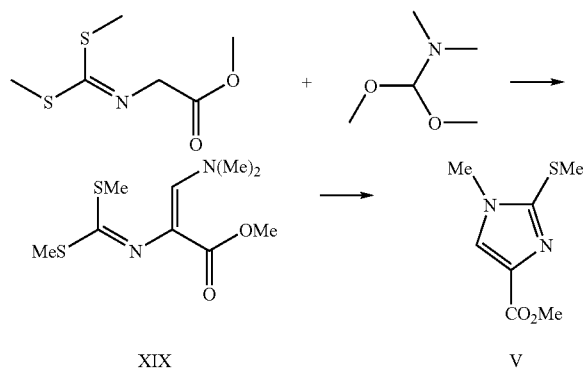

2-[[Bis(methylthio)methylene]amino]-3-(dimethylamino)-2-propenoic acid, methyl ester, XIX

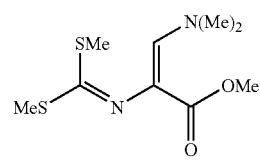

XIX

Commercially available N-[Bis(methylthio)methylene] glycine methyl ester (5.06 g, 26.18 mmol) and N,N-Dimethylformamide dimethyl acetal (4.03 g, 31.41 mmol) were dissolved in N,N-dimethylformamide (10 mL) and heated to reflux under nitrogen for 4.5 h. The solvent was removed under reduced pressure and the product solidified (6.44 g, 99%) after storage at room temperature under high vacuum over night. $^1$H NMR (CDCl$_3$, 400 MHz): δ 6.96 (s, 1H); 3.68 (s, 3H); 2.95 (s, 6H); 2.53 (s, 3H); 2.49 (s, 3H).

Methyl 1-methyl-2-methylthio-4-imidazolecarboxylate, V

XIX (8.29 g, 33.39 mmol) and methylamine hydrochloride (2.71 g, 40.07 mmol) were added to methanol (150 mL) and heated at reflux for 32 h. The reaction mixture was cooled and concentrated with silica gel (~20 g). The mixture was placed on top of a silica gel column and the product eluted with 90% ethyl acetate 10% heptane. Concentration of the appropriate fractions provided 4.13 g (66%) of the title product as a yellow solid. LCMS (10% MeOH, 90% H20, 0.1% TFA to 90% MeOH, 10% H$_2$O, 0.1% TFA, 2 minute gradient with a Phenomenex S5 column 4.6×30 mm produced a retention time of 0.56 minutes, and a [M+H]$^+$ m/z=187.16.

Methyl 1-methyl-2-methylthio-5-chloro-4-imidazolecarboxylate, VI

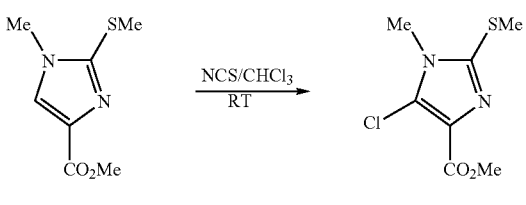

V   VI

A mixture of V (35.2 g, 189 mmol) and NCS (26.5 g, 198 mmol) was stirred in CH$_2$Cl$_2$ (1000 mL) at room temperature. After 18 hrs, concentration followed by extractive workup with EtOAc/H$_2$O and filtration through a silica gel pad with EtOAc/Hex (50:50) provided compound VI (methyl 1-methyl-2-methylthio-5-chloro-4-imidazolecarboxylate) (39.8 g, 95%) as a solid. $^1$H NMR (CDCl$_3$, 400 MHz): 3.94 (s, 3H), 3.57 (s, 3H), 2.70 (s, 3H); ESI m/z=243.67 [(M+Na)$^+$; calcd for C$_7$H$_9$ClN$_2$O$_2$S+Na: 243.00]

Methyl 1-methyl-2-methanesulfonyl-5-chloro-4-imidazolecarboxylate, VII

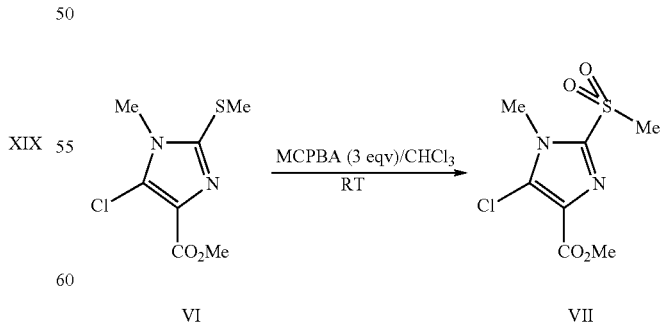

VI   VII

A mixture of VI (39.8 g, 180 mmol) and MCPBA (93.4 g) in CH$_2$Cl$_2$ (1000 mL) was stirred at room temperature for 6 h. NEt$_3$ (100 mL) was added to neutralize the acid, followed by addition of MgSO$_4$ to remove H$_2$O. It was then passed through a silica gel pad with EtOAc, furnishing compound VII (methyl 1-methyl-2-methanesulfonyl-5-chloro-4-imidazolecarboxylate) (38.1 g, 84%) as a white solid. $^1$H NMR (CDCl$_3$, 400 MHz): 3.89 (s, 3H), 3.87 (s, 3H), 3.40 (s, 3H); ESI m/z=253.06 [(M+H)$^+$; calcd for C$_7$H$_9$ClN$_2$O$_4$S+H: 253.00]

1-Methyl-2-methanesulfonyl-7-phenyl-4H-pyrazolo[5,1-b]purin-4-one, IX

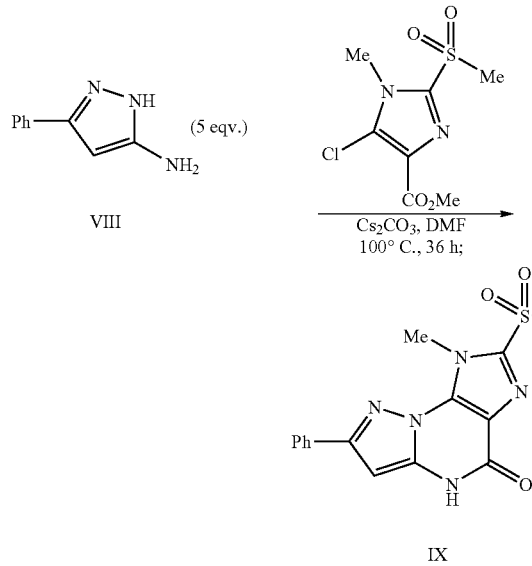

A mixture of 5-amino-3-phenylpyrazole (1.4244 g, 5.58 mmol), VIII, and VII (1.0839 g, 4.29 mmol) was stirred vigorously at the presence of Cs$_2$CO$_3$ (5.591 g, 17.16 mmol) in DMF (anhydrous, 43 mL) at 100° C. After 30 h, it was filtered and the filtrate was concentrated under high vacuum to remove DMF. The residue was treated with pH 7 buffer solution (50 mL), then carefully neutralized with 1.0 N HCl. The precipitate was filtered and washed with H$_2$O and EtOAc, providing IX (525.8 mg, 36%) as a white solid. $^1$H NMR (DMSO, 400 MHz): 12.3 (s, 1H), 7.97 (d, J=7.51 Hz, 2H), 7.49 (t, J=7.51 Hz, 2H), 7.42 (t, J=7.51 Hz, 1H), 6.46 (s, 1H), 3.55 (s, 3H); ESI m/z=344.03 [(M+H)$^+$; calcd for C$_{15}$H$_{13}$N$_5$O$_3$S+H: 344.08]

1-Methyl-7-phenyl-4H-pyrazolo[5,1-b]purin-4-one, X

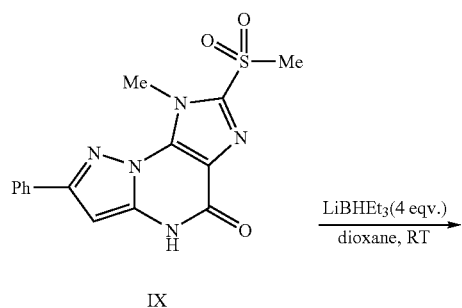

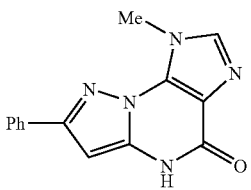

A solution of IX (525.8 mg, 1.53 mmol) in dioxane (anhydrous, 30 mL) was treated with LiBHEt$_3$ (1.0 M/THF, 6.1 mL) at room temperature. After 3 h, it was carefully quenched with MeOH and concentrated. The residue was treated with pH 7 buffer solution (40 mL), then neutralized with 1.0 N HCl. The precipitate was filtered and washed with H$_2$O, providing compound X (385.4 mg, 95%) as a white solid. $^1$H NMR (DMSO, 400 MHz): 12.03 (s, 1H), 7.95 (d, J=7.10 Hz, 2H), 7.92 (s, 1H), 7.47 (t, J=7.09 Hz, 2H), 7.40 (t, J=7.33 Hz, 1H), 6.38 (s, 1H), 4.20 (s, 3H); ESI m/z=266.08 [(M+H)$^+$; calcd for C$_{14}$H$_{11}$N$_5$O+H: 266.10]

1-Amino-5-tri-isopropylsilyloxypyrazole, XIII

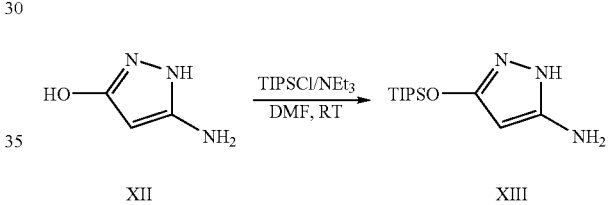

To a mixture of XII (29.03 g, 293 mmol) and NEt$_3$ (78 mL, 572 mmol) in DMF (500 mL) was added TIPSCl (53.8 g, 279 mmol) at 60° C. After 3 days, DMF was removed under high vacuum; the residue was worked up with EtOAc/H$_2$O. Filtration through a silica gel pad with a gradient of EtOAc/Hex (30:70 to 100%) furnished compound XIII (42.7 g, 57%) as a semi-solid. $^1$H NMR (DMSO, 400 MHz): 10.27 (s, 1H), 4.85 (s, 1H), 4.64 (s, 1H), 1.21 (m, 3H), 1.05 (d, J=7.34 Hz, 18H); ESI m/z=256.25 [(M+H)$^+$; calcd for C$_{12}$H$_{25}$N$_3$OSi+H: 256.18]

1-Methyl-2-methanesulfonyl-7-tri-isopropylsilyloxy-4H-pyrazolo[5,1-b]purin-4-one, XIV

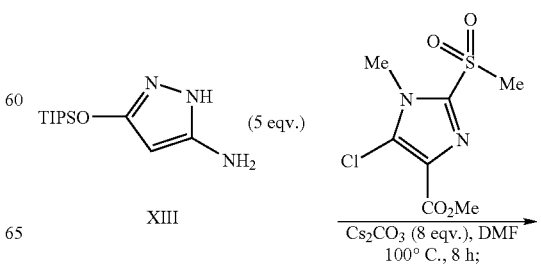

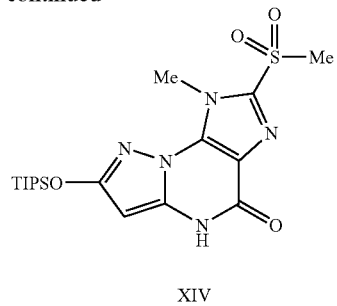

A mixture of XIII (27.67 g, 108 mmol) and VII (5.4739 g, 21.7 mmol) was stirred in the presence of Cs$_2$CO$_3$ (56.5 g, 173 mmol) in DMF (anhydrous, 400 mL) at 100° C. under N$_2$. After 8 h, it was cooled, filtered, and concentrated under high vacuum to remove DMF. The residue was treated with pH 7 buffer solution (200 mL) and CHCl$_3$ (1000 mL), then carefully neutralized with 1.0 N HCl under stirring. The CHCl$_3$ layer was further washed with H$_2$O (250 mL) and dried over MgSO$_4$. Filtration and concentration provided an oily residue, which was immediately treated with hexanes (500 mL) precipitating a white solid composing a 1:1 mixture of XIII and XIV. Flash chromatography with EtOAc/CH$_2$Cl$_2$ (1:5) on silica gel gave compound XIV (4.7337 g, 50%) as a white solid. $^1$H NMR (DMSO, 400 MHz): 12.08 (s, 1H), 5.41 (s, 1H), 4.30 (s, 1H), 3.49 (s, 1H), 1.33 (m, 3H), 1.10 (d, J=7.58 Hz, 18H); ESI m/z=440.12 [(M+H)$^+$; calcd for C$_{18}$H$_{29}$N$_5$O$_4$SSi+H: 440.18]

1-Methyl-7-tri-isopropylsilyloxy-4H-pyrazolo[5,1-b]purin-4-one, XV

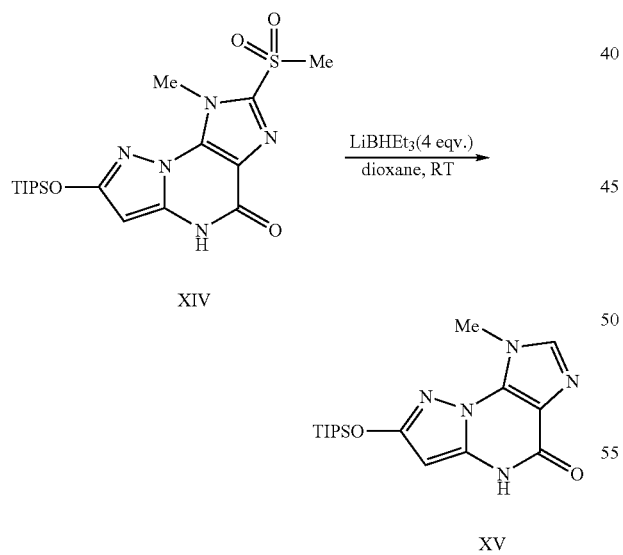

A solution of XIV (8.3 g, 18.9 mmol) in anhydrous dioxane (200 mL) was treated with LiBHEt$_3$ (1.0 M/THF, 76 mL) at room temperature. After 2 h, CH$_2$Cl$_2$ (400 mL) was added, followed by careful addition of pH 7 buffer solution (400 mL). The aqueous layer was then neutralized with 1.0 N HCl. The CH$_2$Cl$_2$ layer was dried over MgSO$_4$, filtered and concentrated. The solid residue was then washed with hexanes, providing compound XV (6.689 g, 98%) as a white solid. $^1$H NMR (DMSO, 400 MHz): 11.75 (s, 1H), 7.79 (s, 1H), 5.32 (s, 1H), 4.00 (s, 3H), 1.32 (m, 3H), 1.10 (d, J=7.34 Hz, 18H); ESI m/z=362.21 [(M+H)$^+$; calcd for C$_{17}$H$_{27}$N$_5$O$_2$Si+H: 362.20]

1-Methyl-7-hydroxy-4H-pyrazolo[5,1-b]purin-4-one, XVI

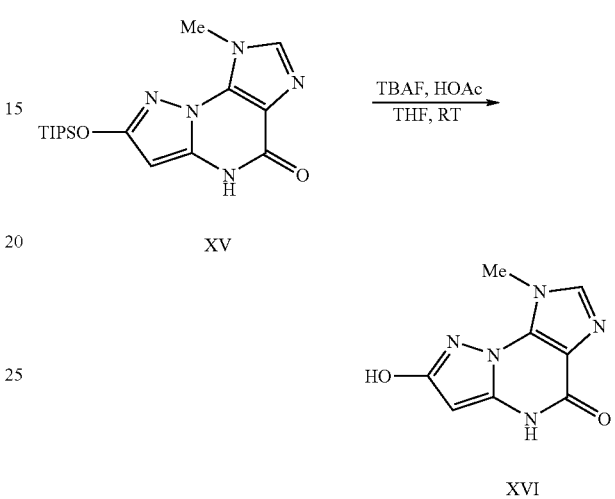

A solution of XV (5.87 g, 22.1 mmol) in THF/HOAc (16:1, 170 mL) was treated with n-Bu$_4$NF (1.0 M/THF, 32.5 mL) and stirred at room temperature for 4 h. The white precipitate was filtered and washed with CH$_2$Cl$_2$, furnishing compound XVI (3.09 g, 92%) as a white solid. $^1$H NMR (DMSO, 400 MHz): 11.66 (s, 1H), 10.71 (s, 1H), 7.79 9s, 1H), 5.21 (s, 1H), 5.0 (br s, 1H), 4.20 (s, 3H); ESI m/z=206.04 [(M+H)$^+$; calcd for C$_8$H$_7$N$_5$O$_2$+H: 206.07]

1-Methyl-4-methylamino-7-trifluoromethanesulfonyloxy-4H-pyrazolo[5,1-b]purin-4-one, XVII

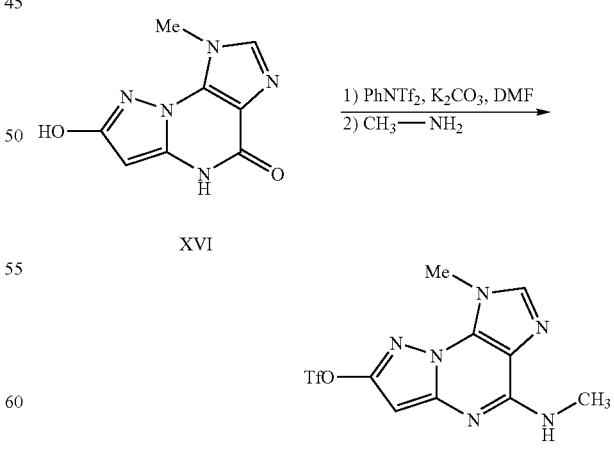

Compound XVII was prepared from compound XVI according to the above scheme.

1-Methyl-4-cyclopropylamino-7-trifluoromethane-
sulfonyloxy-4H-pyrazolo[5,1-b]purin-4-one, XVIII

EXAMPLE 1

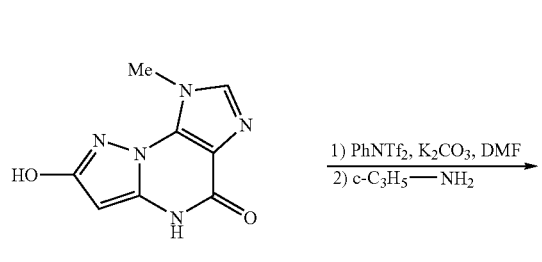

XVI

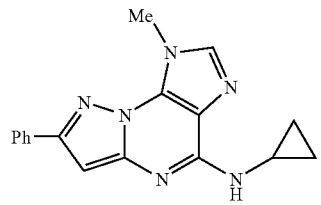

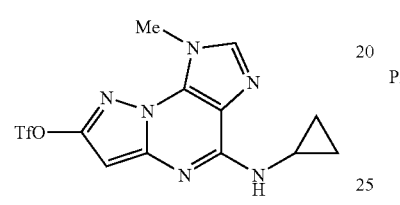

XVIII

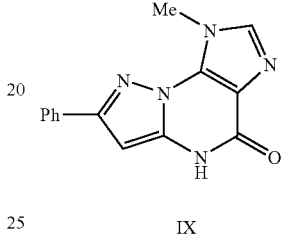

IX

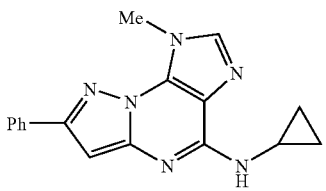

A mixture of 11 (2.3839 g, 11.6 mmol) and $K_2CO_3$ (6.43 g, 46.5 mmol) in DMF (100 mL) was treated with N-Phenyl trifluoromethanesulfonimide (12.4595 g, 34.9 mmol) at room temperature for 5 h. Cyclopropylamine (6.6 mL, 95.2 mmol) was then added, and the mixture was further stirred for another 2 h at room temperature. The solid was filtered out and the filtrate was concentrated under high vacuum to remove DMF. The residue was subsequently dissolved with EtOAc (200 mL), washed with $H_2O$ (5×100 mL), and dried over $MgSO_4$. Flash chromatography (EtOAc/Hexanes, 70:30) provided compound 12 (3.028 g, 69%) as a white solid. $^1$H NMR (DMSO, 400 MHz): 8.09 (d, J=3.42 Hz, 1H), 8.02 (s, 1H), 6.29 (s, 1H), 4.09 (s, 3H), 2.96 (m, 1H); 0.73 (m, 2H), 0.65 (m, 2H); ESI m/z=377.00 [(M+H)$^+$; calcd for $C_{12}H_{11}F_3N_6O_3S$+H: 377.06]

A mixture of IX (13.2 mg, 0.0498 mmol) and $K_2CO_3$ (20.6 mg, 0.149 mmol) in DMF (1.0 mL) was treated with N-phenyl trifluoromethanesulfonimide (35.6 mg, 0.0997 mmol) at room temperature for 5 h. Cyclopropylamine (6.6 mL, 95.2 mmol) was then added, and the mixture was further stirred for another 2 h at room temperature. Extractive EtOAc/$H_2O$ workup followed by flash chromatography (EtOAc/Hexanes, 70:30) provided the title compound (9.1 mg, 60%) as a white solid. $^1$H NMR (d-MeOD, 400 MHz): 7.89 (d, J=7.51 Hz, 2H), 7.72 (s, 1H), 7.39 (t, J=7.51 Hz, 2H), 7.31 (t, J=7.51 Hz, 1H), 6.51 (s, 1H), 4.25 (s, 3H), 2.87 (m, 1H), 0.87 (m, 2H), 0.63 (m, 1H); ESI m/z=305.13 [(M+H)$^+$; calcd for $C_{17}H_{16}N_6$+H: 305.15]

By the same method, using commercially available amines, the following other R$^4$ analogs were prepared:

| Example # | Structure | ESI m/z | $^1$H NMR (Solvent, 400 MHz) |
|---|---|---|---|
| 2 | 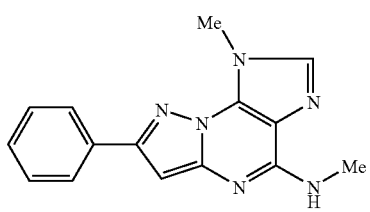 | 279.07 | d-MeOD: 7.92 (d, J=8.56 Hz, 2H), 7.77 (s, 1H), 7.40 (t, J=8.32 Hz, 2H), 7.32 (t, J= 7.33 Hz, 1H), 6.49 (s, 1H), 4.29 (s, 3H), 3.07 (s, 3H) |

-continued

| Example # | Structure | ESI m/z | ¹H NMR (Solvent, 400 MHz) |
|---|---|---|---|
| 3 | 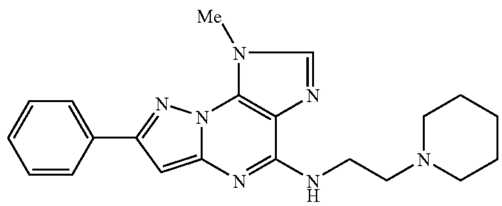 | | d-CDCl3: 7.92 (d, J=7.09 Hz, 2H), 7.45 (s, 1H), 7.41 (t, J=7.58 Hz, 2H), 7.32 (t, J=7.34 Hz, 1H), 6.51 (s, 1H), 6.33 (br s, 1H), 4.29 (s, 3H), 3.71 (m, 2H), 2.65 (t, J=6.12 Hz, 2H), 2.47 (m, 4H), 1.62 (m, 4H), 1.45 (m, 2H) |
| 4 | 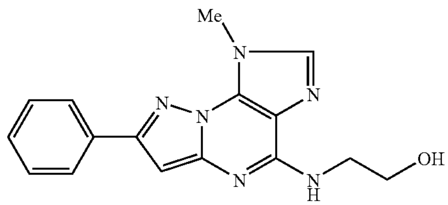 | | d-DMSO: 7.97 (s, 1H), 7.96 (d, J=6.61 Hz, 2H), 7.45 (t, J=7.34 Hz, 2H), 7.38-7.34 (m, 2H), 6.60 (s, 1H), 4.81 (t, J=5.38 Hz, 1H), 4.26 (s, 3H), 3.61 (t, J=5.62 Hz, 2H), 3.56 (t, J=5.62 Hz, 2H) |
| 5 | 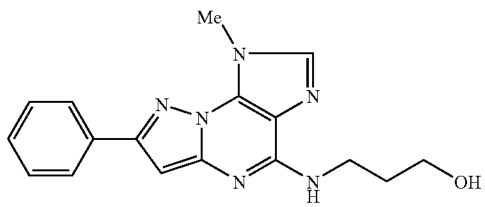 | 323.17 | d-DMSO: 7.97-7.95 (m, 3H), 7.53 (t, J=5.38 Hz, 1H), 7.45 (t, J=7.34 Hz, 2H), 7.36 (tt, J=7.34, 1.22 Hz, 1H), 6.60 (s, 1H), 7.59 (t, J=5.14 Hz, 1H), 4.25 (s, 3H), 3.56-3.49 (m, 4H), 1.78 (quintet, J=6.60 Hz, 2H) |
| 6 | 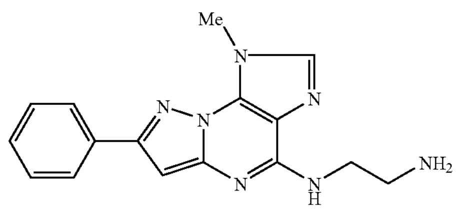 | | d-MeOD: 7.94 (d, J=7.09 Hz, 2H), 7.85 (s, 1H), 7.41 (t, J=7.33 Hz, 2H), 7.34 (t, J=7.33 Hz, 1H), 6.56 (s, 1H), 4.33 (s, 3H), 3.88-3.84 (m, 2H), 3.28-3.23 (m, 2H) |
| 7 | 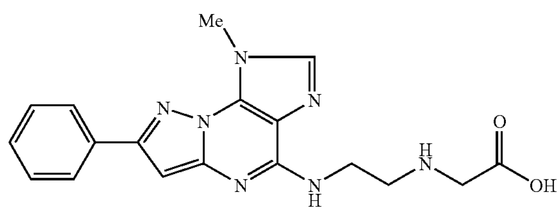 | 366.09 | d-MeOD: 7.93 (d, J=7.09 Hz, 2H), 7.75 (s, 1H), 7.40 (t, J=7.33 Hz, 2H), 7.32 (t, J=7.58 Hz, 1H), 6.53 (s, 1H), 4.27 (s, 3H), 3.73 (t, J=5.87 Hz, 2H), 3.32 (s, 2H), 3.03 (t, J=5.87 Hz, 2H) |
| 8 | 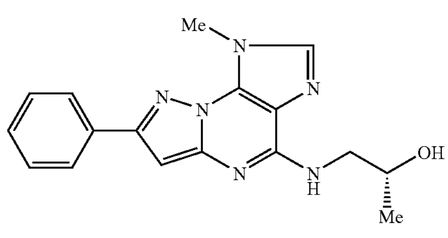 | 349.21 | d-MeOD: 7.89-7.86 (m, 3H), 7.44-7.34 (m, 3H), 6.60 (s, 1H), 4.25 (s, 3H), 4.10 (m, 1H), 3.60 (br s, 1H), 3.54 (br s, 1H), 1.29 (d, J=6.12 Hz, 3H) |
| 9 | 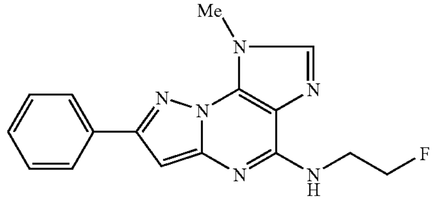 | 311.14 | |

-continued
| Example # | Structure | ESI m/z | ¹H NMR (Solvent, 400 MHz) |
|---|---|---|---|
| 10 | 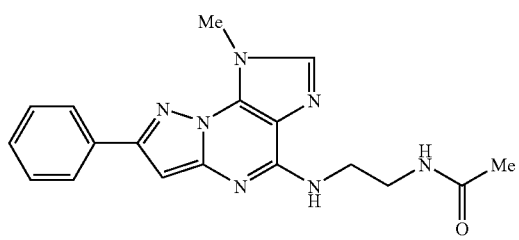 | 350.12 | d-MeOD: 7.89 (d, J=8.31 Hz, 2H), 7.84 (s, 1H), 7.43-7.34 (m, 3H), 6.61 (s, 1H), 4.24 (s, 3H), 3.68 (br s, 2H), 3.50 (t, J=6.11 Hz, 2H), 1.97 (s, 3H) |
| 11 | 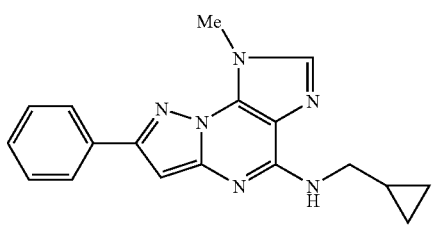 | 319.12 | d-MeOD: 7.91 (d, J=7.10 Hz, 2H), 7.90 (s, 1H), 7.43 (t, J=7.09 Hz, 2H), 7.37 (t, J=7.09 Hz, 1H), 6.62 (s, 1H), 4.30 (s, 3H), 3.46 (br s, 2H), 1.24 (m, 1H), 0.66-0.62 (m, 2H), 0.40-0.36 (m, 2H) |
| 12 | 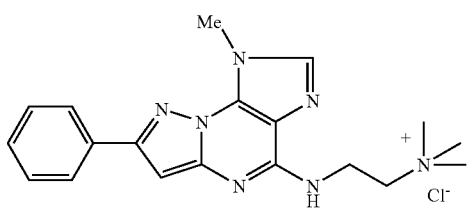 | 350.16 | d-MeOD: 7.94 (d, J=7.09 Hz, 2H), 7.85 (s, 1H), 7.42 (t, J=7.09 Hz, 2H), 7.34 (t, J=7.34 Hz, 1H), 6.57 (s, 1H), 4.33 (s, 3H), 4.10 (br s, 2H), 3.69 (t, J=6.60 Hz, 2H), 3.26 (s, 9H) |
| 13 | 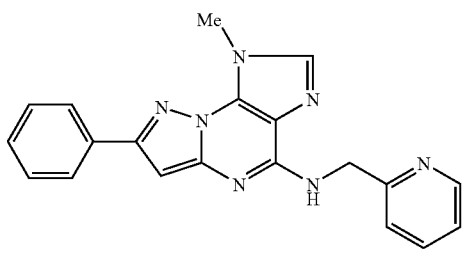 | 356.12 | d-MeOD: 8.65 (d, J=5.62 Hz, 1H), 8.30 (td, J=8.07, 1.47 Hz, 1H), 7.91 (d, J=7.83 Hz, 2H), 7.88 (s, 1H), 7.73 (t, J=6.60 Hz, 1H), 7.40 (t, J=7.83 Hz, 2H), 7.32 (t, J=7.58 Hz, 1H), 6.47 (s, 1H), 5.05 (s, 2H), 4.34 (s, 3H) |
| 14 | 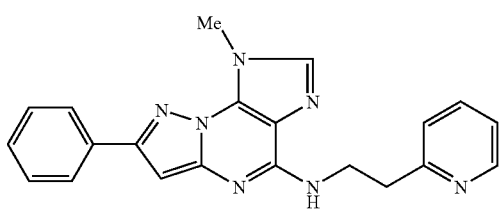 | 370.16 | d-MeOD: 8.69 (d, J=6.11, 1H), 8.38 (td, J=7.83, 1.71 Hz, 1H), 7.96 (d, J=8.07 Hz, 1H), 7.93 (d, J=7.10 Hz, 2H), 7.82 (s, 1H), 7.78 (ddd, J=7.33, 5.87, 0.98 Hz, 1H), 7.42 (t, J=7.58 Hz, 2H), 7.34 (tt, J=7.58, 1.22 Hz, 1H), 6.44 (s, 1H), 4.30 (s, 3H), 4.06 (t, J=6.11 Hz, 2H), 3.42 (t, J=6.36 Hz, 2H) |

EXAMPLE 15

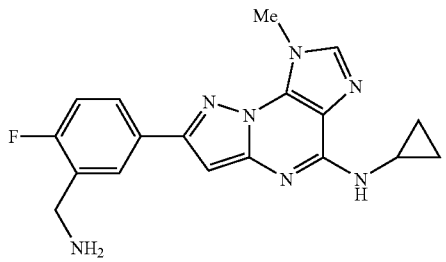

1-Methyl-4-cyclopropylamino-7-(3'-acetamidomethyl-4'-fluorophenyl-pyrazolo[5,1-b]purine A. 3-Aminomethyl-4-fluoro-1-trimethylstannylbenzene

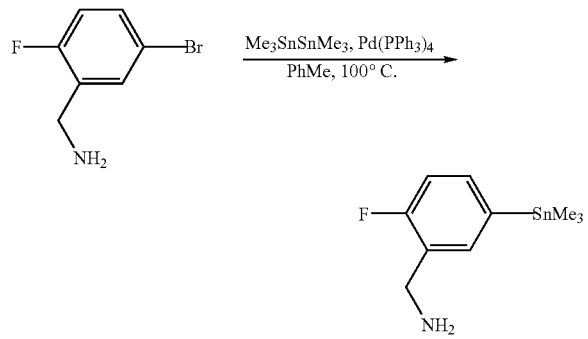

A mixture of 5-bromo-2-fluorobenzylamine (15.568 g, 76.3 mmol) and hexamethylditin (30 g, 91.6 mmol) was heated at 100° C. at the presence of Pd(PPh$_3$)$_4$ (3.0 g, 2.60 mmol) in toluene (400 mL). After 3 h, filtration through a silica gel plug with EtOAc provided a white solid. Further wash with saturated Na2CO3 furnished compound 16 (17.02 g, 77.5%) an oil. $^1$H NMR (CDCl$_3$, 400 MHz): 7.39 (d, J=8.34 Hz, 1H), 7.33 (t, J=5.83 Hz, 1H), 7.02 (dd, J=10.83, 7.91 Hz, 1H), 3.89 (s, 2H), 1.41 (s, 2H), 0.28 (s, 9H).

B. 1-Methyl-4-cyclopropylamino-7-(3'-acetamidomethyl-4'-fluorophenyl-pyrazolo[5,1-b]purine

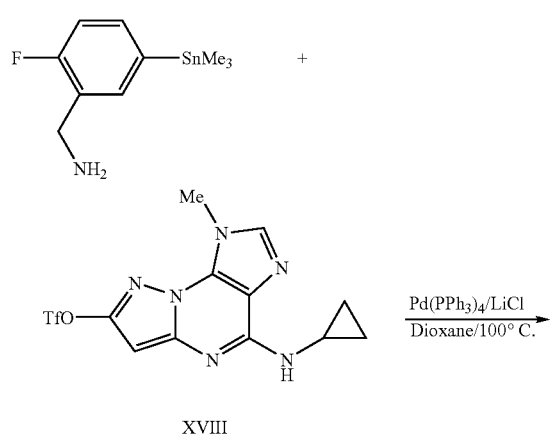

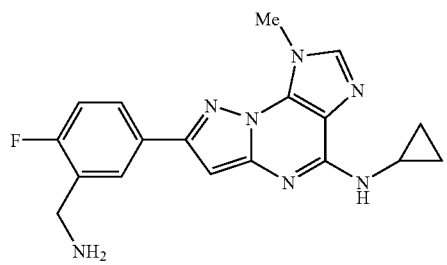

A mixture of XVIII (514.8 mg, 1.37 mmol), 3-aminomethyl-4-fluoro-1-trimethylstannylbenzene (787.8 mg, 2.74 mmol), Pd(PPh$_3$)$_4$ (158.1 mg, 0.137 mmol) and LiCl (410.4 mg, 4.10 mmol) was heated at 100° C. in dioxane (14 mL). After 7 h, it was cooled down and EtOAc was added (30 mL). The precipitate was filtered and sequentially washed with saturated Na$_2$CO$_3$, H$_2$O and EtOAc. Further purification by flash chromatography (MeOH/CH$_2$Cl$_2$, 5%) furnished compound the title compound (191.8 mg, %) as a white solid. $^1$H NMR (d-DMSO, 400 MHz): 8.08 (dd, J=7.58, 2.20 Hz, 1H), 7.96 (s, 1H), 7.84 (ddd, J=7.83, 5.14, 2.20 Hz, 1H), 7.73 (d, J=4.16 Hz, 1H), 7.21 (dd, J=10.03, 8.56 Hz, 1H), 6.62 (s, 1H), 3.81 (3, 2H), 2.98 (m, 1H), 0.73 (m, 2H), 0.65 (m, 2H); ESI m/z=352.16 [(M+H)$^+$; calcd for C$_{18}$H$_{18}$FN$_7$+H: 352.17]

EXAMPLE 16

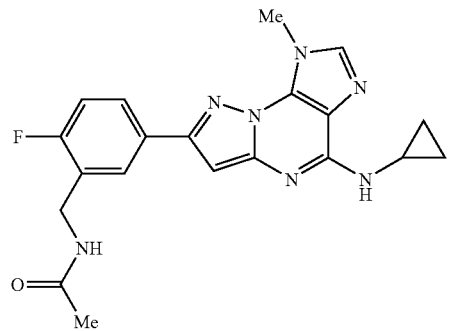

1-Methyl-4-cyclopropylamino-7-(3'-acetamidomethyl-4'-fluorophenyl)-pyrazolo[5,1-b]purine A. 3-Acetamidomethyl-4-fluoro-1-trimethylstannylbenzene

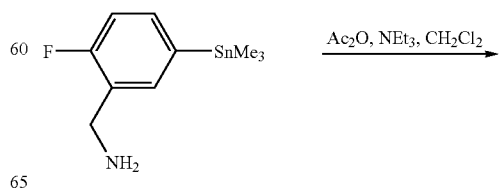

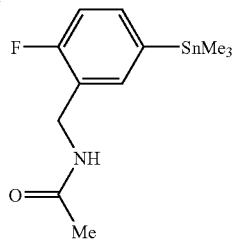

A mixture of 3-aminomethyl-4-fluoro-1-trimethylstannyl-benzene (505.4 mg, 1.76 mmol), Ac₂O (215.3 μL, 2.28 mmol) and NEt₃ (489 μL, 3.51 mmol) was stirred at room temperature in CH₂Cl₂ (18 mL). After 3 h, extractive EtOAc/H₂O workup followed by flash chromatography (EtOAc/Hexanes, 40:60) provided the title compound (422 mg, 73%) as an oil. ¹H NMR (DMSO, 400 MHz): 8.29 (br s, 1H), 7.41 (d, J=7.52 Hz, 1H), 7.45-7.30 (m, 1H), 7.14 (dd, J=10.9, 8.2 Hz, 1H), 4.27 (d, J=5.47 Hz, 2H), 1.85 (s, 3H), 0.26 (s, 9H).

B. 1-Methyl-4-cyclopropylamino-7-(3'-acetamidomethyl-4'-fluorophenyl)-pyrazolo[5,1-b]purine

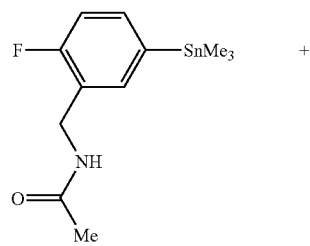

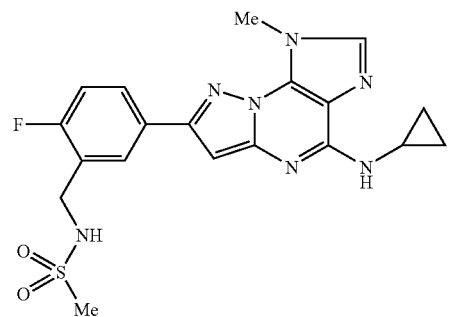

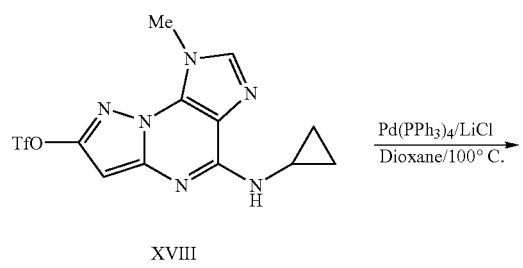

A mixture of XVIII (375.7 mg, 0.998 mmol), 3-acetamidomethyl-4-fluoro-1-trimethylstannylbenzene (575 mg, 1.75 mmol), Pd(PPh₃)₄ (115 mg, 0.0995 mmol) and LiCl (299.5 mg, 3.00 mmol) was heated at 100° C. in Dioxane (10 mL). After heating overnight, it was cooled down and EtOAc (30 mL) was added. The precipitate was filtered and sequentially washed with saturated Na₂CO₃, H₂O and EtOAc. Further purification by flash chromatography (MeOH/CH₂Cl₂, 5%) furnished compound tht title compound (170 mg, 43%) as a white solid. ¹H NMR (d-DMSO, 400 MHz): 8.39 (t, J=5.87 Hz, 1H), 7.96 (s, 1H), 7.91 (d, J=6.14 Hz, 1H), 7.87 (m, 1H), 7.73 (J=4.10 Hz, 1H), 7.26 (t, J=8.88 Hz, 1H), 6.60 (s, 1H), 4.35 (d, J=5.46 Hz, 2H), 4.26 (s, 3H), 2.97 (m, 1H), 1.90 (s, 3H), 0.72 (m, 2H), 0.65 (m, 2H); ESI m/z=394.25 [(M+H)⁺; calcd for C₂₀H₂₀FN₇O+H: 394.18]

EXAMPLE 17

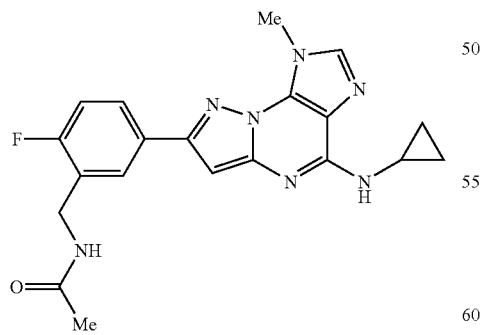

1-Methyl-4-cyclopropylamino-7-(4'-fluoro-3'-methanesulfonamidomethyl-phenyl)-pyrazolo[5,1-b]purine A. 3-Methanesulfonamidomethyl-4-fluoro-1-trimethylstannylbenzene

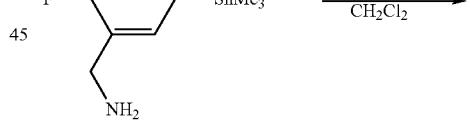

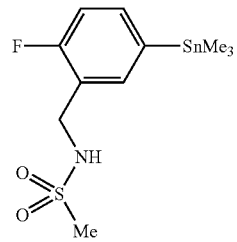

A mixture of 3-aminomethyl-4-fluoro-1-trimethylstannyl-benzene (507.9 mg, 1.76 mmol), ClSO₂Me (180.9 μL, 2.29 mmol) and NEt₃ (492 μL, 3.52 mmol) was stirred at room temperature in CH₂Cl₂ (18 mL). After 3 h, extractive EtOAc/H₂O workup followed by flash chromatography (EtOAc/Hexanes, 20:80) provided the title compound (342 mg, 53%) as an oil. ¹H NMR (CDCl₃, 400 MHz.

B. 1-Methyl-4-cyclopropylamino-7-(4'-fluoro-3'-methane-sulfonamidomethyl-phenyl)-pyrazolo[5,1-b]purine

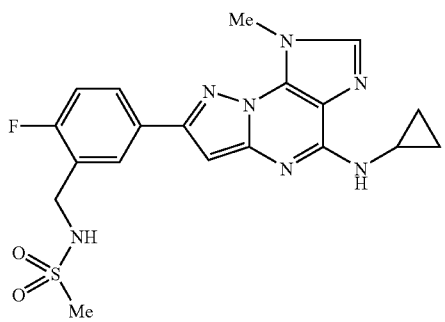

The title compound is prepared by the method of Example 16, part B from compound XVII and 3-methanesulfonami-domethyl-4-fluoro-1-trimethylstannylbenzene. ESI m/z=430.20 [(M+H)$^+$; calcd for $C_{19}H_{20}FN_7O_2S$+H: 430.15] 1H NMR d-DMSO: 8.07 (dd, J=7.33, 2.44 Hz, 1H), 7.97 (s, 1H), 7.91 (ddd, J=7.82, 4.40, 1.95 Hz, 1H), 7.74 (d, J=3.91 Hz, 1H), 7.64 (t, J=6.11 Hz, 1H), 7.30 (dd, J=10.07, 8.56 Hz, 1H), 6.61 (s, 1H), 4.28 (d, J=6.12 Hz, 1H), 4.26 (s, 3H), 2.99 (m, 1H), 2.94 (s, 3H), 0.73 (m, 2H), 0.65 (m, 2H).

EXAMPLE 18

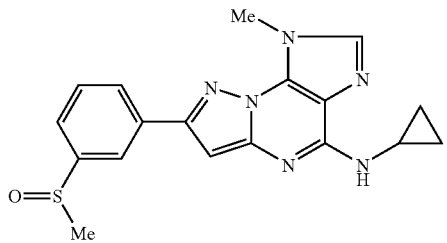

1-Methyl-4-cyclopropylamino-7-(3'methylsulfoxyl-phenyl)-pyrazolo[5,1-b]purine

A. 3-Bromophenyl methyl sulfoxide

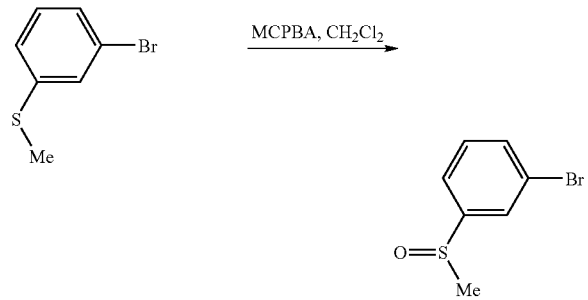

A mixture of 3-bromothioanisole (4.9687 g, 0.0245 mmol) and MCPBA (5.066 g, %) was stirred at room temperature. After 4 h, extractive EtOAc/H$_2$O workup followed by flash chromatography (EtOAc/Hexanes, 50:50) provided the title compound (3.725 g, 69%) as an oil. $^1$H NMR (DMSO, 400 MHz): 7.80 (br s, 1H), 7.61 (d, J=8.01 Hz, 1H), 7.53 (d, J=8.01 Hz, 1H), 7.39 (t, J=8.01 Hz, 1H), 2.72 (s, 3H).

B. 3-Trimethylstannylphenyl methyl sulfoxide

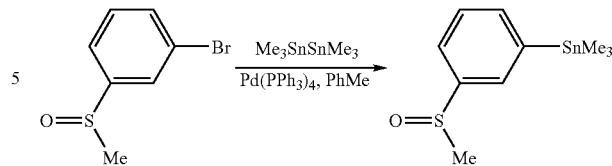

A mixture of compound 3-Bromophenyl methyl sulfoxide (3.7247 g, 17 mmol) and hexamethylditin (7.239 g, 22 mmol) was heated at 100° C. at the presence of Pd(PPh$_3$)$_4$ (982 mg, 0.85 mmol) in toluene (80 mL). After 3 h, flash chromatography (EtOAc/Hexanes, 50:50) provided the title compound (4.875 g, 94% yield) as an oil. $^1$H NMR (CDCl$_3$, 400 MHz): 7.75 (s, 1H), 7.61 (d, J=7.09 Hz, 1H), 7.54 (d, J=7.82 Hz, 1H), 7.46 (t, J=7.10 Hz, 1H), 2.72 (s, 3H), 0.32 (s, 9H).

C. 1-Methyl-4-cyclopropylamino-7-(3'methylsulfoxyl-phenyl)-pyrazolo[5,1-b]purine

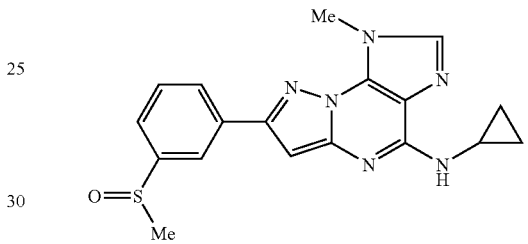

The title compound is prepared by the method of Example 16, part B from compound XVII and 3-trimethylstannylphenyl methyl sulfoxide. ESI m/z=367.22 [(M+H)$^+$; calcd for $C_{18}H_{18}N_6OS$+H: 367.13] 1H NMR d-MeOD: 8.25 (s, 1H), 8.08-8.06 (m, 1H), 7.74 (s, 1H), 7.62-7.61 (m, 2H), 6.59 (s, 1H), 4.28 (s, 3H), 2.91-2.86 (m, 1H), 2.85 (s, 3H), 0.89-0.85 (m, 2H), 0.66-0.62 (m, 2H).

EXAMPLE 19

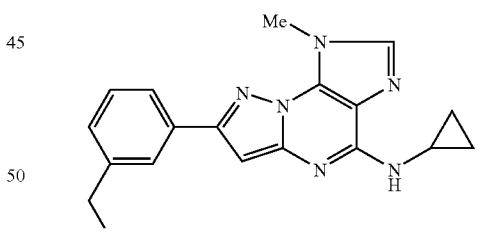

1-Methyl-4-cyclopropylamino-7-(3'-aminomethyl-phenyl)-pyrazolo[5,1-b]purine

A. (3-Aminomethylphenyl)trimethyl stannane

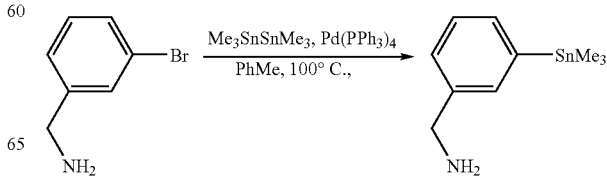

The title compound was prepared by the method of example 15, part A, from 3-bromo-benzylamine and hexamethyl-di-tin. $^1$H NMR (d-DMSO, 400 MHz): 7.43 (s, 1H), 7.32-7.26 (m, 3H), 3.72 (s, 2H), 1.71 (br s, 2H), 0.27 (s, 9H).

B. 1-Methyl-4-cyclopropylamino-7-(3'-aminomethyl-phenyl)-pyrazolo[5,1-b]purine

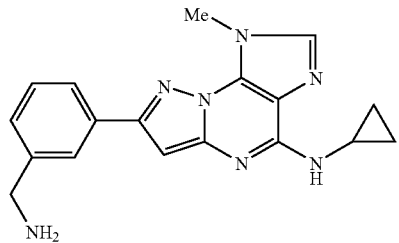

The title compound is prepared by the method of Example 16, part B from compound XVII and (3-aminomethylphenyl)trimethyl stannane. ESI m/z=334.23 [(M+H)$^+$; calcd for C$_{18}$H$_{19}$N$_7$+H: 334.18]. $^1$H NMR d-DMSO: 7.96-7.92 (m, 2H), 7.84-7.70 (m, 2H), 7.38 (t, J=7.58 Hz, 1H), 7.33 (s, 1H), 6.62 (s, 1H), 4.26 (s, 3H), 3.78 (s, 2H), 2.98 (m, 1H), 0.72 (m, 2H), 0.65 (m, 2H)

EXAMPLE 20

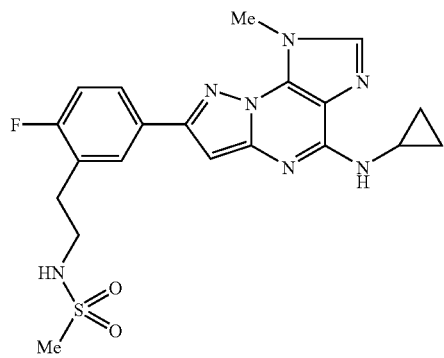

1-Methyl-4-cyclopropylamino-7-(4'-fluoro-3'(2"-methanesulfonamidoethyl)-phenyl)-pyrazolo[51-b]purine A. 3(2'-Aminoethyl)-4-fluorophenyl trimethylstannane

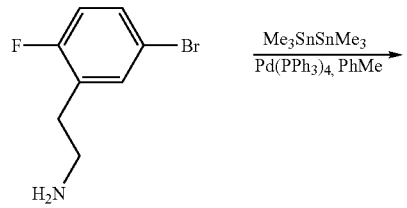

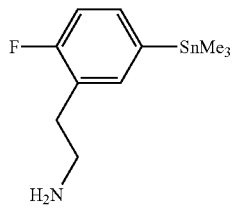

A mixture of 2(5'-bromo-2-fluorophenyl)ethylamine (376.0 mg, 1.72 mmol), Me$_3$SnSnMe$_3$ (847 mg, 2.59 mmol) and Pd(PPh$_3$)$_4$ (99.6 mg, 0.0862 mmol) in toluene (17 mL) was heated at 100° C. After 3 h, concentration and flash chromatography (EtOAc) followed by wash with sat. Na$_2$CO$_3$ provided the title compound (351 mg, 67%) as an oil. $^1$H NMR (CDCl$_3$, 400 MHz): 7.34-7.25 (m, 2H), 6.95 (dd, J=11.02, 8.48 Hz, 1H), 6.92 (br s, 2H), 3.23 (m, 2H), 3.11 (m, 2H), 0.25 (s, 9H).

B. 3(2'-Methanesulfonamidoethyl)-4-fluorophenyl trimethylstannane

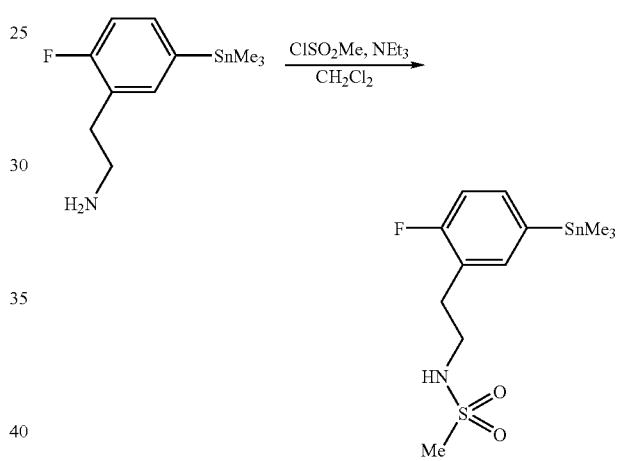

A mixture of 3(2'-aminoethyl)-4-fluorophenyl trimethylstannane (184.9 mg, 0.612 mmol), ClSO$_2$Me (62.8 μL, 0.796 mmol) and NEt$_3$ (171 μL, 1.22 mmol) was stirred in CH$_2$Cl$_2$ (6.0 mL) at room temperature. After 6 h, extractive workup with EtOAc/sat. Na$_2$CO$_3$ and flash chromatography (EtOAc/Hexanes, 20:80) provided the title compound (111.6 mg, %) as an oil.

C. 1-Methyl-4-cyclopropylamino-7-(4'-fluoro-3'(2"-methanesulfonamidoethyl)-phenyl)-pyrazolo[5,1-b]purine

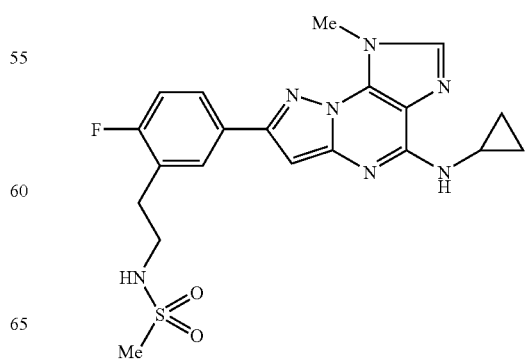

The title compound is prepared by the method of Example 16, part B from compound XVII and 3(2'-methanesulfonamidoethyl)-4-fluorophenyl trimethylstannane. ESI m/z=444.09 [(M+H)+; calcd for $C_{20}H_{22}FN_7O_2S$+H: 444.16]. $^1$H NMR d-MeOD: 7.91 (dd, J=7.09, 1.95 Hz, 1H), 7.86-7.82 (m, 1H), 7.80 (s, 1H), 7.13 (dd, J=9.79, 8.56 Hz, 1H), 6.55 (s, 1H), 4.32 (s, 3H), 3.36 (t, J=7.10 Hz, 2H), 2.96 (t, J=7.82 Hz, 2H), 2.92-2.89 (m, 1H), 2.85 (s, 3H), 0.91-0.86 (m, 2H), 0.67-0.63 (m, 2H)

EXAMPLE 21

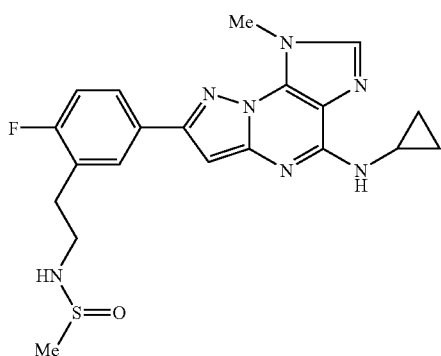

1-Methyl-4-cyclopropylamino-7-(4'-fluoro-3'(2''-acetamidoethyl)-phenyl)-pyrazolo[5,1-b]purine A. 3(2'-Acetamidoethyl)-4-fluorophenyl trimethylstannane

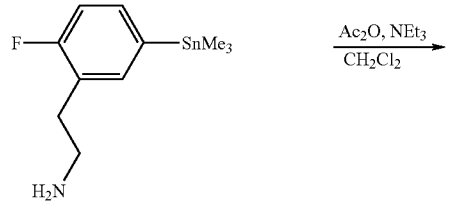

A mixture of 3(2'-aminoethyl)-4-fluorophenyl trimethylstannane (164.9 mg, 0.546 mmol), Ac$_2$O (67 μL, 0.710 mmol) and NEt$_3$ (152 μL, 1.09 mmol) was stirred in CH$_2$Cl$_2$ (6.0 mL) at room temperature. After 6 h, extractive workup with EtOAc/sat. Na$_2$CO$_3$ and flash chromatography (EtOAc/Hexanes, 20:80) provided the title compound (85.6 mg, %) as an oil.

B. 1-Methyl-4-cyclopropylamino-7-(4'-fluoro-3'(2''-acetamidoethyl)-phenyl)-pyrazolo[5,1-b]purine

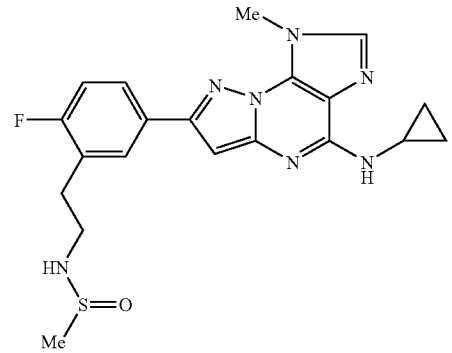

The title compound is prepared by the method of Example 16, part B, from compound XVIII and 3(2'-acetamidoethyl)-4-fluorophenyl trimethylstannane. ESI m/z=408.21 [(M+H)+; calcd for $C_{21}H_{22}FN_7O$+H: 408.19]. $^1$NMR d-MeOD: 7.85-7.81 (m, 2H), 7.79 (s, 1H), 7.11 (t, J=9.78, 8.56 Hz, 1H), 6.53 (s, 1H), 4.31 (s, 3H), 3.44 (t, J=7.34 Hz, 2H), 2.93-2.88 (m, 2H), 1.90 (s, 3H), 0.90-0.86 (m, 2H), 0.66-0.63 (m, 2H)

EXAMPLE 22

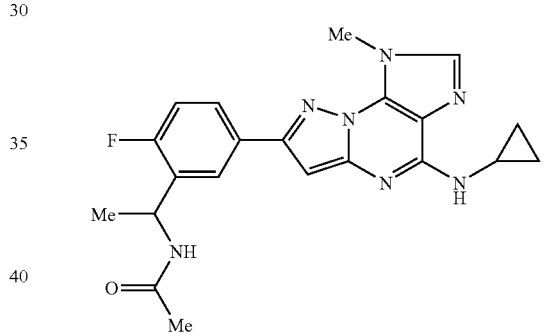

1-Methyl-4-cyclopropylamino-7-(4'-fluoro-3'(1''-acetamidoethyl)-phenyl)-pyrazolo[5,1-b]purine A. 1(2'-Fluoro-5'-bromo)phenylethanol

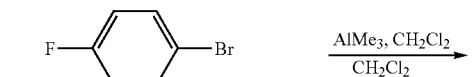

To a solution of 5-bromo-2-fluorobenaldehyde (5.43 g, 26.7 mmol) in CH$_2$Cl$_2$ (200 mL) was added dropwise AlMe$_3$ (2.0 M in PhMe, 16 mL) at −78° C. After 0.5 h, it was warmed to room temperature for another 0.5 h. The reaction was then quenched by slow addition of 1.0 N HCl. The organic layer was dried over MgSO$_4$ and filtered. Flash chromatography (EtOAc/Hexanes, 50:50) furnished the title compound (5.33 g, 91%) as an oil. $^1$H NMR (CDCl$_3$, 400 MHz): 7.63 (dd, J=6.60, 2.45 Hz, 1H), 7.33 (ddd, J=8.80, 4.65, 2.69 Hz, 1H), 6.90 (dd, J=9.78, 8.80 Hz, 1H), 5.15 (m, 1H), 1.92 (d, J=3.91 Hz, 1H), 1.49 (d, J=6.36 Hz, 3H).

B. N-(1(2'-fluoro-5-bromophenyl)ethyl)acetamide

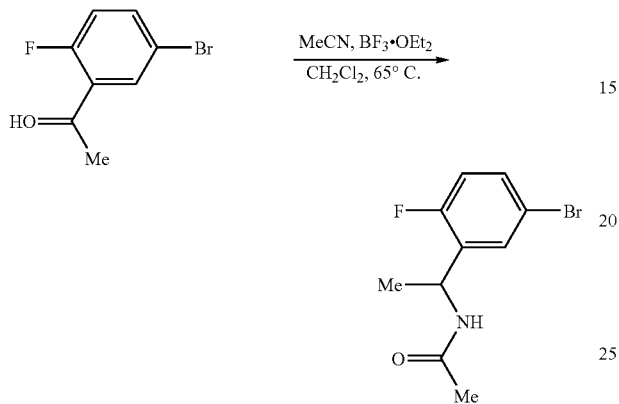

A solution of 1(2'-fluoro-5'-bromo)phenylethanol (1.725 g, 7.87 mmol) and MeCN (823 μL, 15.7 mmol) in CH$_2$Cl$_2$ (40 mL) was treated with BF$_3$.OEt$_2$ (998 μL, 7.87 mmol) was room temperature, then heated at 65° C. for 20 h. Normal extractive workup with saturated Na$_2$CO$_3$/EtOAc followed by flash chromatography (EtOAc/Hexanes, 50:50) provided the title compound (952.7 mg, % yield) as an oil. $^1$H NMR (CDCl$_3$, 400 MHz): 7.38 (dd, J=6.60, 2.45 Hz, 1H), 7.33 (ddd, J=8.56, 4.64, 2.44 Hz, 1H), 6.92 (dd, J=10.27, 8.56 Hz, 1H), 5.81 (br s, 1H), 5.21 (quintet, J=7.34 Hz, 1H), 1.99 (s, 3H), 1.46 (d, J=6.85 Hz, 3H).?

C. N-(1(2'-fluoro-5-trimethylstannylphenyl)ethyl)acetamide

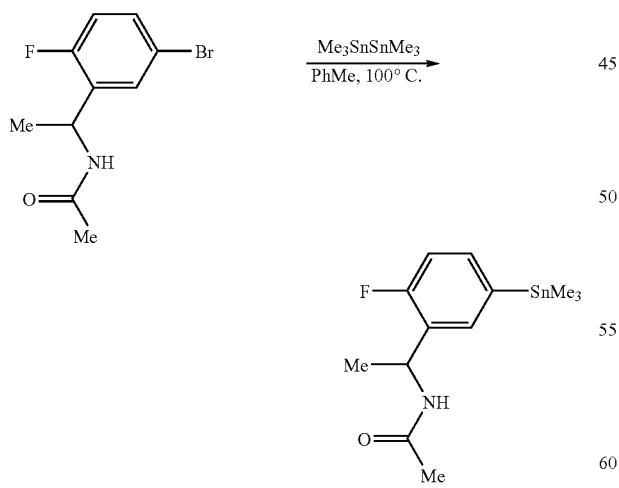

A mixture of N-(1(2'-fluoro-5-bromophenyl)ethyl)acetamide (952.7 mg, 3.66 mmol) and hexamethylditin (1.56 g, 4.76 mmol) was heated at 100° C. at the presence of Pd(PPh$_3$)$_4$ (211.7 mg, 0.183 mmol) in toluene (37 mL). After 3 h, flash chromatography (hexanes to EtOAc/hexanes=1:1) provided a white solid. Further wash with saturated Na$_2$CO$_3$ furnished the title compound (1.057 g, 77.5% yield) as an oil. $^1$H NMR (CDCl$_3$, 400 MHz): 7.41-7.28 (m, 1H), 7.34 (d, J=7.09 Hz, 1H), 7.02 (dd, J=11.24, 7.58 Hz, 1H), 5.97 (d, J=8.56 Hz, 1H), 5.24 (quintet, J=7.09 Hz, 1H), 1.58 (s, 3H), 1.49 (d, J=7.09 Hz, 3H), 0.27 (s, 9H).

D. 1-Methyl-4-cyclopropylamino-7-(4'-fluoro-3'(1''-acetamidoethyl)-phenyl)-pyrazolo[5,1-b]purine

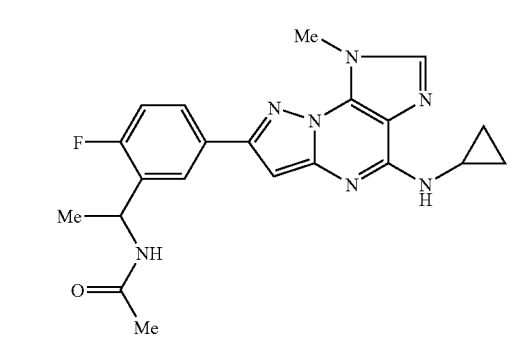

The title compound is prepared by the method of Example 16, part B, from compound XVIII and N-(1(2'-fluoro-5-trimethylstannylphenyl)ethyl)acetamide. ESI m/z=408.28 [(M+H)$^+$; calcd for C$_{21}$H$_{22}$FN$_7$O+H: 408.19]

EXAMPLE 23

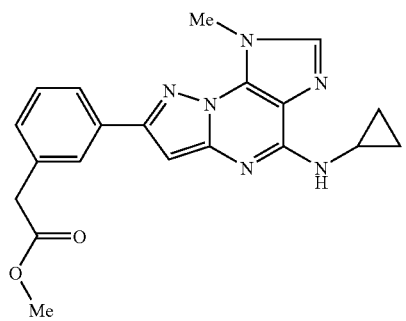

1-Methyl-4-cyclopropylamino-7-(3'-methoxycarbonylmethylphenyl)-pyrazolo[5,1-b]purine A. Methyl 3-trimethylstannylphenylacetate

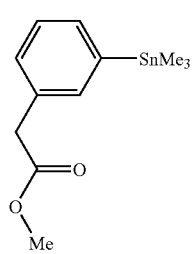

The title compound is prepared by the method of Example 15, part A, from methyl (3'-bromophenyl)acetate and hexamethyl-di-tin. $^1$NMR d-CDCl3: 7.41-7.23 (m, 4H), 3.70 (s, 3H), 3.62 (s, 2H), 0.29 (s, 9H)

B. 1-Methyl-4-cyclopropylamino-7-(3'-methoxycarbonylmethylphenyl)-pyrazolo[5,1-b]purine

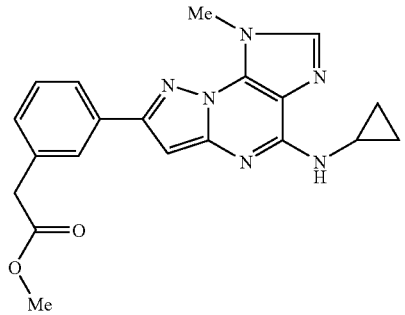

The title compound is prepared by the method of Example 16, part B, from compound XVIII and methyl 3-trimethylstannylphenylacetate. ESI m/z=377.12 [(M+H)$^+$; calcd for $C_{20}H_{20}N_6O_2$+H: 377.17]. $^1$NMR d-CDCl3: 7.83 (s, 1H), 7.80 (d, J=7.58 Hz, 1H), 7.41 (s, 1H), 7.37 (t, J=7.58 Hz, 1H), 7.25 (d, J=6.84 Hz, 1H), 6.59 (s, 1H), 5.92 (s, 1H), 4.28 (s, 3H), 3.69 (apparent s, 5H), 3.00 (m, 1H), 0.90 (m, 2H), 0.65 (m, 2H)

EXAMPLE 24

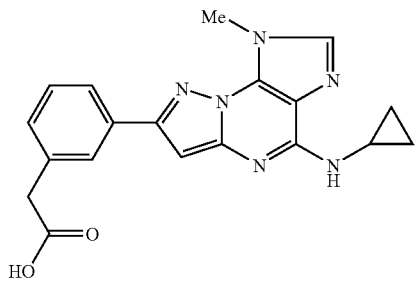

1-Methyl-4-cyclopropylamino-7-(3'-carboxymethylphenyl)-pyrazolo[5,1-b]purine

Example 24 was prepared from 23B through a standard hydrolysis. ESI m/z=363.11 [(M+H)$^+$; calcd for $C_{19}H_{18}N_6O_2$+H: 363.16]. $^1$NMR d-DMSO: 12.43 (s, 1H), 7.98 (s, 1H), 7.87 (s, 1H), 7.84 (d, J=8.07 Hz, 1H), 7.40 (t, J=7.58 HZ, 1H), 7.26 (d, J=7.83 Hz, 1H), 6.63 (s, 1H), 4.26 (s, 3H), 3.65 (s, 2H), 2.98 (m, 1H), 0.74 (m, 2H), 0.66 (m, 2H)

EXAMPLE 25

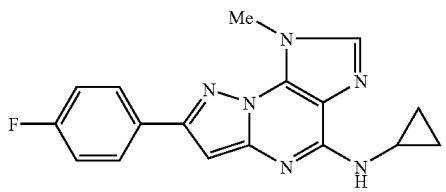

1-Methyl-4-cyclopropylamino-7-(4'-fluorophenyl)-pyrazolo[5,1-b]purine

A. 4-Fluorophenyl trimethylstannane

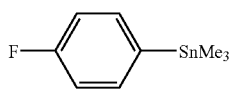

The title compound is prepared by the method of Example 15, part A, from p-bromo-fluorobenzene and hexamethyl-di-tin.

B. 1-Methyl-4-cyclopropylamino-7-(4'-fluorophenyl)-pyrazolo[5,1-b]purine

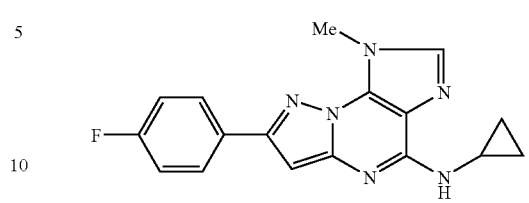

The title compound is prepared by the method of Example 16, part B, from compound XVIII and 4-Fluorophenyl trimethylstannane. ESI m/z=323.34 [(M+H)$^+$; calcd for $C_{17}H_{15}FN_6$+H: 323.14]. $^1$NMR d-MeOD: 7.99 (dd, J=8.81, 5.38 Hz, 2H), 7.95 (s, 1H), 7.20 (t, J=8.80 Hz, 2H), 6.78 (s, 1H), 4.32 (s, 3H), 2.92 (m, 1H), 1.10 (m, 2H), 0.89 (m, 2H)

EXAMPLE 26

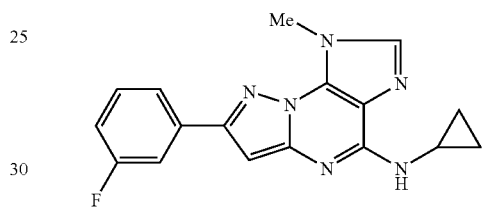

1-Methyl-4-cyclopropylamino-7-(3'-fluorophenyl)-pyrazolo[5,1-b]purine

A. 3-Fluorophenyl trimethylstannane

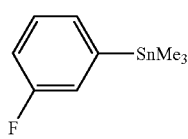

The title compound is prepared by the method of Example 15, part A, from m-bromo-fluorobenzene and hexamethyl-di-tin. 1NMR d-CDCl3: 6.98-6.96 (m. 2H), 6.74-6.68 (m, 1H), 0.31 (s, 9H)

B. 1-Methyl-4-cyclopropylamino-7-(3'-fluorophenyl)-pyrazolo[5,1-b]purine

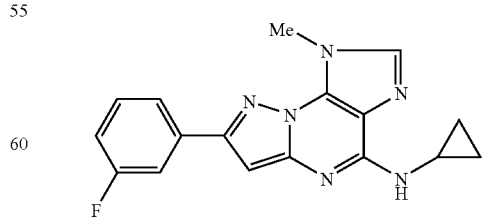

The title compound is prepared by the method of Example 16, part B, from compound XVIII and 3-fluorophenyl trimethylstannane. ESI m/z=323.27 [(M+H)$^+$; calcd for $C_{17}H_{15}FN_6+H$: 323.14]. $^1$NMR d-MeOD: 7.92 (s, 1H), 7.77 (d, J=7.83 Hz, 1H), 7.71 (dt, J=10.03, 1.71 Hz, 1H), 7.47 (m, 1H), 7.13 (td, J=8.07, 2.69 Hz, 1H), 6.76 (s, 1H), 4.33 (s, 3H), 2.92 (m, 1H), 1.04 (m, 2H), 0.83 (m, 2H).

EXAMPLE 27

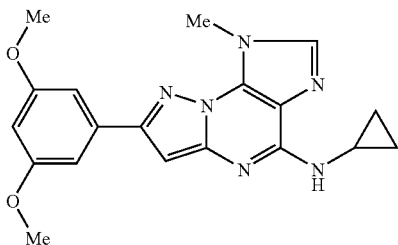

1-Methyl-4-cyclopropylamino-7-(3',5'-dimethoxyphenyl)-pyrazolo[5,1-b]purine

A. 3,5-Dimethoxyphenyl trimethylstannane

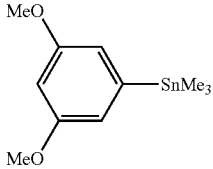

The title compound is prepared by the method of Example 15, part A, from 3,5-dimethoxy-bromo-benzene and hexamethyl-di-tin. $^1$NMR d-CDCl3: 6.62 (d, J=2.20 Hz, 2H), 6.40 (t, J=2.20 Hz, 1H), 3.80 (s, 6H), 0.28 (s, 9H).

B. 1-Methyl-4-cyclopropylamino-7-(3',5'-dimethoxyphenyl)-pyrazolo[5,1-b]purine

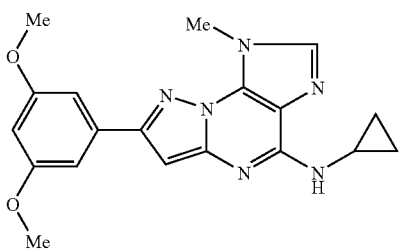

The title compound is prepared by the method of Example 16, part B, from compound XVIII and 3,5-dimethoxyphenyl trimethylstannane. ESI m/z=365.26 [(M+H)$^+$; calcd for $C_{19}H_{20}N_6O_2+H$: 365.17]. $^1$NMR d-CDCl3: 7.45 (s, 1H), 7.11 (d, J=2.44 Hz, 2H), 6.61 (s, 1H), 6.47 (t, J=2.20 Hz, 1H), 5.85 (s, 1H), 4.33 (s, 3H), 3.86 (s, 6H), 3.05-2.99 (m, 1H), 0.94-0.90 (m, 2H), 0.68-0.64 (m, 2H).

EXAMPLE 28

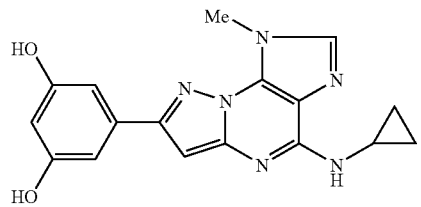

1-Methyl-4-cyclopropylamino-7-(3',5'-dihydroxyphenyl)-pyrazolo[5,1-b]purine

Example 28 was prepared from 27B through a standard de-methylation procedure. ESI m/z=337.24 [(M+H)$^+$; calcd for $C_{17}H_{16}N_6O_2+H$: 337.14]. $^1$NMR d-MeOD: 7.90 H (s, 1H), 6.80 (d, J=2.20 Hz, 1H), 6.61 (s, 1H), 6.22 (t, J=2.20 Hz, 1H), 4.28 (s, 3H), 2.90 (m, 1H), 1.08 (m, 2H), 0.90 (m, 2H).

EXAMPLE 29

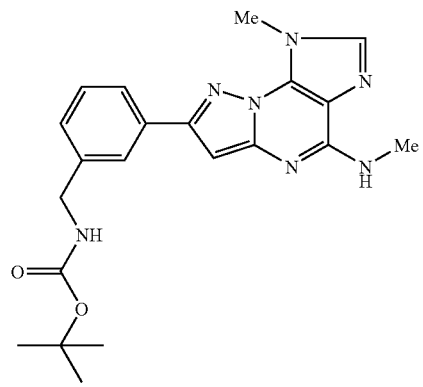

1-Methyl-4-cyclopropylamino-7-(3'-t-butyloxycarboxamidomethyl)phenyl)-pyrazolo[5,1-b]purine A. (3-t-Butyloxycarboxamidomethyl)phenyl trimethylstannane

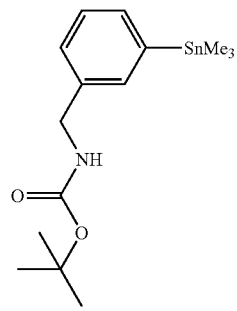

The title compound is prepared by reacting the stannane from Example 19, part A, with di-t-butyl dicarbonate by a method similar to that of Example 21, part A. ¹NMR d-CDCl3: 7.40-7.39 (m, 2H), 7.31 (t, J=7.58 Hz, 1H), 7.23 (d, J=7.58 Hz, 1H), 4.81 (br s, 1H), 4.30 (d, J=5.38 Hz, 2H), 1.47 (s, 9H), 0.28 (s, 9H)

B. 1-Methyl-4-cyclopropylamino-7-(3'-t-butyloxycarboxamidomethyl)phenyl)-pyrazolo[5,1-b]purine

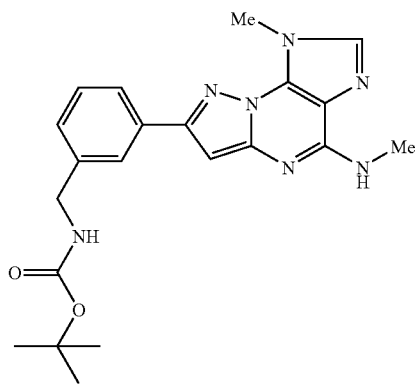

The title compound is prepared by the method of Example 16, part B, from compound XVIII and (3-t-butyloxycarboxamidomethyl)phenyl trimethylstannane. ESI m/z=408.14 [(M+H)⁺; calcd for C₂₁H₂₅N₇O₂+H: 408.21]. ¹NMR d-MeOD: 7.78 (s, 1H), 7.73 (d, J=7.82 Hz, 1H), 7.65 (s, 1H), 7.32 (t, J=7.58 Hz, 1H), 7.21 (d, J=7.58 Hz, 1H), 7.15 (s, 1H), 6.39 (s, 1H), 4.27 (s, 2H), 4.19 (s, 3H), 3.03 (s, 3H), 1.46 (s, 9H)

EXAMPLE 30

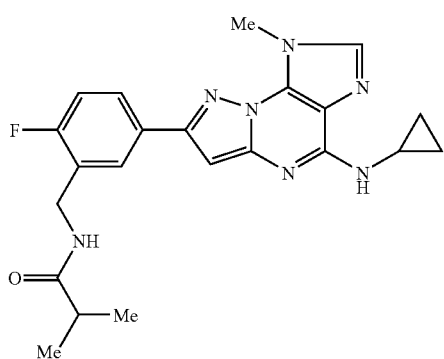

1-Methyl-4-cyclopropylamino-7-(4'-fluoro-3'(2"-methylpropionamidomethyl)phenyl)-pyrazolo[5,1-b]purine A. (4-Fluoro-3-(2'-methylpropionamido)methylphenyl)trimethyl stannane

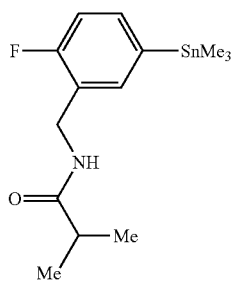

The title compound is prepared by reacting the stannane from Example 19, part A, with isobutyryl chloride by a method similar to that of Example 21, part A.

B. 1-Methyl-4-cyclopropylamino-7-(4'-fluoro-3'(2"-methylpropionamidomethyl)phenyl)-pyrazolo[5,1-b]purine

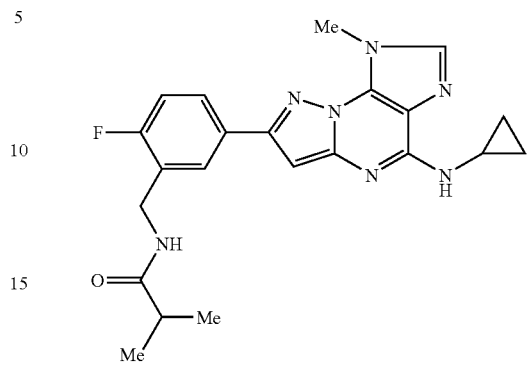

The title compound is prepared by the method of Example 16, part B, from compound XVIII and (4-fluoro-3-(2'-methylpropionamido)methylphenyl)trimethyl stannane. ESI m/z=422.25 [(M+H)⁺; calcd for C₂₂H₂₄FN₇O+H: 422.21]. ¹NMR d-DMSO: 8.34 (t, J=5.62 Hz, 1H), 7.89 (d, J=7.34 Hz, 1H), 7.87-7.83 (m, 1H), 7.73 (d, J=3.91 Hz, 1H), 7.26 (t, J=9.05 Hz, 1H), 6.57 (s, 1H), 4.36 (d, J=5.86 Hz, 2H), 4.23 (s, 3H), 3.32 (s, 3H), 2.97 (br s, 1H), 2.52-2.48 (m, 1H), 1.09 (d, J=6.85 Hz, 6H), 0.76-0.70 (m, 2H), 0.66-0.63 (m, 2H).

EXAMPLE 31

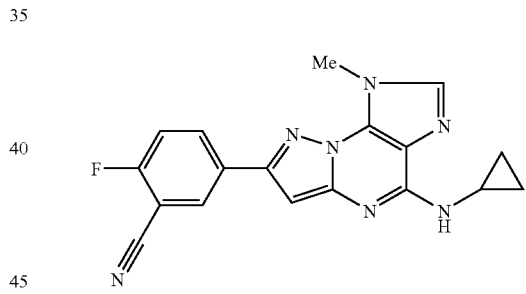

1-Methyl-4-cyclopropylamino-7-(4'-fluoro-3'cyanophenyl)-pyrazolo[5,1-b]purine

A. 2-Fluoro-3-trimethylstannylbenzonitrile

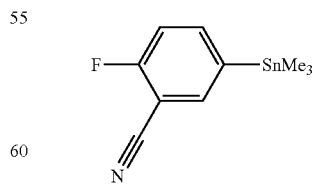

The title compound was prepared by the method of Example 15, part A, from 2-fluoro-5-bromobenzonitrile and hexamethyl-di-tin. ¹NMR d-CDCl3: 7.70-7.65 (m, 2H), 7.17 (dd, J=9.79, 8.07 Hz, 1H), 0.33 (s, 9H).

B. 1-Methyl-4-cyclopropylamino-7-(4'-fluoro-3'cyanophenyl)-pyrazolo[5,1-b]purine

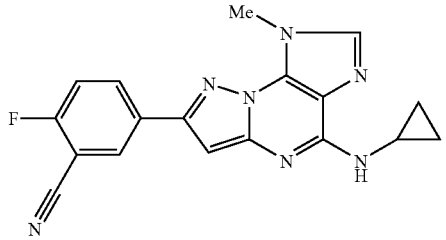

The title compound is prepared by the method of Example 16, part B, from compound XVIII and 2-fluoro-3-trimethylstannylbenzonitrile. ESI m/z=348.22 [(M+H)$^+$; calcd for C$_{18}$H$_{14}$FN$_7$+H: 348.14]. $^1$NMR d-DMSO: 8.48 (d, dd, J=6.36, 2.20 Hz, 1H), 8.37 (ddd, J=8.80, 5.38, 2.45 Hz, 1H), 7.98 (s, 1H), 7.81 (d, J=3.91 Hz, 1H), 7.64 (t, J=9.04 Hz, 1H), 6.78 (s, 1H), 4.26 (s, 3H), 2.98 (br s, 1H), 0.77-0.72 (m, 2H), 0.67-0.63 (m, 2H).

EXAMPLE 32

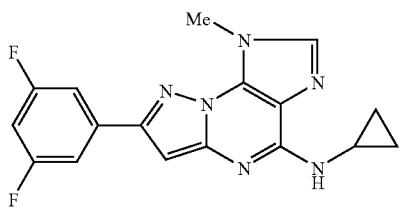

1-Methyl-4-cyclopropylamino-7-(3',5'-difluorophenyl)-pyrazolo[5,1-b]purine

A. 3,5-Difluorophenyl trimethyl stannane

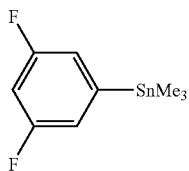

The title compound was prepared by the method of Example 15, part A, from 3,5-difluorobromobenzene and hexamethyl-di-tin. 1NMR d-CDCl3: 6.98-6.95 (m, 2H), 6.71 (tt, J=9.29, 2.45 Hz, 1H), 0.31 (s, 9H).

B. 1-Methyl-4-cyclopropylamino-7-(3',5'-difluorophenyl)-pyrazolo[5,1-b]purine

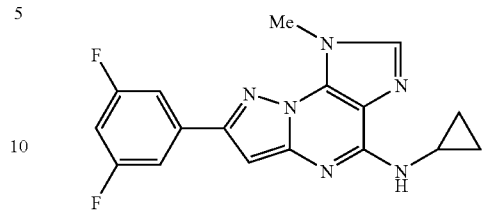

The title compound is prepared by the method of Example 16, part B, from compound XVIII and 3,5-difluorophenyl trimethyl stannane. ESI m/z=341.24 [(M+H)$^+$; calcd for C$_{17}$H$_{14}$F$_2$N$_6$+H: 341.13]. $^1$NMR d-MeOD: 7.92 (s, 1H), 7.58-7.55 (m, 1H), 6.97 (tt, J=11.25, 2.20 Hz, 1H), 6.76 (s, 1H), 4.31 (s, 3H), 2.94-2.89 (m, 1H), 1.05-1.00 (m, 2H), 0.83-0.79 (m, 2H).

EXAMPLE 33

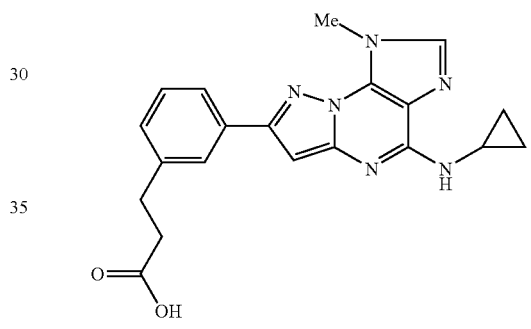

1-Methyl-4-cyclopropylamino-7-(3'-carboxyethylphenyl)-pyrazolo[5,1-b]purine

A. Methyl 2(3'-trimethylstannyl)phenylpropionate

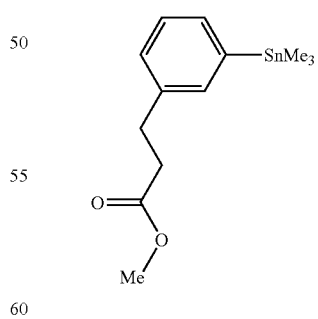

The title compound was prepared by the method of Example 15, part A, from methyl 2(3'-bromophenyl)propionate and hexamethyl-di-tin. $^1$NMR d-CDCl3: 7.34-7.30 (m, 2H), 7.26 (t, J=7.34 Hz, 1H), 7.14 (d, J=7.58 Hz, 1H), 3.67 (s, 3H), 2.94 (t, J=7.82 Hz, 2H), 2.63 (t, J=8.07 Hz, 2H), 0.27 (s, 9H).

B. 1-Methyl-4-cyclopropylamino-7-(3'-methoxycarbonylethylphenyl)-pyrazolo[5,1-b]purine

EXAMPLE 34

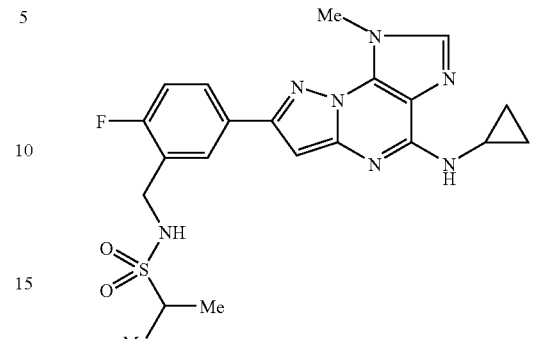

1-Methyl-4-cyclopropylamino-7-(4'-fluoro-3'(1''-methylethanesulfonamidomethyl)phenyl)-pyrazolo[5,1-b]purine

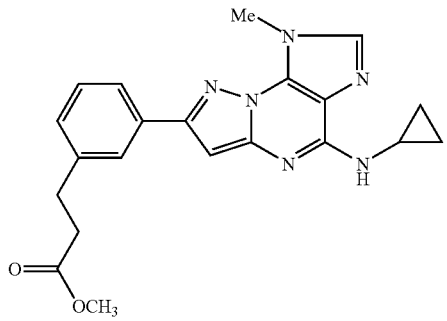

A. 3(1'-Methylethylsulfonamidomethyl)-4-fluorophenyl trimethylstannane

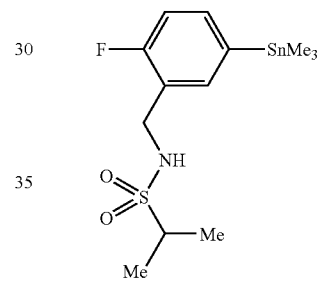

The title compound is prepared by the method of Example 16, part B, from compound XVIII and methyl 2(3'-trimethylstannyl)phenylpropionate.

C. 1-Methyl-4-cyclopropylamino-7-(3'-carboxyethylphenyl)-pyrazolo[5,1-b]purine

The title compound is prepared from 3-aminomethyl-4-fluorophenyl trimethylstannane and isopropylsulfonyl chloride by the method of Example 20, part B.

B. 1-Methyl-4-cyclopropylamino-7-(4'-fluoro-3'(1''-methylethanesulfonamidomethyl)-phenyl)-pyrazolo[5,1-b]purine

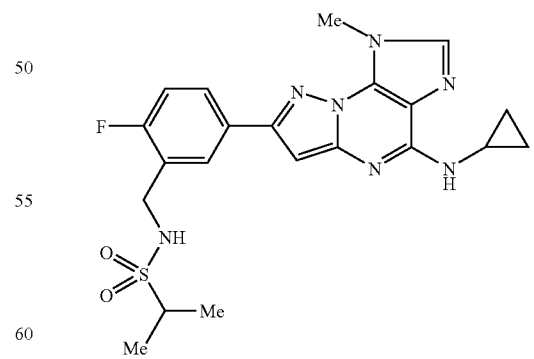

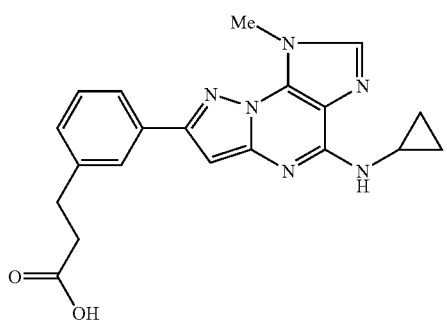

The title compound is prepared from 1-methyl-4-cyclopropylamino-7-(3'-methoxycarbonylethylphenyl)-pyrazolo[5,1-b]purine by the method of example 24. ESI m/z=377.25 [(M+H)$^+$; calcd for $C_{20}H_{20}N_6O_2$+H: 377.17]. $^1$NMR d-MeOD: 7.82 (s, 1H), 7.80 (s, 1H), 7.77 (d, J=7.58 Hz, 1H), 7.34 (t, J=7.58 Hz, 1H), 7.23 (d, J=7.83 Hz, 1H), 6.58 (s, 1H), 4.31 (s, 3H), 2.98 (t, J=7.58 Hz, 2H), 2.90 (m, 1H), 2.65 (t, J=7.82 Hz, 2H), 0.90 (m, 2H), 0.67 (m, 2H).

The title compound is prepared by the method of Example 16, part B, from compound XVIII and 3(1'-methylethylsulfonamidomethyl)-4-fluorophenyl trimethylstannane. ESI m/z=458.20 [(M+H)$^+$; calcd for $C_{21}H_{24}FN_7O_2S$+H: 458.18]. $^1$NMR d-DMSO: 8.10 (d, J=7.09 Hz, 1H), 7.96 (s, 1H), 7.92-7.88 (m, 1H), 7.74 (d, J=3.66 Hz, 1H), 7.66 (t, J=6.36 Hz, 1H), 7.28 (t, J=9.54 Hz, 1H), 6.59 (s, 1H), 4.29 (d, J=6.11 Hz, 2H), 4.26 (s, 3H), 3.32 (s, 3H), 3.18-3.14 (m, 1H), 2.98 (br s, 1H), 1.24 (d, J=6.60 Hz, 6H), 0.76-0.71 (m, 2H), 0.67-0.63 (m, 2H).

EXAMPLE 35

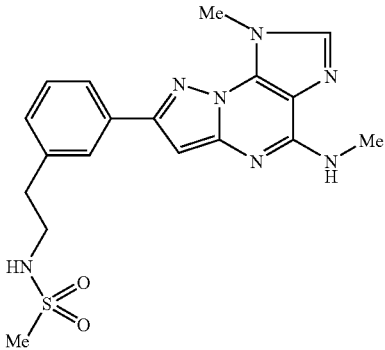

1-Methyl-4-methylamino-7-(3'-methanesulfonami-doethylphenyl)-pyrazolo[5,1-b]purine A. 3(2'-Aminoethyl)phenyl trimethylstannane The title compound was prepared by the method of example 20, part A, from 3-bromo-phenethylamine and hexamethyl-di-tin.

B. 3(2'-Methanesulfonamidoethyl)phenyl trimethylstannane

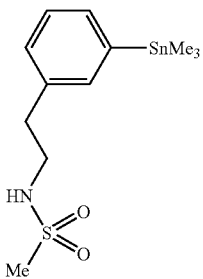

The title compound was prepared by the method of example 17, part A, from 3(2'-aminoethyl)phenyl trimethylstannane and methanesulfonyl chloride.

C. 1-Methyl-4-methylamino-7-(3'-methanesulfonamidoethylphenyl)-pyrazolo[5,1-b]purine

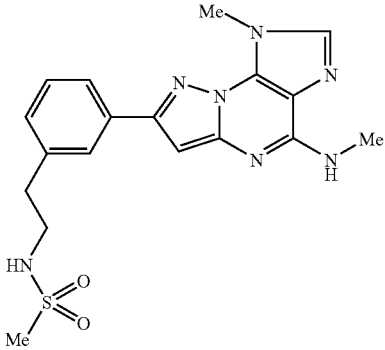

The title compound is prepared by the method of Example 16, part B, from compound XVII and 3(2'-methanesulfonamidoethyl)phenyl trimethylstannane. ESI m/z=400.08 [(M+H)$^+$; calcd for $C_{18}H_{21}N_7O_2S$+H: 400.16]. $^1$NMR d-MeOD: 7.91 (s, 1H), 7.89 (s, 1H), 7.84 (d, J=7.58 Hz, 1H), 7.42 (t, J=7.58 Hz, 1H), 7.32 (d, J=7.33 Hz, 1H), 6.70 (s, 1H), 4.33 (s, 3H), 3.38 (t, J=7.09 Hz, 2H), 3.22 (s, 3H), 2.94 (t, J=7.09 Hz, 2H), 2.85 (s, 3H).

EXAMPLE 36

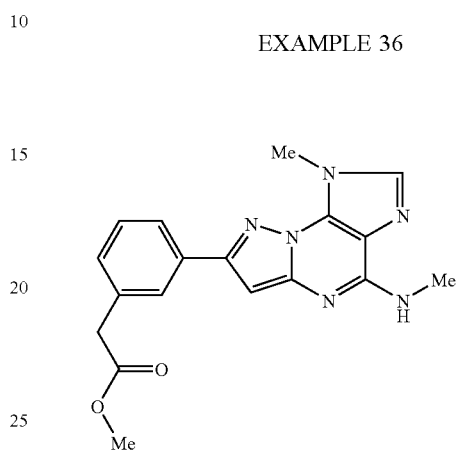

1-Methyl-4-methylamino-7-(3'-methoxycarbonylm-ethylphenyl)-pyrazolo[5,1-b]purine The title compound is prepared by the method of Example 16, part B, from compound XVII and the stannane from example 23. ESI m/z=351.09 [(M+H)$^+$; calcd for $C_{18}H_{18}N_6O_2$+H: 351.16]. $^1$NMR d-DMSO: 7.95 (s, 1H), 7.86 (m, 2H), 7.83 (s, 1H), 7.56 (m, 1H), 7.41 (t, J=7.58 Hz, 1H), 7.26 (d, J=7.58 Hz, 1H), 6.58 (s, 1H), 4.26 (s, 3H), 3.76 (s, 3H), 3.64 (s, 3H), 2.96 (d, J=4.65 Hz, 2H).

EXAMPLE 37

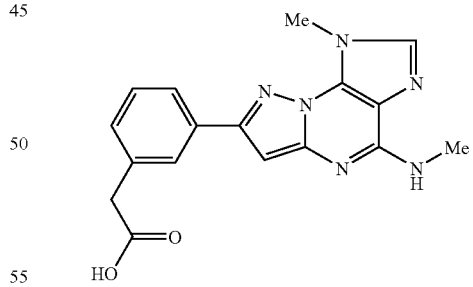

1-Methyl-4-methylamino-7-(3'-carboxymethylphe-nyl)-pyrazolo[5,1-b]purine

The title compound is prepared by the method of Example 24 from the compound of Example 36. ESI m/z=337.06 [(M+H)$^+$; calcd for $C_{17}H_{16}N_6O_2$+H: 337.14]. $^1$NMR d-DMSO: 7.99 (s, 1H), 7.90 (br s, 1H), 7.86 (m, 2H), 7.83 (s, 1H), 7.41 (t, J=7.58 Hz, 1H), 7.26 (d, J=7.83 Hz, 1H), 6.61 (s, 1H), 4.26 (s, 3H), 3.65 (s, 2H), 3.17 (s, 3H)

EXAMPLE 38

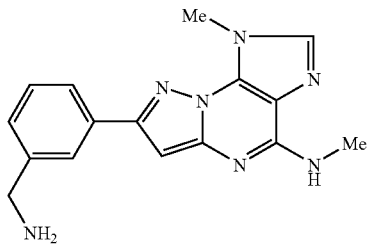

1-Methyl-4-methylamino-7-(3'-aminomethylphenyl)-pyrazolo[5,1-b]purine

The title compound is prepared by the method of Example 16, part B, from compound XVIII and the stannane from example 19. ESI m/z=308.15 [(M+H)$^+$; calcd for $C_{16}H_{17}N_7$+H: 308.16].

Alternate Preparation of Example 38

7-(3-(aminomethyl)phenyl)-N,1-dimethyl-1H-pyrazolo[5,1-b]purin-4-amine

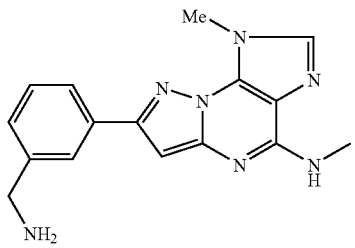

Example 38

7-(3-(Aminomethyl)phenyl)-N,1-dimethyl-1H-pyrazolo[5,1-b]purin-4-amine

A mixture of Example 64 (0.303 g, 1.0 mmol), in THF was cooled to −78° C. A solution of 1M Lithium aluminium hydride (1 ml., 1.0 mmol) was slowly added over 30 minutes. After complete addition the reaction mixture was warmed to room temperature and stirred at room temperature for two hours. HPLC/LC-MS analysis showed complete conversion to the desired product. The reaction mixture was quenched sequentially with 1 ml. H$_2$O, 1 ml. 15% NaOH, 3 ml. H$_2$O. then filtered through Celite. The filtrate was concentrated in vacuo, and the residue purified by chromatography on Reverse-Phase PREP HPLC. The product was obtained as a white solid (0.167 g, 54%). $^1$H NMR (d-MeOD, 400 MHz): 8.1(s, 1H), 8.0(d, 1H), 7.90 (s, 1H), 7.5(m, 1H), 7.4 (m, 1H), 6.7(s,1H), 4.30 (s, 3H), 4.1(s, 2H), 3.2 (s, 3H). ESI m/z=307.35 [(M+H)$^+$; calcd for $C_{14}H_{11}N_5O$+H: 308]; HPLC RT=1.370 min[4 min grad, 10% MeOH/90% water to 90% MeOH/10% water]

EXAMPLE 39

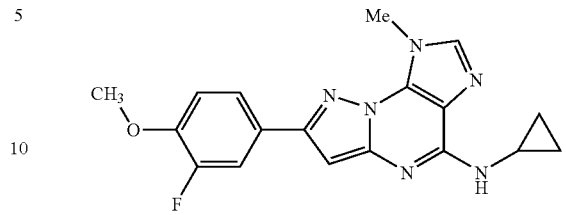

1-Methyl-4-cyclopropylamino-7-(3'-fluoro-4'-methoxyphenyl)-pyrazolo[5,1-b]purine A. 3-Fluoro-4-methoxyphenyl pinacolatoboron

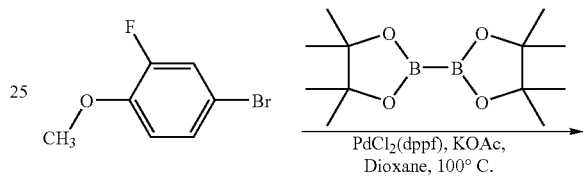

A mixture of 4-bromo-2-fluoroanisole (5.3115 g, 25.8 mmol), Bis(pinacolato) diboron (9.844 g, 38.8 mmol) and KOAc (7.609 g, 77.5 mmol) was heated at 100° C. at the presence of PdCl$_2$(dppf).CH$_2$Cl$_2$ (1.055 g, 1.29 mmol) in Dioxane (100 mL). After 3 h, normal EtOAc/H$_2$O workup followed by flash chromatography (EtOAc/Hexanes, 5%) furnished compound 16 (17.02 g, 77.5%) an oil.

B. 1-Methyl-4-cyclopropylamino-7-(3'-fluoro-4'-methoxyphenyl)-pyrazolo[5,1-b]purine

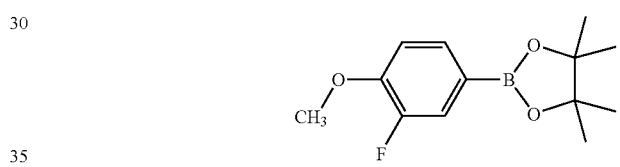

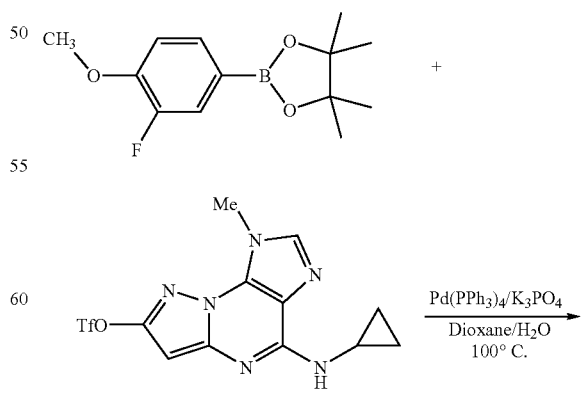

XVIII

-continued

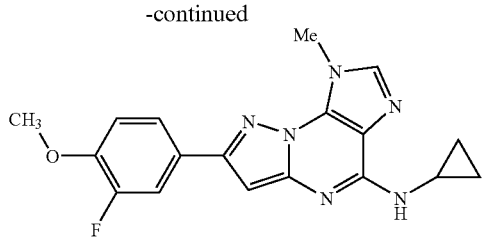

A mixture of 3-fluoro-4-methoxyphenyl pinacolatoboron (75.4 mg, 0.300 mmol), XVIII (185.2 mg, 0.601 mmol), Pd(PPh$_3$)$_4$ (23.1 mg, 0.020 mmol) and K$_3$PO$_4$ (127.6 mg, 0.601 mmol) was heated at 100° C. in Dioxane/H$_2$O (4:1, 2.0 mL). After 1.5 h, concentration followed by flash chromatography (MeOH/CH$_2$Cl$_2$, 5%) furnished the title compound (57.4 mg, 70%) as a white solid. LC-MS (+H):353.34; calc for C$_{18}$H$_{17}$FN$_6$O+H: 353.15. $^1$NMR d-MeOD: 7.91 (s, 1H), 7.72 (d, J=5.14 Hz, 1H), 7.69 (s, 1H), 7.17 (t, J=8.56 Hz, 1H), 6.68 (s, 1H), 4.31 (s, 3H), 3.91 (s, 3H), 2.93-2.87 (m, 1H), 1.06-1.01 (m, 2H), 0.85-0.81 (m, 2H).

EXAMPLE 40

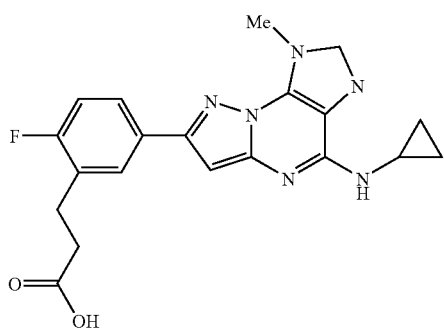

1-Methyl-4-cyclopropylamino-7-(4'-fluoro-3'-carboxyethylphenyl)-pyrazolo[5,1-b]purine A. Methyl 3(2'-fluoro-5-bromophenyl)propionate

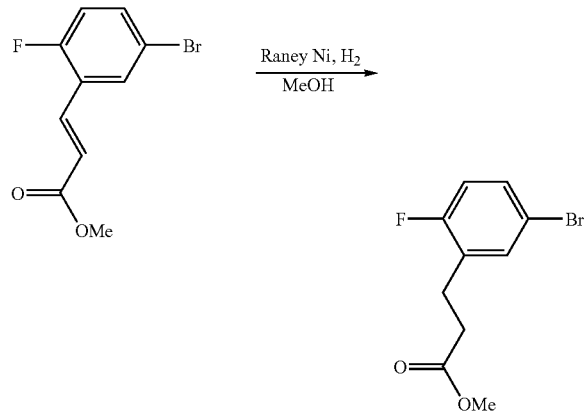

Compound 40A was prepared according to the above scheme.

B. 4-Fluoro-3-methoxycarbonylethylphenyl pinacolatoboron

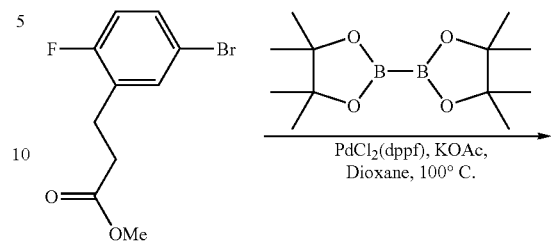

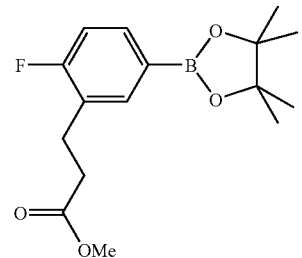

A mixture of methyl 3(2'-fluoro-5-bromophenyl)propionate (g, mmol), bis(pinacolato)diboron (g, mmol) and KOAc (g, mmol) was heated at 100° C. at the presence of PdCl$_2$(dppf).CH$_2$Cl$_2$ (g, mmol) in Dioxane (mL). After h, extractive EtOAc/H$_2$O workup followed by flash chromatography (EtOAc/Hexanes, 5%) furnished the title compound as an oil.

C. 1-Methyl-4-cyclopropylamino-7-(4'-fluoro-3'-methoxycarbonylethylphenyl)-pyrazolo[5,1-b]purine Compound 40C was prepared from compound 40B and 3-fluoro-4-methoxyphenyl pinacolatoboron XVIII, by the method of Example 39, part B.

D. 1-Methyl-4-cyclopropylamino-7-(4'-fluoro-3'-carboxyethylphenyl)-pyrazolo[5,1-b]purine

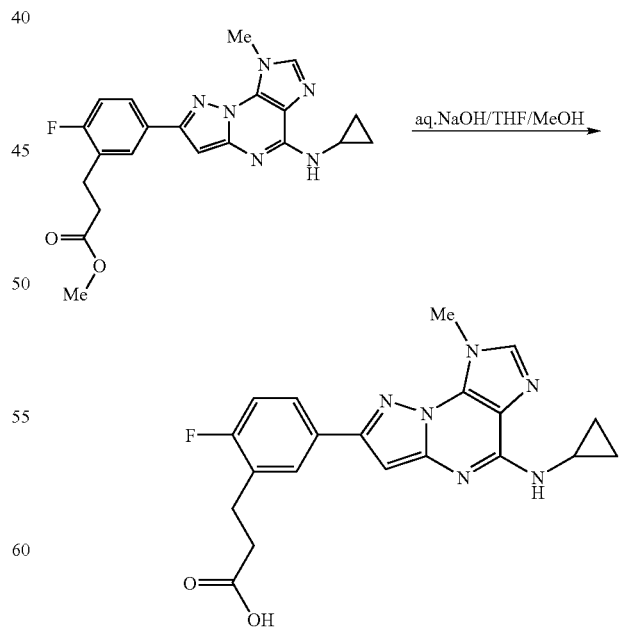

A mixture of 1-methyl-4-cyclopropylamino-7-(4'-fluoro-3'-methoxycarbonylethylphenyl)-pyrazolo[5,1-b]purine (57.4 mg, 0.141 mmol) in THF/MeOH/1.0 N NaOH (3.5 mL, 4:2:1) was stirred at room temperature. After 3 days, neutralization with 1.0 N HCl precipitated a white solid. Filtration followed by wash with H₂O and acetone furnished the title compound (26.9 mg, 49%) as a white solid. ¹H NMR (d-MeOD, 400 MHz): 7.88 (d, J=7.34 Hz, 1H), 7.83 (s, 1H), 7.86-7.80 (m, 1H), 7.12 (t, J=9.78 Hz, 1H), 6.58 (s, 1H), 4.32 (s, 3H), 3.01 (t, J=7.83 Hz, 2H), 2.90 (m, 1H), 2.65 (t, J=7.82 Hz, 2H), 0.93 (m, 2H), 0.70 (m, 2H).

EXAMPLE 41

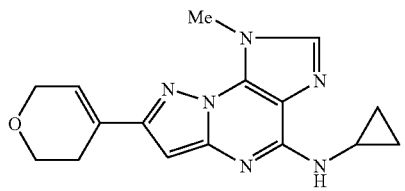

1-Methyl-4-cyclopropylamino-7-(4'(2'H)pyranyl-pyrazolo[5,1-b]purine

A. 4-(2H)Pyranyl-pinacolatoboron

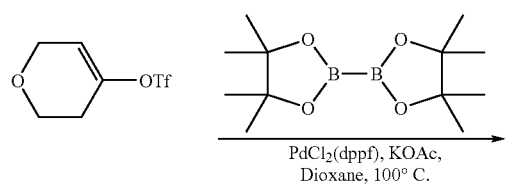

Compound 41A was prepared according to the above scheme.

B. 1-Methyl-4-cyclopropylamino-7-(4'(2'H)pyranyl-pyrazolo[5,1-b]purine

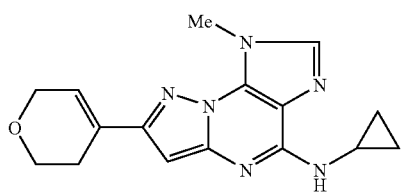

The title compound was prepared by the method of Example 39, part B, from XVIII and 4-(2H)pyranyl-pinacolatoboron. ESI m/z=311.24 [(M+H)⁺; calcd for $C_{16}H_{18}N_6O+H$: 311.16]. ¹NMR d-MeOD: 7.69 (s, 1H), 6.37 (s, 1H), 6.22 (s, 1H), 4.30-4.28 (m, 2H), 4.17 (s, 3H), 3.89 (t, J=5.63 Hz, 2H), 2.85 (7 lines, J=3.66 Hz, 1H), 2.61-2.55 (m, 2H), 0.89-0.84 (m, 2H), 0.64-0.60 (m, 2H)

EXAMPLE 42

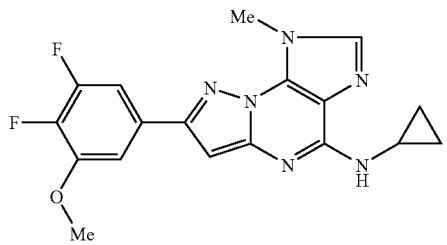

1-Methyl-4-cyclopropylamino-7-(4',5'-difluoro-3-methoxyphenyl)-pyrazolo[5,1-b]purine A. 4,5-Difluoro-3-methoxycarbonylethylphenyl pinacolatoboron

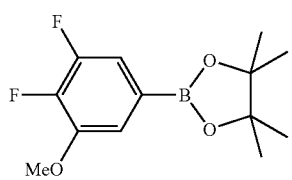

The title compound was prepared by the method of Example 39, part A, from 4,5-difluoro-3-methoxybromobenzene and bis(pinacolato)diboron.

B. 1-Methyl-4-cyclopropylamino-7-(4',5'-difluoro-3-methoxyphenyl)-pyrazolo[5,1-b]purine

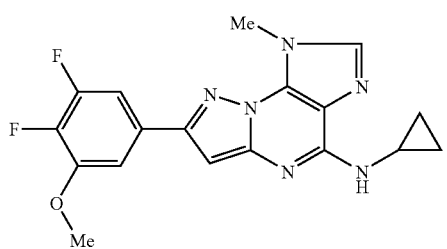

The title compound was prepared by the method of Example 39, part B, from XVIII and 4,5-difluoro-3-methoxycarbonylethylphenyl pinacolatoboron. ESI m/z=371.31 [(M+H)⁺; calcd for $C_{18}H_{16}F_2N_6O+H$: 371.14]. ¹NMR d-MeOD: 7.91 (s, 1H), 7.50-7.43 (m, 2H), 6.74 (s, 1H), 4.32 (s, 3H), 3.99 (s, 1H), 2.94-2.89 (m, 1H), 1.05-1.00 (m, 2H), 0.83-0.79 (m, 2H)

EXAMPLE 43

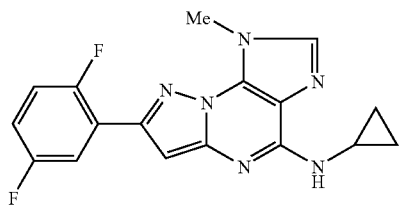

1-Methyl-4-cyclopropylamino-7-(2',5'-difluorophenyl)-pyrazolo[5,1-b]purine

A. 2,5-Difluoro-phenyl pinacolatoboron

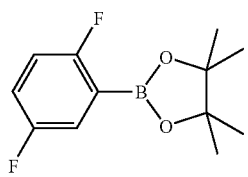

The title compound was prepared by the method of Example 39, part A, from 2,5-difluorobromobenzene and bis(pinacolato)diboron. $^1$NMR d-CDCl3: 7.59-7.50 (m, 2H), 7.17-7.10 (m, 1H), 1.33 (s, 12H).

B. 1-Methyl-4-cyclopropylamino-7-(2',5'-difluorophenyl)-pyrazolo[5,1-b]purine

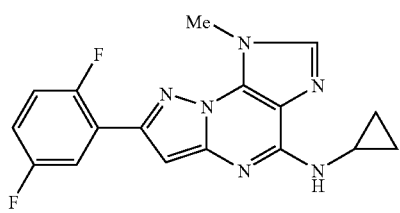

The title compound was prepared by the method of Example 39, part B, from XVIII and 2,5-difluoro-phenyl pinacolatoboron. $^1$NMR d-MeOD: 7.89-7.84 (m, 1H), 7.83 (s, 1H), 7.24-7.18 (m, 1H), 7.12-7.06 (m, 1H), 6.69 (d, J=4.16 Hz, 1H), 4.32 (s, 3H), 2.90 (m, 1H), 0.88 (m, 2H), 0.65 (m, 2H).

EXAMPLE 44

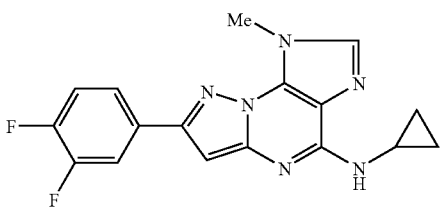

1-Methyl-4-cyclopropylamino-7-(3',4'-difluorophenyl)-pyrazolo[5,1-b]purine

A. 3,4-Difluoro-phenyl pinacolatoboron

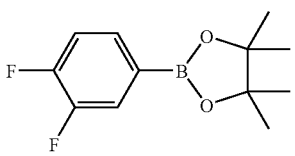

The title compound was prepared by the method of Example 39, part A, from 3,4-difluorobromobenzene and bis(pinacolato)diboron.

B. 1-Methyl-4-cyclopropylamino-7-(3',4'-difluorophenyl)-pyrazolo[5,1-b]purine

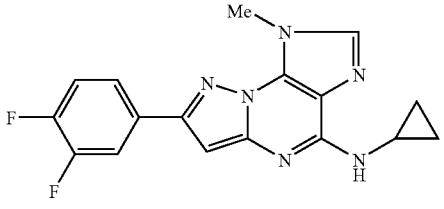

The title compound was prepared by the method of Example 39, part B, from XVIII and 3,4-Difluoro-phenyl pinacolatoboron. $^1$NMR d-MeOD: 7.92 (s, 1H), 7.87 (d, J=9.79 Hz, 1H), 7.77 (apparent d, J=8.56 Hz, 1H), 7.35 (dd, J=18.34, 9.05 Hz, 1H), 6.73 (s, 1H), 4.32 (s, 3H), 2.91 (m, 1H), 1.02 (m, 2H), 0.82 (m, 2H).

EXAMPLE 45

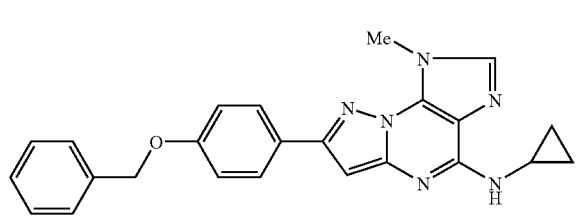

1-Methyl-4-cyclopropylamino-7-(4'-benzyloxyphe-nyl)-pyrazolo[5,1-b]purine

A. 4-Benzyloxy-phenyl pinacolatoboron

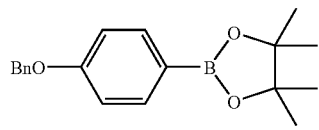

The title compound was prepared by the method of Example 39, part A, from 4-benzyloxybromobenzene and bis(pinacolato)diboron.

B. 1-Methyl-4-cyclopropylamino-7-(4'-benzyloxyphenyl)-pyrazolo[5,1-b]purine

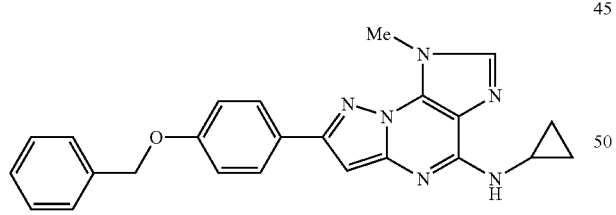

The title compound was prepared by the method of Example 39, part B, from XVIII and 4-benzyloxy-phenyl pinacolatoboron. ESI m/z=411.33 [(M+H)$^+$; calcd for $C_{24}H_{22}N_6O+H$: 411.19]. $^1$NMR d-MeOD: 7.89 (s, 1H), 7.86 (d, J=8.80 Hz, 2H), 7.44 (d, J=7.34 Hz, 2H), 7.36 (t, J=7.09 Hz, 2H), 7.30 (t, J=7.34 Hz, 1H), 7.06 (d, J=8.80 Hz, 2H), 6.66 (s, 1H), 5.12 (s, 2H), 4.29 (s, 3H), 2.92-2.87 (m, 1H), 1.08-1.03 (m, 2H), 0.86-0.82 (m, 2H).

EXAMPLE 46

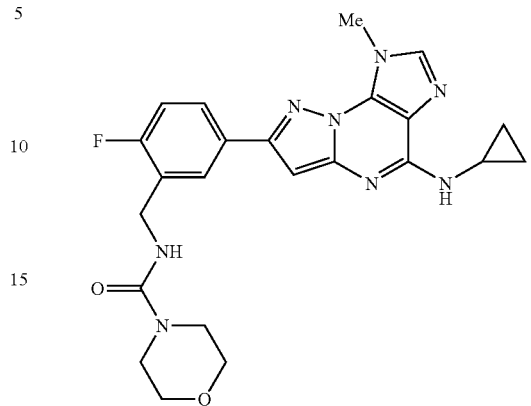

1-Methyl-4-cyclopropylamino-7-(4'-fluoro-3'-(1"-morpholinecarboxamidomethyl-phenyl)-pyrazolo[5,1-b]purine

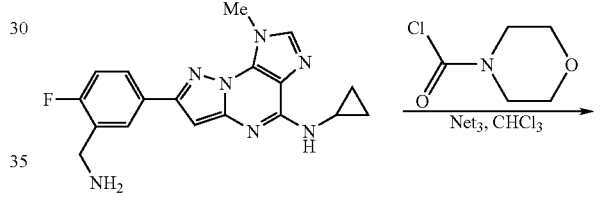

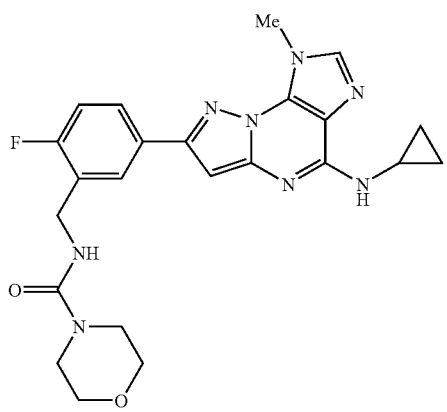

A mixture of 1-methyl-4-cyclopropylamino-7-(4'-fluoro-3'-aminomethyl-phenyl)-pyrazolo[5,1-b]purine (Example 15) (28.6 mg, 0.0814 mmol), morpholine-4-carbonylchloride (14.2 µL, 0.122 mmol) and NEt$_3$ (50 µL, 0.359 mmol) was stirred in CHCl$_3$ (1.0 mL) at room temperature. After 3 h, it was quenched with MeNH$_2$ (1.0 M/THF). Concentration followed by preparative HPLC provided 22 (6.5 mg, 17%) as a white solid. $^1$H NMR (d-MeOD, 400 MHz): 7.91 (dd, J=6.15, 2.02 Hz, 1H), 7.88 (s, 1H), 7.83 (m, 1H), 7.15 (t, J=8.19 Hz, 1H), 6.66 (s, 1H), 4.46 (s, 2H), 4.29 (s, 3H), 3.66 (d, J=4.78 Hz, 2H), 3.41 (d, J=4.78 Hz, 2H), 3.28 (m, 1H), 1.05 (m, 2H), 0.84 (m, 2H); ESI m/z=465.32 [(M+H)$^+$; calcd for $C_{23}H_{25}N_8O_2$: 465.22].

EXAMPLE 47

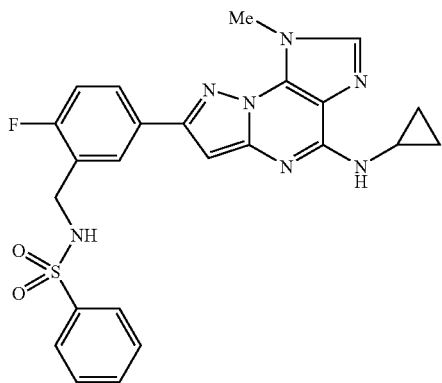

1-Methyl-4-cyclopropylamino-7-(4'-fluoro-3'-(1"-benzenesulfonamidomethyl-phenyl)-pyrazolo[5,1-b] purine The title compound was prepared by the method of Example 46 from the compound of Example 15 and benzenesulfonyl chloride. ESI m/z=492.14 [(M+H)$^+$; calcd for $C_{24}H_{22}FN_7O_2S$+H: 492.16]. 1NMR d-MeOD: 7.83-7.75 (m, 5H), 7.48-7.40 (m, 3H), 6.98 (t, J=9.78 Hz, 1H), 6.47 (s, 1H), 4.32 (s, 3H), 4.20 (s, 2H), 2.93-2.88 (m, 1H), 0.92-0.87 (m, 2H), 0.67-0.63 (m, 2H)

EXAMPLE 48

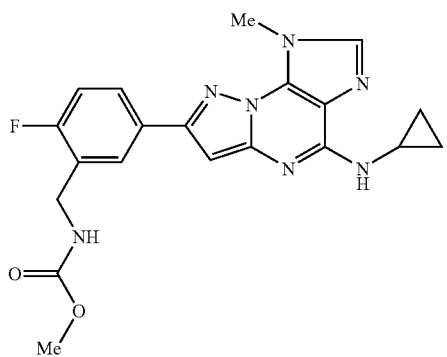

1-Methyl-4-cyclopropylamino-7-(4'-fluoro-3'-(methoxycarboxamidomethyl-phenyl)-pyrazolo[5,1-b] purine The title compound was prepared by the method of Example 46 from the compound of Example 15 and methyl chloroformate. ESI m/z=410.14 [(M+H)$^+$; calcd for $C_{20}H_{20}FN_7O_2$+H: 410.17]. $^1$NMR V

EXAMPLE 49

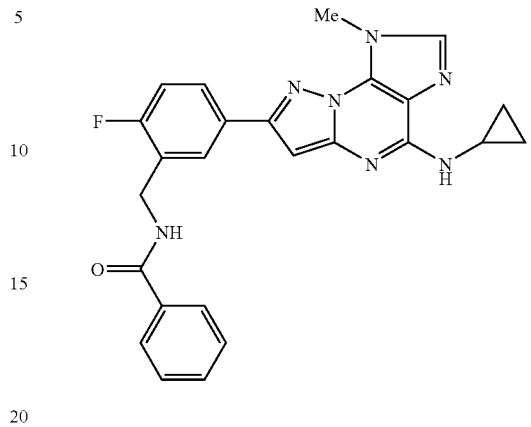

1-Methyl-4-cyclopropylamino-7-(4'-fluoro-3'-(benzamidomethyl-phenyl)-pyrazolo[5,1-b]purine The title compound was prepared by the method of Example 46 from the compound of Example 15 and benzoyl chloride. ESI m/z=456.19 [(M+H)$^+$; calcd for $C_{25}H_{22}FN_7O$+H: 456.19]. $^1$NMR d-MeOD: 7.99 (dd, J=7.34, 1.96 Hz, 1H), 7.89 (dd, J=8.56, 1.47 Hz, 2H), 7.83 (ddd, J=8.56, 5.13, 2.20 Hz, 1H), 7.74 (s, 1H), 7.54 (t, J=7.34 Hz, 1H), 7.47 (t, J=7.82 Hz, 2H), 7.15 (dd, J=9.78, 8.56 Hz, 1H), 6.47 (s, 1H), 4.69 (s, 2H), 4.17 (s, 3H), 2.89-2.84 (m, 1H), 0.88-0.84 (m, 2H), 0.64-0.61 (m, 2H)

EXAMPLE 50

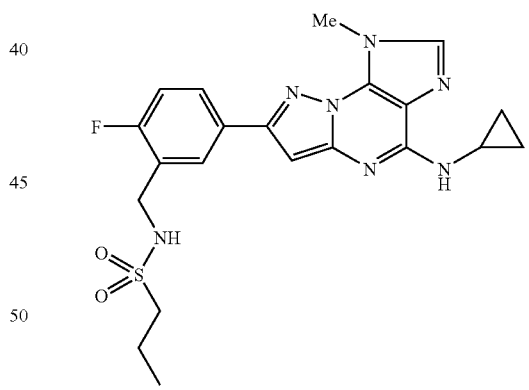

1-Methyl-4-cyclopropylamino-7-(4'-fluoro-3'-(propanesulfonamidomethyl-phenyl)-pyrazolo[5,1-b] purine The title compound was prepared by the method of Example 46 from the compound of Example 15 and propanesulfonyl chloride. ESI m/z=458.19 [(M+H)$^+$; calcd for $C_{21}H_{24}FN_7O_2S$+H: 458.18]. $^1$NMR d-MeOD: 7.91 (d, J=7.34 Hz, 1H), 7.87-7.83 (m, 1H), 7.78 (s, 1H), 7.13 (t, J=8.80 Hz, 1H), 6.51 (s, 1H), 4.46 (s, 2H), 4.29 (s, 3H), 2.92-2.87 (m, 1H), 2.27 (q, J=7.58 Hz, 2H), 1.17 (t, J=7.58 Hz, 3H), 0.90-0.85 (m, 2H), 0.66-0.62 (m, 2H)

EXAMPLE 51

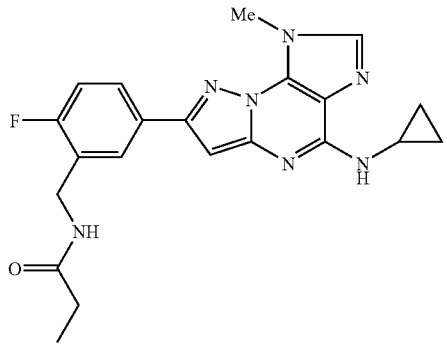

1-Methyl-4-cyclopropylamino-7-(4'-fluoro-3'-(propionamidomethyl-phenyl)-pyrazolo[5,1-b]purine The title compound was prepared by the method of Example 46 from the compound of Example 15 and propionyl chloride. ESI m/z=408.14 [(M+H)$^+$; calcd for $C_{21}H_{22}FN_7O$+H: 408.19]. $^1$NMR d-MeOD: 7.91 (d, J=7.34 Hz, 1H), 7.85 (ddd, J=8.56, 5.13, 2.20 Hz, 1H), 7.78 (s, 1H), 7.13 (dd, J=9.78, 8.80 Hz, 1H), 6.51 (s, 1H), 4.46 (s, 2H), 4.29 (s, 3H), 2.92-2.87 (m, 1H), 2.27 (q, J=7.58 Hz, 2H), 1.17 (t, J=7.58 Hz, 3H), 0.90-0.85 (m, 2H), 0.66-0.62 (m, 2H)

EXAMPLE 52

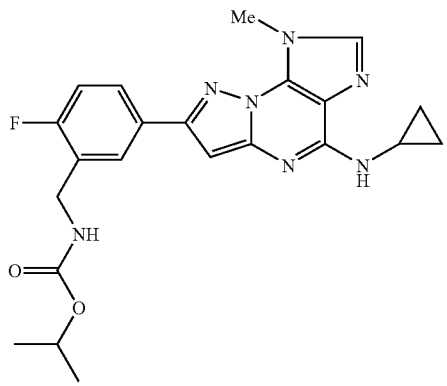

1-Methyl-4-cyclopropylamino-7-(4'-fluoro-3'-(isopropylcarboxamidomethyl-phenyl)-pyrazolo[5,1-b]purine The title compound was prepared by the method of Example 46 from the compound of Example 15 and isopropyl chloroformate. ESI m/z=438.21 [(M+H)$^+$; calcd for $C_{22}H_{24}FN_7O_2$+H: 438.20]. $^1$NMR d-MeOD: 7.92 (d, J=8.56 Hz, 1H), 7.87-7.83 (m, 1H), 7.78 (s, 1H), 7.12 (dd, J=9.78, 8.56 Hz, 1H), 6.51 (s, 1H), 4.89-4.83 (m, 1H), 4.38 (s, 2H), 4.30 (s, 3H), 2.92-2.87 (m, 1H), 1.23 (d, J=6.11 Hz, 6H), 0.90-0.85 (m, 2H), 0.66-0.62 (m, 2H)

EXAMPLE 53

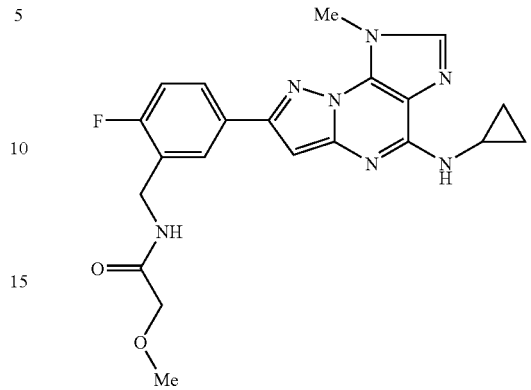

1-Methyl-4-cyclopropylamino-7-(4'-fluoro-3'-(methoxyacetamidomethyl-phenyl)-pyrazolo[5,1-b]purine The title compound was prepared by the method of Example 46 from the compound of Example 15 and methoxyacetyl chloride. ESI m/z=424.15 [(M+H)$^+$; calcd for $C_{21}H_{22}FN_7O_2$+H: 424.19]. $^1$NMR d-MeOD: 7.91 (dd, J=7.09, 1.95 Hz, 1H), 7.85 (ddd, J=8.56, 4.89, 2.20 Hz, 1H), 7.76 (s, 1H), 7.13 (dd, J=9.78, 8.56 Hz, 1H), 6.49 (s, 1H), 4.53 (s, 2H), 4.28 (s, 3H), 3.96 (s, 2H), 3.44 (s, 3H), 2.91-2.86 (m, 1H), 0.90-0.85 (m, 2H), 0.66-0.62 (m, 2H)

EXAMPLE 54

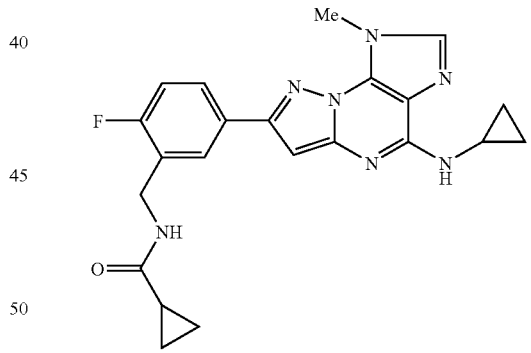

1-Methyl-4-cyclopropylamino-7-(4'-fluoro-3'-(cyclopropanecarboxamidomethyl-phenyl)-pyrazolo[5,1-b]purine The title compound was prepared by the method of Example 46 from the compound of Example 15 and cyclopropanecarbonyl chloride. ESI m/z=420.17 [(M+H)$^+$; calcd for $C_{22}H_{22}FN_7O$+H: 420.19]. $^1$NMR d-MeOD: 7.91 (dd, J=7.09, 1.96 Hz, 1H), 7.85 (ddd, J=8.56, 5.14, 2.20 Hz, 1H), 7.77 (s, 1H), 7.13 (dd, J=9.78, 8.81 Hz, 1H), 6.50 (s, 1H), 4.47 (s, 2H), 4.30 (s, 3H), 2.92-2.87 (m, 1H), 1.69-1.63 (m, 1H), 0.91-0.85 (m, 4H), 0.79-0.75 (m, 2H), 0.66-0.62 (m, 2H)

EXAMPLE 55

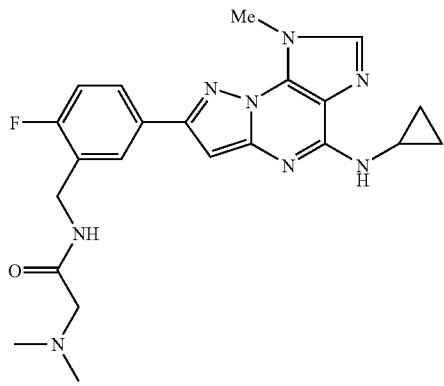

1-Methyl-4-cyclopropylamino-7-(4'-fluoro-3'-(dimethylaminoacetamidomethyl-phenyl)-pyrazolo[5,1-b]purine The title compound was prepared by the method of Example 46 from the compound of Example 15 and dimethylaminoacetyl chloride. $^1$NMR d-MeOD: 7.96 (d, J=6.85 Hz, 1H), 7.94-7.91 (m, 1H), 7.89 (s, 1H), 7.20 (t, J=8.80 Hz, 1H), 6.70 (s, 1H), 4.55 (s, 2H), 4.30 (s, 3H), 3.98 (s, 2H), 2.95-2.88 (m, 7H), 1.05-1.00 (m, 2H), 0.84-0.80 (m, 2H)

EXAMPLE 56

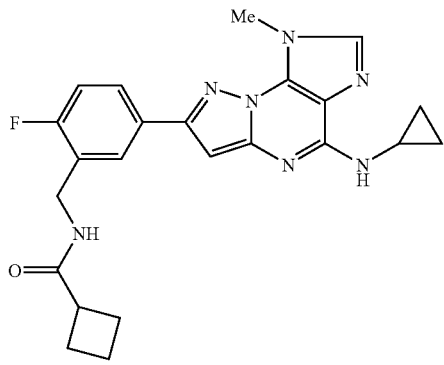

1-Methyl-4-cyclopropylamino-7-(4'-fluoro-3'-(cyclobutanecarboxamidomethyl-phenyl)-pyrazolo[5,1-b]purine The title compound was prepared by the method of Example 46 from the compound of Example 15 and cyclobutanecarbonyl chloride. $^1$NMR d-MeOD: 7.90-7.83 (m, 2H), 7.88 (s, 1H), 7.16 (dd, J=9.78, 8.56 Hz, 1H), 6.66 (s, 1H), 4.45 (s, 2H), 4.28 (s, 3H), 3.28 (apparent quintet, J=1.72 Hz, 1H), 2.92-2.87 (m, 1H), 2.34-2.24 (m, 2H), 2.20-2.12 (m, 2H), 2.06-1.94 (m 1H), 1.90-1.82 (m, 1H), 1.06-1.01 (m, 2H), 0.85-0.81 (m, 2H)

EXAMPLE 57

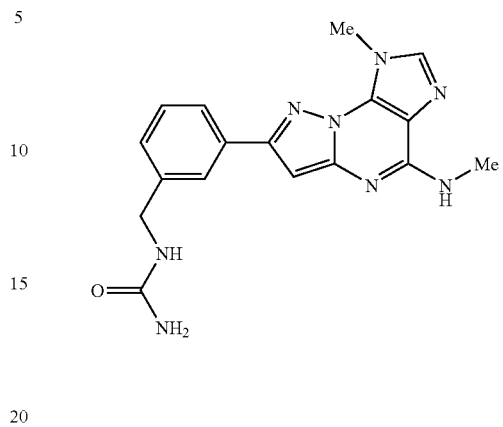

1-Methyl-4-methylamino-7-(3'-(ureidomethyl-phenyl)-pyrazolo[5,1-b]purine

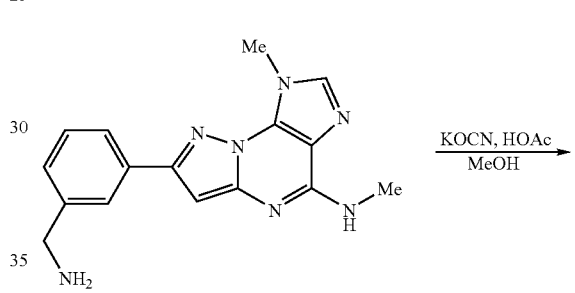

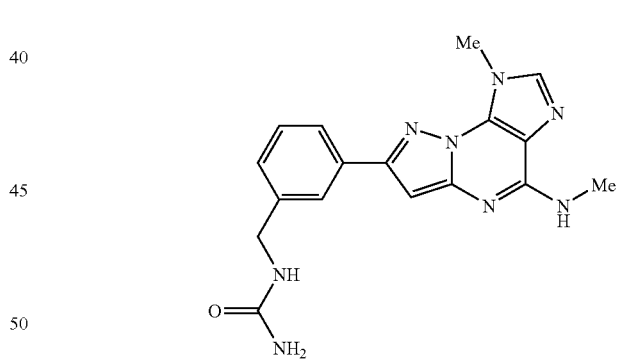

A mixture of 1-methyl-4-methylamino-7-(3'-aminomethylphenyl)-pyrazolo[5,1-b]purine, from Example 38, (11.5 mg, mmol) and KOCN (19.8 mg, mmol) in MeOH (2.0 mL) was treated with HOAc (2 drops), then stirred at room temperature for 4 h. Concentration followed by rinse with EtOAc and H$_2$O furnished the title compound (7.9 mg, %). $^1$H NMR (d-MeOD, 400 MHz): 7.85 (s, 1H), 7.80 (d, J=6.78 Hz, 1H), 7.74 (s, 1H), 7.36 (t, J=8.02 Hz, 1H), 7.27 (d, J=8.01 Hz, 1H), 6.47 (s, 1H), 4.35 (s, 2H), 4.27 (s, 3H), 3.06 (s, 3H); ESI m/z=351.09 [(M+H)$^+$; calcd for C$_{17}$H$_{18}$N$_8$O+H: 351.17]

EXAMPLE 58

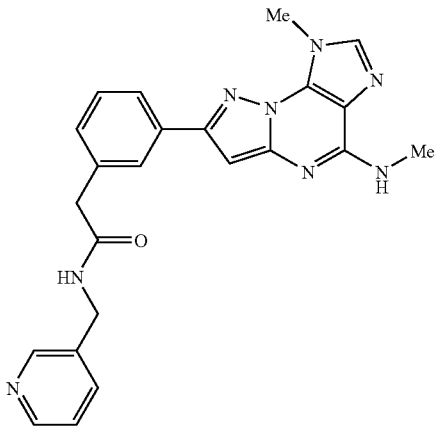

1-Methyl-4-methylamino-7-(3'(3"-pyridylmethylaminocarbonylmethylphenyl)-pyrazolo[5,1-b]purine

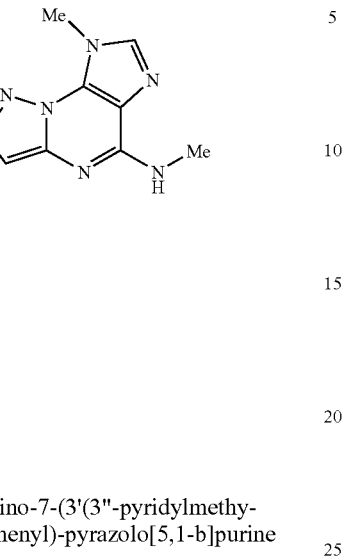

A mixture of 1-methyl-4-methylamino-7-(3'-methoxycarbonylmethylphenyl)-pyrazolo[5,1-b]purine, from Example 36, (14.4 mg, 0.0411 mmol), 3-aminomethyl pyridine (13.3 mg, 0.123 mmol) in Dioxane (1.0 mL) was treated with AlMe$_3$ (62 µL, 0.123 mmol) at room temperature. After stirring overnight, acidification with 1.0 N HCl followed by preparative HPLC provided the title compound (7.2 mg, 41%) as a sticky solid. $^1$H NMR (d-MeOD, 400 MHz): 8.44 (d, J=1, 76 Hz, 1H), 8.37 (dd, J=4.89, 1.47 Hz, 7.89 (s, 1H), 7.84 (d, J=7.83 Hz, 1H), 7.78 (s, 1H), 7.71 (d, J=8.07 Hz, 1H), 7.37 (t, J=7.58 Hz, 1H), 7.33 (dd, J=7.82, 4.89 Hz, 1H), 7.28 (d, J=7.82 Hz, 1H), 6.49 (s, 1H), 4.41 (s, 2H), 4.29 (s, 3H), 3.62 (s, 2H), 3.08 (s, 3H); ESI m/z=427.08 [(M+H)$^+$; calcd for C$_{23}$H$_{22}$N$_8$O+H: 427.20]

EXAMPLE 59

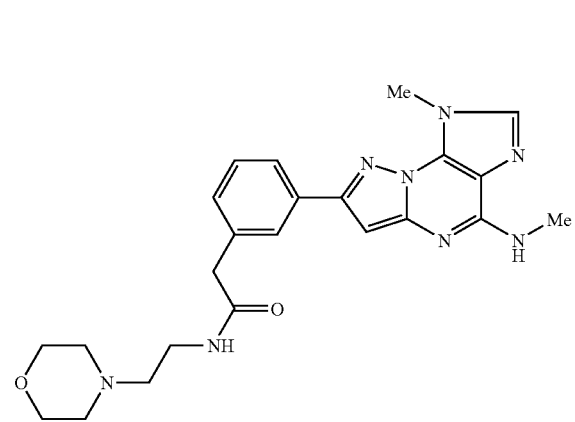

1-Methyl-4-methylamino-7-(3'(1"-morpholinoethylaminocarbonylmethylphenyl)-pyrazolo[5,1-b]purine The title compound was prepared by the method of Example 58 from the compound of Example 36 and 2(1'-morpholinoethyl)amine. ESI m/z=449.29 [(M+H)$^+$; calcd for C$_{23}$H$_{28}$N$_8$O$_2$+H: 449.24]. $^1$NMR d-MeOD: 7.96 (s, 1H), 7.93 (s, 1H), 7.90 (d, J=7.83 Hz, 1H), 7.45 (t, J=7.58 Hz, 1H), 7.37 (d, J=7.82 Hz, 1H), 6.76 (s, 1H), 4.34 (s, 3H), 4.01 (br s, 2H), 3.75 (br s, 2H), 3.66 (s, 2H), 3.61 (t, J=6.11 Hz, 2H), 3.55 (br s, 2H), 3.30 (br s, 2H), 3.24 (s, 3H), 3.15 (br s, 2H)

EXAMPLE 60

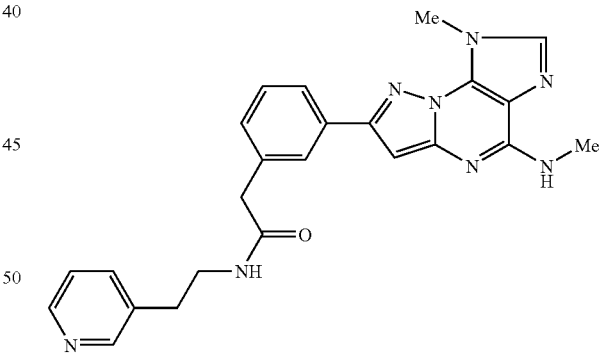

1-Methyl-4-methylamino-7-(3'(3"-pyridylethylaminocarbonylmethylphenyl)-pyrazolo[5,1-b]purine The title compound was prepared by the method of Example 58 from the compound of Example 36 and 2(3'-pyridylethyl)amine. ESI m/z=441.25 [(M+H)$^+$; calcd for C$_{24}$H$_{24}$N$_8$O+H: 441.21]. $^1$NMR d-MeOD: 8.71 (s, 1H), 8.60 (d, J=5.87 Hz, 1H), 7.96 (s, 1H), 7.88 (d, J=7.83 Hz, 1H), 7.83 (s, 1H), 7.81 (dd, J=8.07, 6.11 Hz, 1H), 7.42 (t, J=7.58 Hz, 1H), 7.26 (d, J=7.82 Hz, 1H), 6.75 (s, 1H), 4.34 (s, 3H), 3.58 (t, J=6.84 Hz, 2H), 3.51 (s, 2H), 3.25 (s, 3H), 3.05 (t, J=6.84 Hz, 2H)

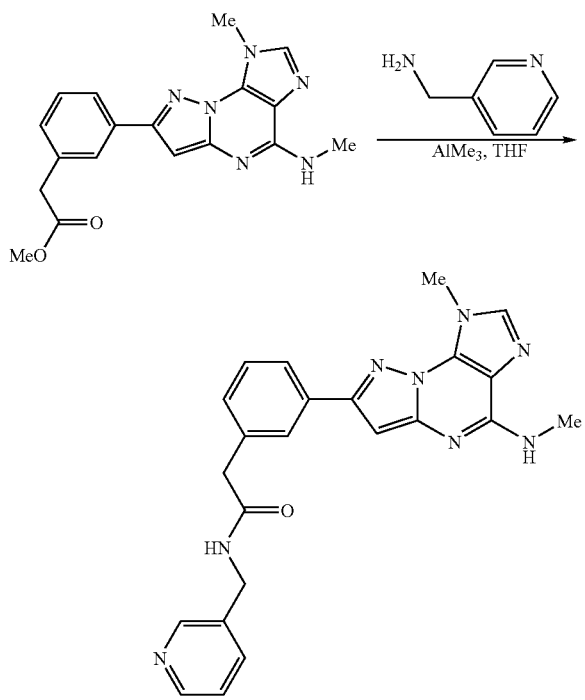

EXAMPLE 61

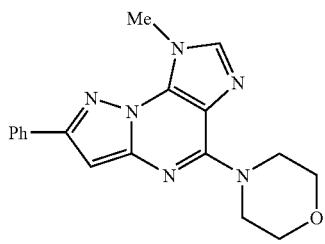

1-Methyl-4-morpholino-7-phenyl-pyrazolo[5,1-b]purine

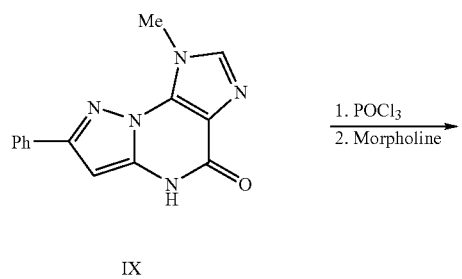

IX

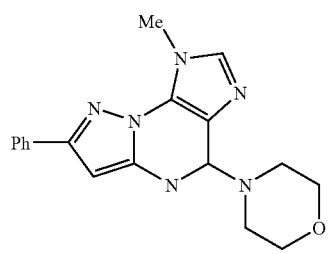

A mixture of IX (26.2 mg, 0.100 mmol) and POCl₃ (2 mL) was stirred at 115° C. for 18 hours. The reaction mixture was concentrated in vacuo and azotroped with toluene twice, and then dried on high vacuum for about 30 min. The residue was suspended in n-butanol, added morpholine (70 uL, 0.100 mmol), and heated to 100° C. The HPLC indicated that the reaction was complete. The reaction mixture was concentrated in vacuo, extracted with EtOAc, washed with water, brine, dried over Na₂SO₄, and concentrated in vacuo to give a crude residue. Prep. HPLC of the residue gave the title compound as a red solid (4 mg). LC/MS (10% MeOH, 90% H20, 0.1% TFA to 90% MeOH, 10% H20, 0.1% TFA, 2 minute gradient with a Phenomenex S5 column 4.6×30 mm): [M+H]⁺ m/z=335.25; retention time=1.70 min.

EXAMPLE 62

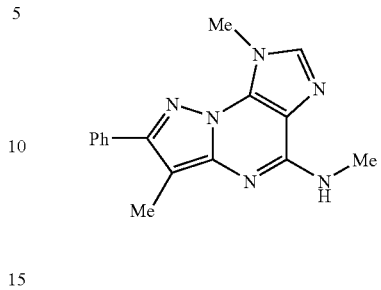

1,6-Dimethyl-4-methylamino-7-phenyl-pyrazolo[5,1-b]purine

A. 4-Methyl-5-phenyl-2H-pyrazol-3-ylamine

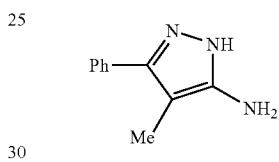

A vial was charged with 2-Methyl-3-oxo-3-phenyl-propionitrile (1.0 g, 6.28 mmol), hydrazine (0.2 mL) and EtOH (1 mL), and subject to microwave irradiation at 100° C. for 50 min. Flach chromatography of the crude product using 3%-5% MeOH in CH₂Cl₂ gave the pyrazolylamine as a yellow oil (0.21 g). LC/MS (10% MeOH, 90% H₂₀, 0.2% H₃PO₄ to 90% MeOH, 10% H20, 0.2% H₃PO₄, 2 minute gradient with an Exterra C18 S-5 column 4.6×30 mm): [M+H]⁺ m/z=174.10; retention time=1.02 min.

B. 1,6-Dimethyl-2-methanesulfonyl-7-phenyl-4H-pyrazolo[5,1-b]purin-4-one

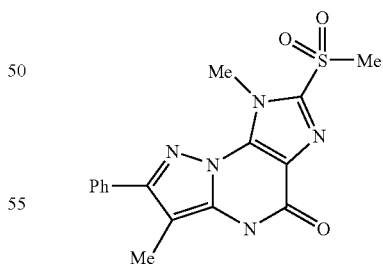

Compound 62B was prepared by a method analogous to the preparation of intermediate IX, starting from compound 62A. LC/MS (10% MeOH, 90% H20, 0.2% H₃PO₄ to 90% MeOH, 10% H20, 0.2% H₃PO₄, 2 minute gradient with an Exterra C18 S-column 4.6×30 mm): [M+H]⁺ m/z=358.19; retention time=1.53 min.

C. 1,6-Dimethyl-7-phenyl-4H-pyrazolo[5,1-b]purin-4-one

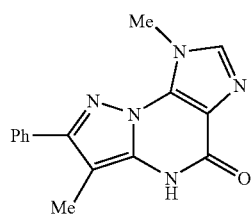

Compound 62C was prepared by a method analogous to the preparation of intermediate X, starting from compound 62B. LC/MS (10% MeOH, 90% H20, 0.2% $H_3PO_4$ to 90% MeOH, 10% H20, 0.2% $H_3PO_4$, 2 minute gradient with an Exterra C18 S-column 4.6×30 mm): [M+H]$^+$ m/z=280.19; retention time=1.41 min.

D. 1,6-Dimethyl-4-chloro-7-phenyl-pyrazolo[5,1-b]purine

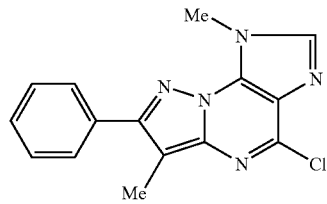

A mixture of 62C (0.55 g, 2.00 mmol) and POCl$_3$ (50 mL) was stirred at 115° C. for 18 hours. The reaction mixture was concentrated in vacuo and azotroped with toluene twice, and then quenched with ice, filtered and dried on high vacuum. The crude product was carried over to the next step without further purification. LC/MS (10% MeOH, 90% H20, 0.2% $H_3PO_4$ to 90% MeOH, 10% H20, 0.2% $H_3PO_4$, 2 minute gradient with an Exterra C18 S-5 column 4.6×30 mm): retention time=1.77 min.

E. 1,6-Dimethyl-4-methylamino-7-phenyl-pyrazolo[5,1-b]purine

A sealed tube was charged with 62D (20.0 mg, 0.067 mmol), diisopropylethylamine (0.75 mL), and methyl amine (5 mg, 0.067 mmol), and subject to microwave irradiation at 180° C. for 50 min. The reaction mixture was concentrated in vacuo and then triturated with MeOH, filtered to give a crude product. Prep. HPLC of the crude product gave the title compound as a solid (4.1 mg). LC/MS (10% MeOH, 90% H20, 0.2% $H_3PO_4$ to 90% MeOH, 10% H20, 0.2% $H_3PO_4$, 2 minute gradient with an Exterra C18 S-5 column 4.6×30 mm): [M+H]$^+$ m/z=293.20; retention time=1.50 min.

EXAMPLE 63

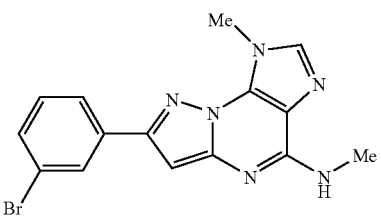

1,6-Dimethyl-4-methylamino-7-(3-bromophenyl)-pyrazolo[5,1-b]purine

A. -5-(3-Bromophenyl)-2H-pyrazol-3-ylamine

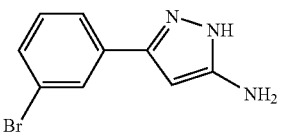

Ten vials were each charged with 3-oxo-3-(3-bromophenyl)propionitrile (1.0 g, 4.5 mmol), hydrazine (0.2 mL) and EtOH (1 mL), and subject to microwave irradiation at 120° C. for 60 min. The contents of all vials was pooled and the solvent was evaporated in vacuo. The crude product was dissolved in ethanol (approx. 200 mL) and acidified by the addition of 4N HLC in dioxane, after 0.5 h the precipitate was collected, washed with additional ethanol and dried to yield 9.60 g. LC/MS (10% MeOH, 90% H$_2$O, 0.2% H$_3$PO$_4$ to 90% MeOH, 10% H$_2$O, 0.2% H$_3$PO$_4$, 2 minute gradient with an Exterra C18 S-5 column 4.6×30 mm): [M+H]$^+$ m/z=239.0, 241.0; retention time=0.85 min.

B. 1-Methyl-2-methanesulfonyl-7-(3-bromophenyl)-4H-pyrazolo[5,1-b]purin-4-one

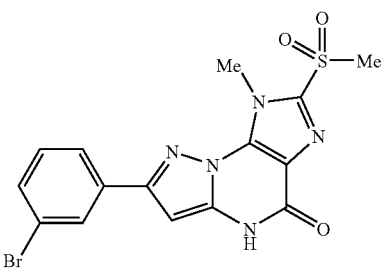

Compound 63B was prepared by a method analogous to the preparation of intermediate IX. Compound 63A (9.6 g, 40 mmol), intermediate VII (7.8 g, 31 mmol) and cesium carbonate (51 g, 160 mmol) were dissolved in 300 mL of DMF and heated at 100° C. for 12 h. The solvent was evaporated and the product suspended in pH 7 buffer and 1N HCL was added until the pH was approximately 7 (by pH paper). An attempt to extract the product into a mixture of ethyl acetate/THF (10:1) (300 mL) failed to disolve the majority of the material. The biphasic mixture was filtered. The solids were azeotroped with toluene to yield 10.10 g (77%) of 63B. LC/MS (10% MeOH, 90% H20, 0.2% H₃PO₄ to 90% MeOH, 10% H20, 0.2% H₃PO₄, 2 minute gradient with an Exterra C18 S-5 column 4.6×30 mm): [M+H]⁺ m/z=424.01; retention time=1.74 min. NMR: (DMSOd₆) δ: 8.12, s, 1H; 7.96, d, (J=7 Hz), 1H; 7.59, d, (J=7 Hz), 1H; 7.42 t, (J=7 Hz) 1H; 6.50, s, 1H; 4.47, s, 3H; 3.55, s, 3H.

C. 1-Methyl-7-(3-bromophenyl)-4H-pyrazolo[5,1-b]purin-4-one

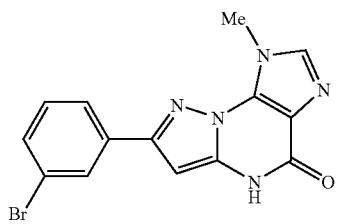

Compound 63B (100.10 g, 24 mmol) was suspended in anhydrous dioxane (100 mL) and cooled in an ice bath. LiBHEt3 (1.0M THF, 96 mL) was added via canula over a period of 5-10 min. The reaction mixture was stirred at this temperature for 1 h, and quenched by the addition of methanol. The solvent was removed in vacuo, and the residue suspended in pH 7 buffer, and and 1N HCL was added until the pH was approximately 7 (by pH paper). The solid was filtered and dried to yield 6.69 g (81%) of 63C a pale yellow solid. LC/MS (10% MeOH, 90% H₂O, 0.1% TFA to 90% MeOH, 10% H₂O, 0.1% TFA, 2 minute gradient with an Phenomenex S5 column 4.6×30 mm @ 5 ml/min: 97% AP, [M+H]⁺ m/z=344.08, 346.08; retention time=1.69 min. NMR 400 MHz: (DMSOd₆) δ: 12.09 br s, 1H; 8.12, s, 1H; 7.97-7.95, m, 2H; 7.57, d, (J=7 Hz, 1H; 7.42 t, (J=7 Hz) 1H; 6.46, s, 1H; 4.14, s, 3H.

D. 1-Methyl-4-chloro-7-(3-bromophenyl)-pyrazolo[5,1-b]purine

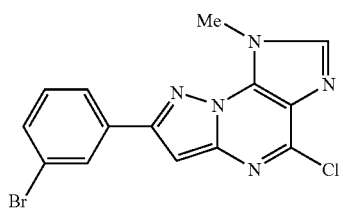

A mixture of 63C (5.0 g, 15 mmol) and freshly distilled POCl₃ (85 mL) was stirred at 100° C. ON. The next day TLC indicated the reaction had not gone to completion. Additional POCL₃ (30 mL) was added and the reation heated for an additional 48 h. The reaction mixture was concentrated in vacuo and dried under high vacuum, and then quenched with ice. When the ice melted, the product was filtered, azeotroped with toluene, and dried under high vacuum to yield 7.32 g (72%) of 63D as a tan solid. LC/MS (10% MeOH, 90% H₂O, 0.1% TFA to 90% MeOH, 10% H₂O, 0.1% TFA, 2 minute gradient with an Phenomenex S5 column 4.6×30 mm @ 5 ml/min: 97% AP, [M+H]⁺ m/z=362.01, 364.00; retention time=1.95 min. NMR 500 MHz: (DMSOd₆) δ: 8.26-8.23, m, 2H; 8.07, d, (J=7 Hz), 1H; 7.60, d, (J=7 Hz), 1H; 7.45 t, (J=7 Hz) 1H; 7.37, s, 1H; 4.31, s, 3H.

E. 1-Methyl-4-methylamino-7-(3-bromophenyl)pyrazolo[5,1-b]purine

Two vials were charged each with 63D (500.0 mg, 1.4 mmol), diisopropylethylamine (0.96 mL), methyl amine hydrochloride (93 mg, 1.4 mmol), and n-butanol (0.5 mL) and subject to microwave irradiation at 180° C. for 50 min. The contents of each vial were pooled, and the reaction mixture was concentrated in vacuo and then triturated with EtOH, filtered and dried under vacuum to yield to provide the title compound as a pale yellow solid (440 mg, 45%). LC/MS (10% MeOH, 90% H₂O, 0.1% TFA to 90% MeOH, 10% H₂O, 0.1% TFA, 2 minute gradient with an Phenomenex S5 column 4.6×30 mm @ 5 mil/min: 99% AP, [M+H]⁺ m/z=357.08, 359.08; retention time=1.62 min. NMR 400 MHz: (DMSOd₆) δ: 8.13, s, 1H; 7.97-7.95, m, 2H; 7.61, br s, 1H; 7.56, d, (J=7 Hz) 1H; 7.45 t, (J=7 Hz) 1H; 4.25, s, 3H; 2.96 d, (J=5 Hz), 1H.

EXAMPLE 64

3-(1-methyl-4-(methylamino)-1H-pyrazolo[5,1-b]purin-7-yl)benzonitrile

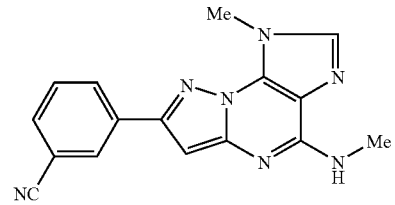

Example 63

3-(1-methyl-4-(methylamino)-1H-pyrazolo[5,1-b]purin-7-yl)benzonitrile

A mixture of Example 63 (0.500 g, 1.40 mmol), zinc cyanide (0.160 g, 1.40 mmol), tetrakistriphenylphosphine (0.530 g, 0.45 mmol) in DMF was heated at 120° C. for 10 min. under Microwave heating conditions. The reaction mixture was cooled to room temperature, diluted with ethyl acetate and filtered. The filtrate was concentrated in vacuo, and the residue purified by chromatography on Reverse-Phase PREP HPLC. The product was obtained as a white solid (17.02 g, 45%). IR: 2247 cm⁻¹ (ν$_{CN}$); ¹H NMR (d-MeOD, 400 MHz): 8.40 (m, 2H), 7.90 (s, 1H), 7.80 (m, 2H), 4.30 (s, 3H), 3.30 (s, 3H); ESI m/z=304.31 HPLC Ret. Time=2.610 min, [LC/MS (10% MeOH, 90% H₂O, 0.1% TFA to 90% MeOH, 10% H₂O, 0.1% TFA, 4 minute gradient with a Shimadzu VP ODS 4.6×30 mm column @ 5 ml/].

EXAMPLES 65-69

Examples 65-69 were prepared by the method described for Example 63 using 63D with commercially available amines or hydrazines.

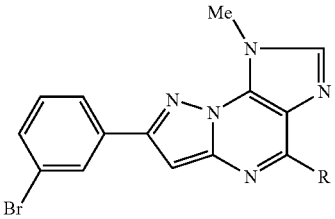

| Example # | R | ESI m/z | Ret. Time* (min) |
|---|---|---|---|
| 65 | 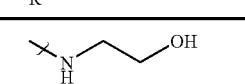 | 387.24, 389.08 | 3.32 |
| 66 | 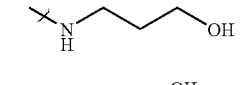 | 401.08, 403.08 | 3.37 |
| 67 | 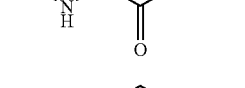 | 401.07, 403.07 | 3.52 |
| 68 | 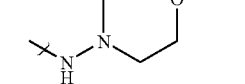 | 428.08, 430.09 | 2.27 |
| 69 | 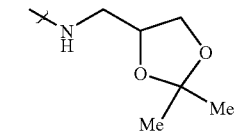 | 457.24, 459.25 | 3.22 |

*LC/MS (10% MeOH, 90% H$_2$O, 0.1% TFA to 90% MeOH, 10% H$_2$O, 0.1% TFA, 4 minute gradient with a Shimadzu VP ODS 4.6 × 30 mm column @ 5 ml/min.

EXAMPLES 70-73

Examples 70-73 were prepared by the method described for Example 64 starting with the appropriate aryl bromide described above.

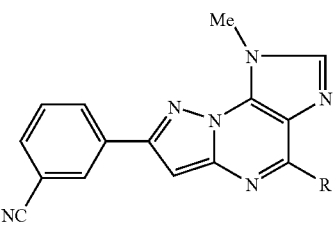

| Example # | R | ESI m/z | Ret. Time* |
|---|---|---|---|
| 70 | 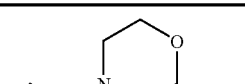 | 375.19 | 2.24 |
| 71 | 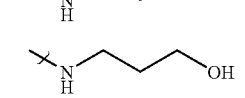 | 348.22 | 2.69 |

-continued

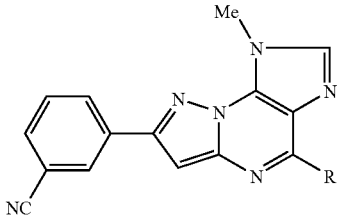

| Example # | R | ESI m/z | Ret. Time* |
|---|---|---|---|
| 72 | 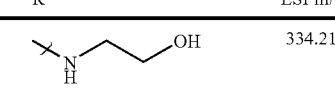 | 334.21 | 2.64 |
| 73$^a$ | 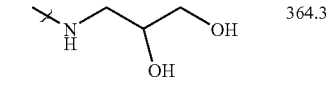 | 364.39 | 2.54 |

*LC/MS (10% MeOH, 90% H$_2$O, 0.1% TFA to 90% MeOH, 10% H$_2$O, 0.1% TFA, 4 minute gradient with a Shimadzu VP ODS 4.6 × 30 mm column @ 5 ml/min.
$^a$Dimethyl acetal hydrolyzed during work up.

EXAMPLE 74

N-((3-(1-methyl-4-methylamino)-1H-pyrazolo[5,1-b]purin-7-yl)methyl)acetamide

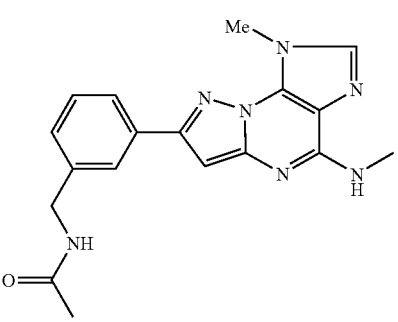

Example 74

N-((3-(1-methyl-4-methylamino)-1H-pyrazolo[5,1-b]purin-7-yl)methyl)acetamide

A mixture Example 38 (0.307 g, 1.0 mmol), in THF was stirred at room temperature. Pyridine (0.5 ml) was added, followed by acetic anhydride (0.5 ml, >1.0 mmol). The reaction mixture was stirred overnight at room temperature. HPLC/LC-MS analysis showed complete conversion to the desired product. The reaction mixture was concentrated in vacuo, and the residue purified by chromatography on Reverse-Phase PREP HPLC. The product was obtained as a white solid (0.285 g, 82%). $^1$H NMR (d-MeOD, 400 MHz): 7.9(m, 3H), 7.35(dd, 1H), 7.20 (d, 1H), 6.55(s,1H), 4.30 (s, 2H), 4.2(s, 3H), 3.2 (s, 3H). ESI m/z=350.17 [(M+H)$^+$; calcd for C$_{14}$H$_{11}$N$_5$O+H: 350]; HPLC RT=2.00 min [LC/MS (10% MeOH, 90% H$_2$O, 0.1% TFA to 90% MeOH, 10% H$_2$O, 0.1% TFA, 4 minute gradient with a Shimadzu VP ODS 4.6×30 mm column @ 5 ml/min.]

EXAMPLES 75-79

Examples 75-79 were prepared by acylation of Example 38 with commercially available acid or sulfonyl chlorides as described for example 74.

| Example # | Structure | ESI m/z | Ret. Time |
|---|---|---|---|
| 75 | (structure: -C(=O)-C(=O)-O-Et) | 408.33 | 2.30 |
| 76 | (structure: -C(=O)-CH2-C(=O)-OH) | 408.33 | 1.96 |
| 77 | (structure: -C(=O)-NH-CH(Me)2) | 393.38 | 2.14 |
| 78 | (structure: -S(=O)2-Me) | 386.38 | 2.01 |
| 79 | (structure: -C(=O)-O-Et) | 390.30 | 2.47 |

EXAMPLE 80

7-(3-(1-aminoethyl)phenyl)-N,1-dimethyl-1H-pyrazolo[5,1-b]purin-4-amine

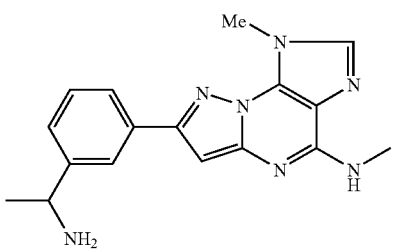

Example 80

7-(3-(1-aminoethyl)phenyl)-N,1-dimethyl-1H-pyrazolo[5,1-b]purin-4-amine

A mixture of Example 64 (0.303 g, 1.0 mmol), in THF was stirred at room temperature. A 1M solution of methylmagnesium bromide (1 ml., 1.0 mmol) was added over 10 minutes. After complete addition the reaction mixture was heated at 60° C. for eight hours. The reaction mixture was cooled to room temperature. A 1.0M solution of lithium aluminum hydride (1.0 ml., 11.0 mmol) was added and the reaction mixture heated at reflux overnight. HPLC/LC-MS analysis showed complete conversion to the desired product. The reaction mixture was quenched sequentially with 2 ml. H20, 2 ml. 15% NaOH, 2 ml. H2O. then filtered through Celite. The filtrate was concentrated in vacuo, and the residue purified by chromatography on Reverse-Phase PREP HPLC. The product was obtained as an clear viscous liquid film (0.150 g, 46%). $^1$H NMR (d-MeOD, 400 MHz): 8.2(m, 2H), 8.0(s, 1H), 7.6 (m, 2H), 6.7(s,1H), 4.6 (m, 1H), 4.3(s, 3H), 3.2 (s, 3H), 1.7(d, 3H). ESI m/z=322.44, Ret. Time=1.54 min [LC/MS (10% MeOH, 90% H$_2$O, 0.1% TFA to 90% MeOH, 10% H$_2$O, 0.1% TFA, 4 minute gradient with a Shimadzu VP ODS 4.6×30 mm column @ 5 ml/min.]

EXAMPLE 81

(3-(1-methyl-4-(methylamino)-1H-pyrazolo[5,1-b]purin-7-yl)phenyl)benzophenone

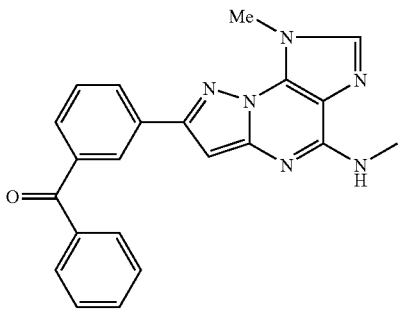

Example 81

(3-(1-methyl-4-(methylamino)-1H-pyrazolo[5,1-b]purin-7-yl)phenyl)benzophenone

A mixture of Example 64 (0150 g, 1.0 mmol), in THF was stirred at room temperature. A 1.5M solution of phenylmagnesium bromide (1 ml., 1.0 mmol) was added over 10 minutes. After complete addition the reaction mixture was stirred overnight at room temperature. The reaction mixture was quenched with 6N HCl and stirred an additional two hours at room temperature. HPLC/LC-MS analysis showed complete conversion to the desired product. The reaction mixture was concentrated in vacuo, and the residue purified by chromatography on Reverse-Phase PREP HPLC. The product was obtained as a white solid. (0.090 g, 46%). $^1$H NMR (d-MeOD, 400 MHz): 8.4(s, 1H), 8.2(d, 1H), 7.9(s, 1H), 7.8 (m, 2H), 7.6(m, 4H), 7.4(d, 1H), 6.7(s, 1H), 4.3(s, 3H), 3.2 (s, 3H), ESI m/z=382.42 [(M+H)⁺; calcd for C$_{14}$H$_{11}$N$_5$O+H: 383]; HPLC RT=3.273 min[4 min grad, 10% MeOH/90% water to 90% MeOH/10% water]

EXAMPLE 82

7-(3-((dimethylamino)methyl)phenyl)-N,1-dimethyl-1H-pyrazolo[5,1-b]purin-4-amine

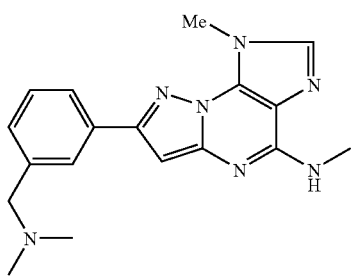

Example 82

7-(3-((dimethylamino)methyl)phenyl)-N,1-dimethyl-1H-pyrazolo[5,1-b]purin-4-amine A mixture of Example 38 (0.153 g, 0.5 mmol), pyridine (0.5 ml) and iodomethane (0.150 g, 1.0 mmol) in THF was stirred at room temperature overnight. HPLC/LC-MS analysis showed complete conversion to the desired product. The reaction mixture was concentrated in vacuo, and the residue purified by chromatography on Reverse-Phase PREP HPLC. The product was obtained as a tan solid (0.050 g, 30%). ESI m/z=335.61 [(M+H)⁺; calcd for C$_{14}$H$_{11}$N$_5$O+H: 336]; HPLC RT=1.353 min[4 min grad, 10% MeOH/90% water to 90% MeOH/10% water].

EXAMPLE 83

3-(1-methyl)-4-(methylamino)-1H-pyrazolo[5,1-b]purin-7-yl)benzamide

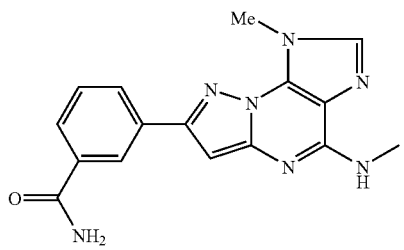

Example 83

3-(1-methyl)-4-(methylamino)-1H-pyrazolo[5,1-b]purin-7-yl)benzamide

A mixture of 3-(1-methyl-4-(methylamino)-1H-pyrazolo[5,1-e]purin-7-yl)benzonitrile (0.303 g, 1.0 mmol), conc. H$_2$SO$_4$(5 ml.) in H$_2$O (5 ml.) was heated at approx. 90° C. for eight hours in a sealed tube. The filtrate was concentrated in vacuo, and the residue purified by chromatography on Reverse-Phase PREP HPLC. The product was obtained as an white solid (0.150 g, 46%). ¹H NMR (d-MeOD, 400 MHz): 8.2(m, 2H), 8.0(s, 1H), 7.6 (m, 2H), 6.7(s,1H), 4.3(s, 3H), 3.2 (s, 3H), ESI m/z=321.34 [(M+H)⁺; calcd for C$_{14}$H$_{11}$N$_5$O+H: 322]; HPLC RT=1.790 min[4 min grad, 10% MeOH/90% water to 90% MeOH/10% water].

EXAMPLE 84

2-(1-Methyl-7-(2-phenoxyethoxy)-1H-pyrazolo[5,1-b]purin-4-ylamino)ethanol

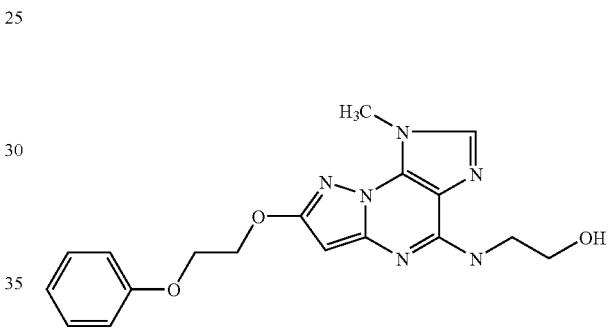

Example 84

Part A: 3-(2-phenoxyethoxy)-1H-pyrazol-5-amine

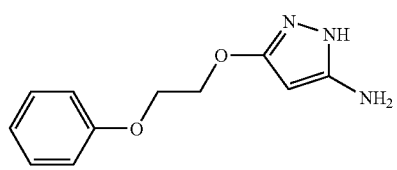

A mixture of 2-phenoxyethanol (56.1 g, 406 mmol), 3-amino-1H-pyrazol-5-ol (8.0648 g, 81.4 mmol) and TsOH (30.96 g, 162.8 mmol) was stirred at 130° C. under vacuum for 11 h. After cooled down to room temperature, the solid was washed with MeCN (200 mL), then treated with 6% aqueous NaHCO$_3$ solution (500 mL). The suspension was filtered, and the solid collected was dissolved in EtOAc (100 mL), dried over MgSO$_4$, filtered and concentrated, giving the title compound (5.4734 g, 30.7% yield). ESI m/z=220.19 [(M+1)⁺; calcd for C$_{11}$H$_{13}$N$_3$O$_2$+H: 220.11].

Example 84

Part B: 1-Methyl-2-(methylsulfonyl)-7-(2-phenoxyethoxy)-1H-pyrazolo[5,1-b]purin-4(5H)-one

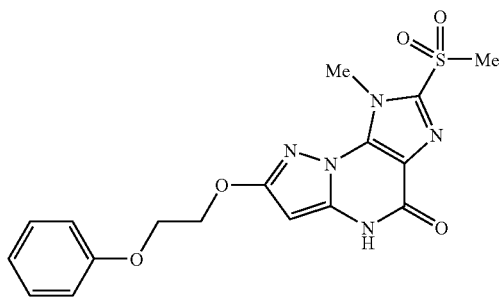

A mixture of Example 84 part A, (2.5187 g, 11.5 mmol), intermediate VII (2.4821 g, 10.4 mmol) and $Cs_2CO_3$ (10.2085 g, 31.3 mmol) was stirred at 130° C. in DMF (anhydrous, 100 mL) under $N_2$. After 6 h, the reaction mixture was filtered and the filtrate was concentrated under high vacuum to remove DMF. The residue was treated with pH 7 buffer solution (40 mL), then carefully neutralized with 1.0 N HCl. The precipitate was filtered and washed with $H_2O$, acetone and EtOAc, providing the title compound (1.876 g, 44.5%) as a white solid. ESI m/z=404.13 [(M+H)$^+$; calcd for $C_{17}H_{17}N_5O_5S$+H: 404.11]

Example 84

Part C: 1-Methyl-7-(2-phenoxyethoxy)-1H-pyrazolo[5,1-b]purin-4(5H)-one

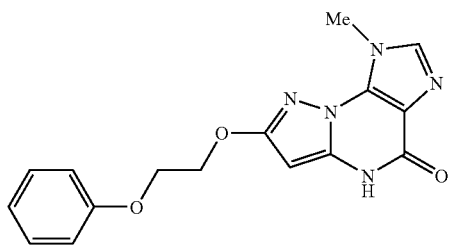

A mixture of Example 84 Part B (1.8575 g, 4.60 mmol) and $NiBr_2(DME)$ (142 mg, 0.46 mmol) in DMPU (100 mL) was treated with $NaBH_4$ (697 mg, 18.4 mmol) under stirring at room temperature. After 20 h, there was still significant amount of starting material left, therefore more $NaBH_4$ (500 mg, 13.2 mmol) and $NiBr_2(DME)$ (1.44 g, 4.67 mmol) were added. Over the subsequent 24 h, additional $NaBH_4$ (2.0 g, 53 mmol) and $NiBr_2(DME)$ (2.7 g, 8.75 mmol) were added to push the reaction to completion. The mixture was then quenched carefully with MeOH at ice temperature and filtered. The filtrate was neutralized with 1.0 N HCl to PH=7.0, precipitating some sticky solid. The solution layer was separated and concentrated. The residual solution was precipitated with EtOAc/hexanes to remove DMPU. The precipitated solid was purified by flash chromatography (MeOH/CHCl$_3$, 3%), giving the title compound (658 mg, 44% yield). ESI m/z=326.25 [(M+H)$^+$; calcd for $C_{16}H_{15}N_5O_3$+H: 326.13].

Example 84

Part D: 4-Chloro-1-methyl-7-(2-phenoxyethoxy)-1H-pyrazolo[5,1-b]purine

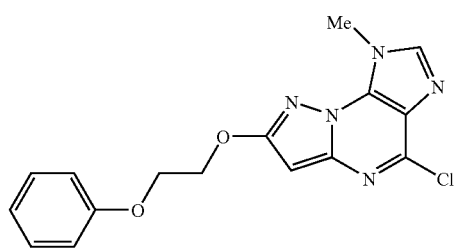

A mixture of 1-methyl-7-(2-phenoxyethoxy)-1H-pyrazolo[5,1-e]purin-4(5H)-one (611.5 mg, mmol) and $PhNEt_2$ (598 mL) in POCl$_3$ was heated to reflux. After 18 h, POCl$_3$ was removed under vacuum. Normal EtOAc/saturated aqueous $Na_2CO_3$ workup, followed by flash chromatography (EtOAc) provided the title compound (365 mg, 56.6% yield). ESI m/z=344.15 [(M+H)$^+$; calcd for $C_{16}H_{14}ClN_5O_2$+H: 344.09].

Example 84

Part E: 2-(1-Methyl-7-(2-phenoxyethoxy)-1H-pyrazolo[5,1-b]purin-4-ylamino)ethanol A solution of Example 84 Part D (22.6 mg, 0.066 mmol) in 2-aminoethanol (5 mL) was heated at 100° C. for 24 h. 2-aminoethanol was then removed under vacuum, and the residue was purified by prep-HPLC, furnishing the title compound (15 mg, 62% yield). ESI m/z=369.24 [(M+H)$^+$; calcd for $C_{18}H_{20}N_6O_3$+H: 369.17].

EXAMPLE 85

7-(2-(3-aminophenyl)ethynyl)-N,1-dimethyl-1H-pyrazolo[5,1-b]purin-4-amine

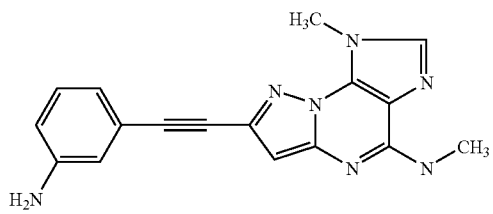

A mixture of intermediate XVII (79.0 mg, 0.226 mmol), 3-ethynylbenzenamine (52.8 mg, 0.451 mmol), Pd(PPh$_3$)$_4$ (52 mg, 0.045 mmol), CuI (8.6 mg, 0.045 mmol), and NEt$_3$ (92 μL, 0.677 mmol) in DMF (2.0 mL) was stirred at 80° C. under $N_2$ for 3 h. Normal EtOAc/H$_2$O workup, followed by flash chromatography (EtOAc/Hexanes, 80:20) provided the desired compound (28.8 mg, 40.2% yield). ESI m/z=318.10 [(M+H)$^+$; calcd for $C_{16}H_{12}N_6O$+H: 318.15]

The following compounds are additionally useful as inhibitors of IKK:

| Example | Compound Structure | ESI m/z | Ret. Time |
|---|---|---|---|
| 100 | (structure) | 338.36 | 1.44 |
| 101 | (structure) | 380.37 | 1.87 |
| 102 | (structure) | 422.35 | 2.43 |

The following tables contain representative examples of the present invention, and may be prepared by procedures described above, or methods familiar to one skilled in the art.

| Example | Compound Structure | ESI m/z | Ret. Time |
|---|---|---|---|
| 86 | (structure) | | |
| 87 | (structure) | | |
| 88 | (structure) | | |

-continued

| Example | Compound Structure | ESI m/z | Ret. Time |
|---|---|---|---|
| 89 | 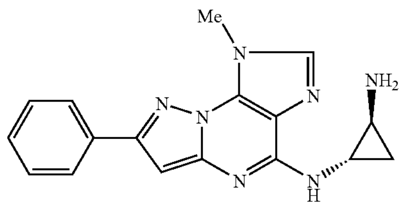 | | |
| 90 | 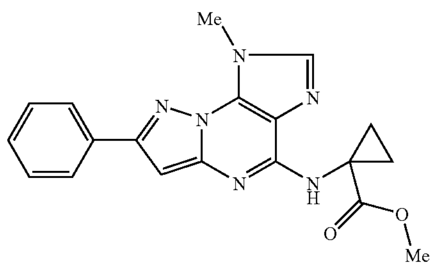 | | |
| 91 | 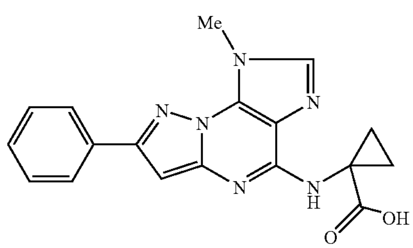 | | |
| 92 | 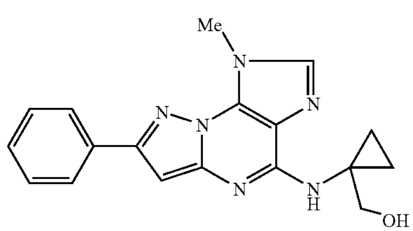 | | |
| 93 | 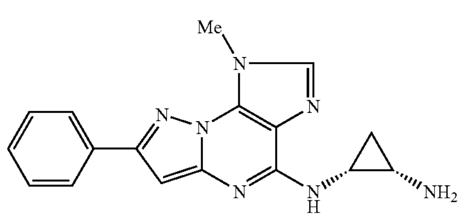 | | |
| 94 | 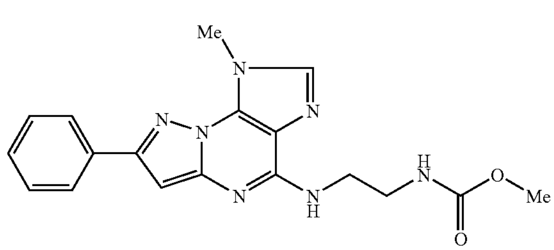 | | |

-continued
| Example | Compound Structure | ESI m/z | Ret. Time |
|---|---|---|---|
| 95 | 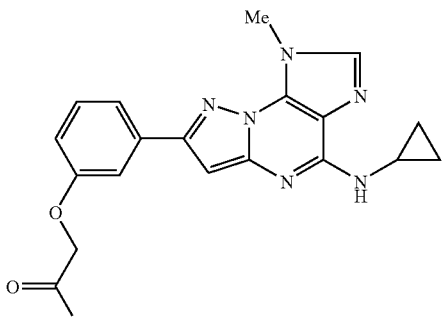 | | |
| 96 | 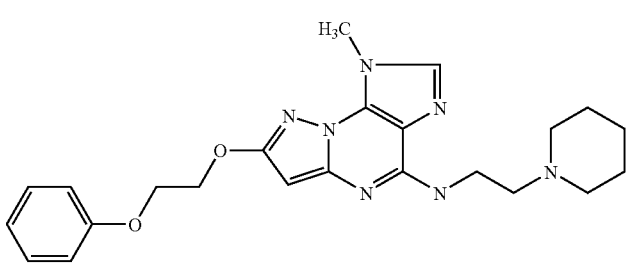 | | |
| 97 | 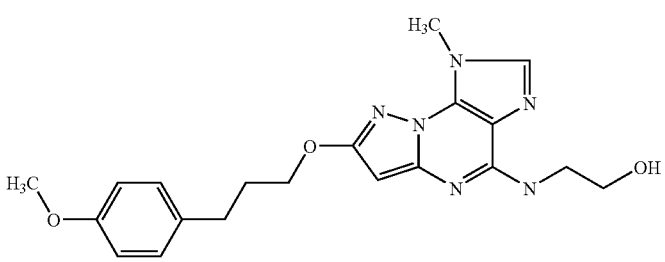 | | |
| 98 | 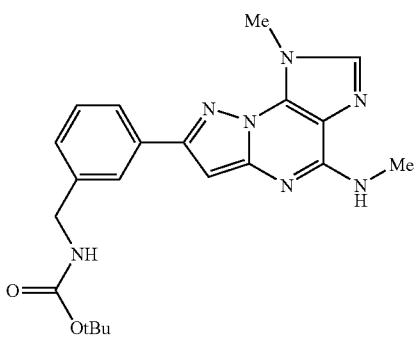 | | |
| 99 | 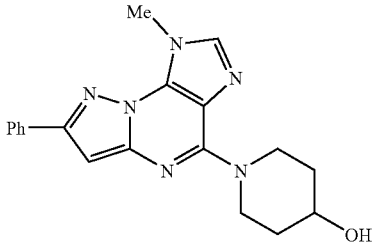 | | |

| Example | Compound Structure | ESI m/z | Ret. Time |
|---------|-------------------|---------|-----------|
| 103 | 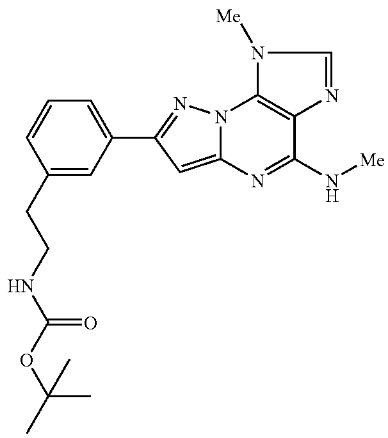 | | |
| 104 | 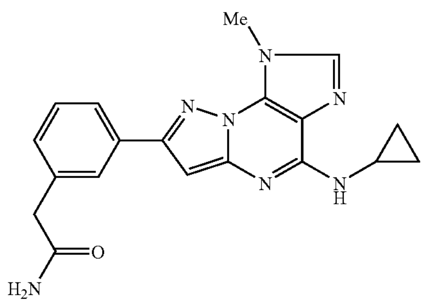 | | |
| 105 | 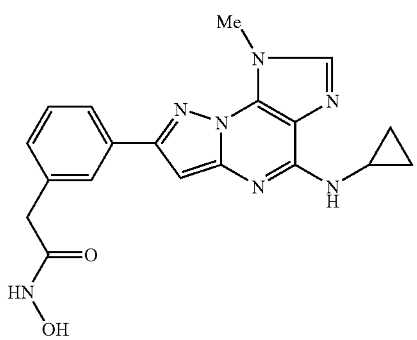 | | |
| 106 | 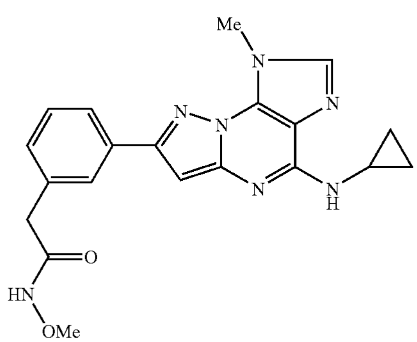 | | |

-continued
| Example | Compound Structure | ESI m/z | Ret. Time |
|---------|-------------------|---------|-----------|
| 107 | 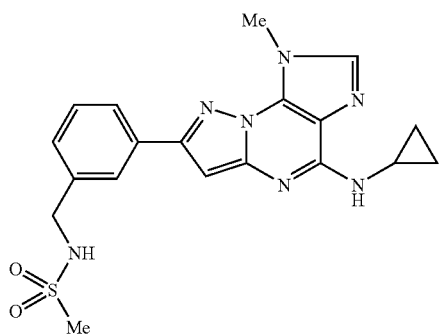 | | |
| 108 | 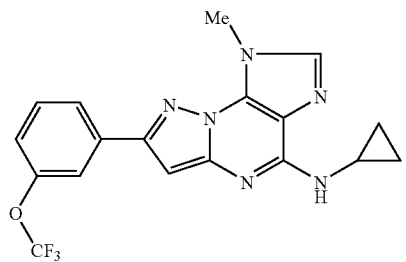 | | |
| 109 | 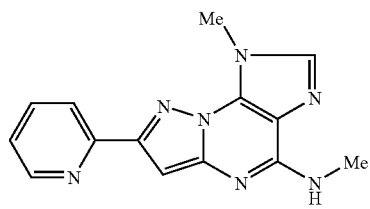 | | |
| 110 | 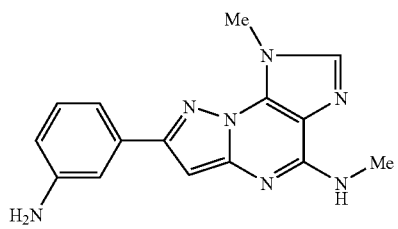 | | |
| 111 | 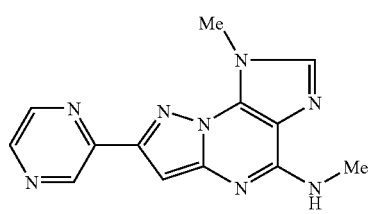 | | |

We claim:

1. A compound of formula (I),

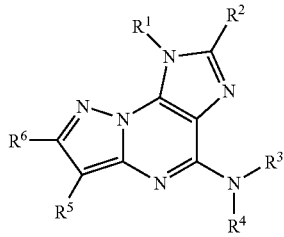

enantiomers, diastereomers, and salts thereof wherein $R^1$ is
  alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^1$, $Z^2$ and $Z^3$;

$R^2$ is
  (a) hydrogen, halo, cyano,
  (b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}$, $Z^{2a}$, and $Z^{3a}$; or
  (c) $-OR^{10a}$, $-SR^{10a}$, or $-SO_2R^{10a}$ $R^3$ and $R^4$ are independently
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
  (c) $-OR^{11}$, $-NR^{12}R^{13}$, $-N(R^{12})C(O)R^{11}$, $-N(R^{12})C(O)OR^{11}$, $-N(R^{12})SO_2R^{14}$, or $-C(O)NR^{12}R^{13}$, $-SO_2NR^{12}R^{13}$, $-N(R^{12})C(O)NR^{12a}R^{13}$, or $-N(R^{12})SO_2NR^{12a}R^{13}$; or
  (d) $R^3$ and $R^4$ together with the nitrogen atom to which they are attached combine to form a heterocyclo ring optionally independently substituted as valence allows with one or more $Z^{1b}$, $Z^{2b}$, and $Z^{3b}$;

$R^5$ is
  (a) hydrogen, halo, hydroxy, cyano,
  (b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$; or
  (c) $-OR^7$, $-C(O)R^7$, $-C(O)OR^7$, or $-NR^8R^9$;

$R^6$ is
  (a) hydrogen, hydroxy, halo, or cyano,
  (b) alkyl, alkenyl, alkynyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
  (c) $-OR^{7a}$, $-NR^{8a}R^{9a}$, $-N(R^{8a})SO_2R^{10}$, $-N(R^{8a})SO_2NR^{8b}R^{9b}$, $-N(R^{8a})C(O)R^{7a}$, $-N(R^{8a})C(O)NR^{8b}R^{9b}$, $-N(R^{8a})C(O)OR^{7a}$, $-C(O)R^{7a}$, $-C(O)OR^{7a}$, $-OC(O)R^{7a}$, $-C(O)NR^{8a}R^{9a}$, or $-OC(O)NR^{8a}R^{9a}$;

$R^7$, $R^{7a}$ and $R^{7b}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^8$, $R^{8a}$, $R^{8b}$, $R^9$ $R^{9a}$ and $R^{9b}$ are independently
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or
  (c) $-OR^{7b}$, $-NR^{8c}R^{9c}$, $-N(R^{8c})SO_2R^{10b}$, $-N(R^{8c})C(O)R^{7b}$, $-N(R^{8c})C(O)OR^{7b}$, $-SO_2NR^{8c}R^{9c}$, $-SO_2R^{10b}$, $-C(O)R^{7b}$, $-C(O)OR^{7b}$, or $C(O)NR^{8c}R^{9c}$;

$R^{8c}$ and $R^{9c}$ are independently
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{10}$, $R^{10a}$ and $R^{10b}$ are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1-1e}$, $Z^{2-2e}$, and $Z^{3-3e}$ are optional substituents independently selected from
  (1) Y, where Y is
    (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
    (ii) a group (i) which is itself substituted by one or more of the same or different groups (i); or
    (iii) a group (i) or (ii) which is independently substituted by one or more (preferably 1 to 3) of the following groups (2) to (13) of the definition of $Z^1$,
  (2) $-OH$ or $-OY^1$,
  (3) $-SH$ or $-SY^1$,
  (4) $-C(O)_tH$, $-C(O)_tY^1$, or $-O-C(O)Y^1$, where t is 1 or 2,
  (5) $-SO_3H$, or $-S(O)_tY^1$,
  (6) halo,
  (7) cyano, (8) nitro,
(9) —$U^1$—$NY^2Y^3$,
(10) —$U^1$—$N(Y^1)$—$U^2$—$NY^2Y^3$,
(11) —$U^1$—$N(Y^4)$—$U^2$—$Y^1$,
(12) —$U^1$—$N(Y^4)$—$U^2$—H,
(13) oxo;

$U^1$ and $U^2$ are each independently
(1) a single bond,
(2) —$U^3$—$S(O)_t$—$U^4$—,
(3) —$U^3$—C(O)—$U^4$—,
(4) —$U^3$—C(S)—$U^4$—,
(5) —$U^3$—O—$U^4$—,
(6) —$U^3$—S—$U^4$—,
(7) —$U^3$—O—C(O)—$U^4$—,
(8) —$U^3$—C(O)—O—$U^4$—, or
(9) —$U^3$—C(=$NV^{1a}$)—$U^4$—;

$V^{1a}$ is independently hydrogen, alkyl, —CN, —C(O)$Y^1$, —$S(O)_2Y^5$, $S(O)_2NY^2Y^3$;

$Y^1$, $Y^2$, $Y^3$ and $Y^4$
(1) are each independently hydrogen or a group provided in
(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(ii) a group (i) which is itself substituted by one or more of the same or different groups (i),
(iii) a group (i) or (ii) which is independently substituted by one or more (preferably 1 to 3) of the following groups (1) to (12) of the definition of $Z^4$, or
(2) $Y^2$ and $Y^3$ may together be alkylene or alkenylene, completing a 3- to 8-membered saturated or unsaturated ring together with the atoms to which they are attached, which ring is unsubstituted or substituted with one or more groups selected from alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, or
(3) $Y^2$ or $Y^3$, together with $Y^1$, may be alkylene or alkenylene completing a 3- to 8-membered saturated or unsaturated ring together with the nitrogen atoms to which they are attached, which ring is unsubstituted or substituted with one or more groups selected from alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, or
(4) $Y^2$ and $Y^3$ together with the nitrogen atom to which they are attached may combine to form a group —N=$CY^5Y^6$ where $Y^5$ and $Y^6$ are each independently H or a group provided selected from alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; and $Z^4$ is
(1) —OH or —$OY^a$,
(2) —SH or —$SY^a$,
(3) —C(O)H, —$C(O)_tY^a$, or —O—C(O)$Y^a$, where t is 1 or 2,
(4) —$SO_3$H, or —$S(O)_tY^a$,
(5) halo,
(6) cyano,
(7) nitro,
(8) —$U^1$—$NY^bY^c$,
(9) —$U^1$—$N(Y^1)$—$U^2NY^bY^c$,
(10) —$U^1$—$N(Y^d)$—$U^2$—$Y^a$,
(11) —$U^1$—$N(Y^d)$—$U^2$—H,
(12) oxo;

$Y^a$, $Y^b$, $Y^c$ and $Y^d$
(1) are each independently hydrogen or a group provided in
(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

$U^3$ and $U^4$ are each independently
(1) a single bond,
(2) alkylene,
(3) alkenylene, or
(4) alkynylene.

2. A compound of claim 1 wherein
$R^3$ and $R^4$ are independently
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1b}$, $Z^{2b}$ and $Z^{3b}$; or
(c) $R^3$ and $R^4$ together with the nitrogen atom to which they are attached combine to form a heterocyclo ring optionally independently substituted as valence allows with one or more $Z^{1b}$, $Z^{2b}$ and $Z^{3b}$.

3. A compound of claim 2 wherein
$R^6$ is
(a) alkyl, alkenyl, alkynyl, heteroaryl or aryl any of which may be optionally independently substituted as valence allows with one or more $Z^{1d}$, $Z^{2d}$ and $Z^{3d}$; or
(b) —$OR^{7a}$.

4. A compound of claim 3 wherein $R^{7a}$ is alkyl optionally substituted with $Z^{1c}$.

5. A compound of claim 4 wherein
$Z^{1b}$, $Z^{2b}$ and $Z^{3b}$ are optional substituents independently selected from —OH, —$OY^1$, —$U^1$—$NY^2Y^3$, —$C(O)_tH$, —$C(O)^tY^1$, —$N(Y^1)$—$U^2$—$NY^2Y^3$, —$N(Y^4)$—$U^2$—$Y^1$, or —$N(Y^4)$—$U^2$—H;

$Z^{1c}$ is
(a) —OH, —$OY^1$ or
(b) aryl optionally substituted with —OH or —$OY^1$;

$Z^{1d}$, $Z^{2d}$ and $Z^{3d}$ are optional substituents independently selected from
(a) cyano, halo, —OH, —$OY^1$, —$U^1$—$NY^2Y^3$, —$C(O)_tH$, —$C(O)_tY^1$, —$S(O)_tY^1$, —$N(Y^1)$—$U^2$—$NY^2Y^3$, —$N(Y^4)$—$U^2$—Y, or —$N(Y^4)$—$U^2$—H;
(b) alkyl or alkoxy optionally substituted with one or more cyano, halo, —OH, —$OY^1$, —$U^1$—$NY^2Y^3$, —$C(O)_tH$, —$C(O)_tY^1$, —$S(O)_tY^1$, —$N(Y^1)$—$U^2$—$NY^2Y^3$, —$N(Y^4)$—$U^2$—$Y^1$, or —$N(Y^4)$—$U^2$—H.

6. A compound of claim 5 wherein
$R^3$ is hydrogen;
$R^4$ is alkyl, haloalkyl, (hydroxy)alkyl, cycloalkyl, (cycloalkyl)alkyl, heterocyclo, (heterocyclo)alkyl, (aryl)alkyl or (heteroaryl)alkyl any of which may be optionally independently substituted as valence allows with one or more $Z^{1b}$, $Z^{2b}$ and $Z^{3b}$;
$R^6$ is
(a) alkynyl optionally substituted with $Z^{1d}$ where $Z^{1d}$ is aryl which may be further optionally independently substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^1$)—U$^2$—NY$^2$Y$^3$, —N(Y$^4$)—U$^2$—Y$^1$, or —N(Y$^4$)—U$^2$—H;

(b) aryl optionally independently substituted as valence allows with one or more Z$^{1d}$, Z$^{2d}$ and Z$^{3d}$;

(c) —OR$^{7a}$; or (d) heterocyclo optionally independently substituted as valence allows with one or more Z$^{1d}$, Z$^{2d}$ and Z$^{3d}$;

Z$^{1b}$, Z$^{2b}$ and Z$^{3b}$ are optional substituents independently selected from —OH, —OY$^1$, —U$^1$—NY$^2$Y$^3$, —C(O)$_t$H, —C(O)$_t$Y$^1$, —N(Y$^4$)—U$^2$—Y, or —N(Y$^4$)—U$^2$—H where U$^1$ is a bond, U$^2$ is —U$^3$—C(O)—U$^4$— or —U$^3$—C(O)O—U$^4$— and U$^3$ and U$^4$ are independently a bond or alkylene;

Z$^{1c}$ is (a) —OY$^1$ where Y$^1$ is aryl, or (b) aryl optionally substituted with —OH or —OY$^1$ where Y$^1$ is alkyl;

Z$^{1d}$, Z$^{2d}$ and Z$^{3d}$ are optional substituents independently selected from (a) cyano, halo, —OH, —OY$^1$, —C(O)$_t$H, —C(O)$_t$Y$^1$, —S(O)$_t$Y$^1$, or (b) alkyl or alkoxy optionally substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^4$)—U$^2$—Y$^1$, or —N(Y$^4$)—U$^2$—H where U$^1$ is a bond, or —C(O)—, U$^2$ is —U$^3$—C(O)—U$^4$—, —U$^3$—C(O)O—U$^4$—, or —U$^3$—SO$_2$—U$^4$—, and U$^3$ and U$^4$ are independently a bond or alkylene.

7. A compound of claim 6 wherein

R$^1$ is alkyl;

R$^2$ is hydrogen; and

R$^5$ is hydrogen or alkyl.

8. A compound of claim one having the formula IIa

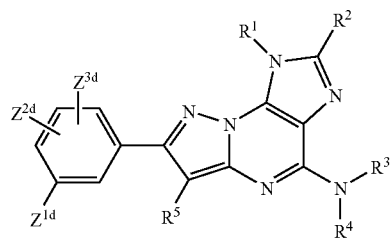

IIa wherein

Z$^{1d}$ is (a) cyano, halo, —OH, OY$^1$, —C(O)$_t$H, —C(O)$_t$Y$^1$, —S(O)$_t$Y$^1$, or (b) alkyl or alkoxy optionally substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^4$)—U$^2$—Y$^1$, or —N(Y$^4$)—U$^2$—H where U$^1$ is a bond, or —C(O)—, U$^2$ is —U$^3$—C(O)—U$^4$—, —U$^3$—C(O)O—U$^4$—, or —U$^3$—SO$_2$—U$^4$—, and U$^3$ and U$^4$ are independently a bond or alkylene; and Z$^{2d}$ and Z$^{3d}$ are optional substituents independently selected from (a) cyano, halo, —OH, OY$^1$, —C(O)$_t$H, —C(O)$_t$Y$^1$, —S(O)$_t$Y$^1$, or (b) alkyl or alkoxy optionally substituted with one or more cyano, halo, —OH, OY$^1$, —U$^1$—NY$^2$Y$^3$, —C(O)$_t$H, —C(O)$_t$Y$^1$, —S(O)$_t$Y$^1$, —N(Y$^4$)—U$^2$—Y$^1$, or —N(Y$^4$)—U$^2$—H where U$^1$ is a bond, or —C(O)—, U$^2$ is —U$^3$—C(O)—U$^4$—, —U$^3$—C(O)O—U$^4$—, or —U$^3$—SO$_2$—U$^4$—, and U$^3$ and U$^4$ are independently a bond or alkylene.

9. A compound of claim 8 wherein

R$^3$ and R$^4$ are independently (a) hydrogen, (b) alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$; or (c) R$^3$ and R$^4$ together with the nitrogen atom to which they are attached combine to form a heterocyclo ring optionally independently substituted as valence allows with one or more Z$^{1b}$, Z$^{2b}$ and Z$^{3b}$.

10. A compound of claim 9 wherein

Z$^{1b}$, Z$^{2b}$ and Z$^{3b}$ are optional substituents independently selected from —OH, —OY$^1$, —U$^1$—NY$^2$Y$^3$, —C(O)$_t$H, —C(O)$_t$Y$^1$, —N(Y$^1$)—U$^2$—NY$^2$Y$^3$, —N(Y$^4$)—U$^2$—Y$^1$, or —N(Y$^4$)—U$^2$—H.

11. A compound of claim 10 wherein

R$^1$ is alkyl;

R$^2$ is hydrogen; and

R$^5$ is hydrogen or alkyl.

12. A compound of claim 1 having formula IIb

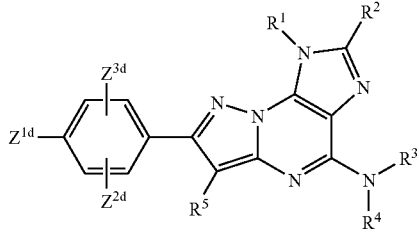

IIb wherein

Z$^{1d}$ is (a) cyano, halo, —OH, OY$^1$, —C(O)$_t$H, —C(O)$_t$Y$^1$, —S(O)$_t$Y$^1$, or (b) alkyl or alkoxy optionally substituted with one or more cyano, halo, —OH, —OY$^1$, —U$^1$—NY$^2$Y$^3$, —C(O)$_t$H, —C(O)$_t$Y$^1$, —S(O)$_t$Y$^1$, —N(Y$^4$)—U$^2$—Y$^1$, or —N(Y$^4$)—U$^2$—H where U$^1$ is a bond, or —C(O)—, U$^2$ is —U$^3$—C(O)—U$^4$—, —U$^3$—C(O)O—U$^4$—, or —U$^3$—SO$_2$—U$^4$—, and U$^3$ and U$^4$ are independently a bond or alkylene; and Z$^{2d}$ and Z$^{3d}$ are optional substituents independently selected from (a) cyano, halo, —OH, —OY$^1$, —C(O)$_t$H, —C(O)$_t$Y$^1$, —S(O)$_t$Y$^1$, or (b) alkyl or alkoxy optionally substituted with one or more cyano, halo, —OH, —$OY^1$, —$U^1$—$NY^2Y^3$, —$C(O)_tH$, —$C(O)_tY^1$, —$S(O)_tY^1$, —$N(Y^4)$—$U^2$—$Y^1$, or —$N(Y^4)$—$U^2$—H where $U^1$ is a bond, or —C(O)—, $U^2$ is —$U^3$—C(O)—$U^4$—, —$U^3$—C(O)O—$U^{4-}$, or —$U^3$—$SO_2$—$U^4$—, and $U^3$ and $U^4$ are independently a bond or alkylene.

13. A compound of claim 12 wherein
$R^3$ and $R^4$ are independently
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$; or
(c) $R^3$ and $R^4$ together with the nitrogen atom to which they are attached combine to form a heterocyclo ring optionally independently substituted as valence allows with one or more $Z^{1b}$, $Z^{2b}$ and $Z^{3b}$.

14. A compound of claim 13 wherein
$Z^{1b}$, $Z^{2b}$ and $Z^{3b}$ are optional substituents independently selected from —OH, —$OY^1$, —$U^1$—$NY^2Y^3$, —$C(O)_tH$, —$C(O)_tY^1$, —$N(Y^1)$—$U^2$—$NY^2Y^3$, —$N(Y^4)$—$U^2$—$Y^1$, or —$N(Y^4)$—$U^2$—H.

15. A compound of claim 14 wherein
$R^1$ is alkyl;
$R^2$ is hydrogen; and
$R^5$ is hydrogen or alkyl.

16. A pharmaceutical composition comprising (a) at least one compound according to claim 1, or a pharmaceutically acceptable salt thereof, and (b) a pharmaceutically-acceptable carrier or diluent.

17. A method of treating rheumatoid arthritis, asthma, inflammatory bowel disease, chronic obstructive pulmonary disease or psoriasis comprising administering to a mammal in need thereof a therapeutically-effective amount of at least one compound according to claim 1.

* * * * *